US008821862B2

(12) United States Patent
Madhyastha et al.

(10) Patent No.: US 8,821,862 B2
(45) Date of Patent: *Sep. 2, 2014

(54) SOLUBLE β-N-ACETYLGLUCOSAMINIDASE BASED ANTIBIOFILM COMPOSITIONS AND USES THEREOF

(75) Inventors: Srinivasa Madhyastha, Winnipeg (CA); Nanda Yakandawala, Winnipeg (CA); Purushottam V. Gawande, Winnipeg (CA); Karen Lovetri, Winnipeg (CA); Jeffrey B. Kaplan, Monsey, NJ (US); Daniel Rhoads, Lubbock, TX (US); Lasha Gogokhia, Lubbock, TX (US)

(73) Assignees: Kane Biotech Inc., Winnipeg (CA); University of Medicine and Dentistry of New Jersey, New Brunswick, NJ (US)

( * ) Notice: Subject to any disclaimer, the term of this patent is extended or adjusted under 35 U.S.C. 154(b) by 187 days.

This patent is subject to a terminal disclaimer.

(21) Appl. No.: 13/416,793

(22) Filed: Mar. 9, 2012

(65) Prior Publication Data

US 2012/0258089 A1 Oct. 11, 2012

Related U.S. Application Data

(60) Continuation-in-part of application No. 12/445,403, filed as application No. PCT/CA2007/001807 on Oct. 12, 2007, now abandoned, application No. 13/416,793, which is a continuation-in-part of application No. 13/195,573, filed on Aug. 1, 2011, now Pat. No. 8,580,551, which is a continuation of application No. 11/833,705, filed on Aug. 3, 2007, now Pat. No. 7,989,604, which is a division of application No. 10/538,902, filed as application No. PCT/US03/34683 on Oct. 31, 2003, now Pat. No. 7,294,497.

(60) Provisional application No. 60/969,355, filed on Aug. 31, 2007, provisional application No. 60/950,416, filed on Jul. 18, 2007, provisional application No. 60/945,474, filed on Jun. 21, 2007, provisional application No. 60/890,320, filed on Feb. 16, 2007, provisional application No. 60/870,762, filed on Dec. 19, 2006, provisional application No. 60/829,420, filed on Oct. 13, 2006, provisional application No. 60/435,817, filed on Dec. 20, 2002.

(51) Int. Cl.
*A61K 38/46* (2006.01)
*A61K 38/47* (2006.01)

(52) U.S. Cl.
CPC ............... *A61K 38/47* (2013.01); *C12Y 302/00* (2013.01)
USPC ........................................ 424/94.65; 435/200

(58) Field of Classification Search
CPC ................................................. C12Y 302/01052
USPC .................................. 435/73, 200; 424/94.65
See application file for complete search history.

(56) References Cited

U.S. PATENT DOCUMENTS

| 7,294,497 | B2 * | 11/2007 | Kaplan | 435/200 |
| 7,833,523 | B2 * | 11/2010 | Kaplan | 424/94.6 |
| 8,580,551 | B2 * | 11/2013 | Kaplan | 435/200 |
| 8,617,542 | B2 * | 12/2013 | Madhyastha et al. | 424/94.65 |

* cited by examiner

*Primary Examiner* — Tekchand Saidha
(74) *Attorney, Agent, or Firm* — Barnes & Thornburg LLP

(57) ABSTRACT

The present invention provides compositions comprising an antibiofilm enzyme, a soluble β-N-acetylglucosaminidase similar to the dspB gene (DispersinB®), and an antimicrobial for preventing growth and proliferation of biofilm-embedded microorganisms in acute and chronic wounds, and methods of treatment. The invention further provides methods for preparing medical devices, and in particular, wound care devices using soluble β-N-acetylglucosaminidase based antimicrobial compositions.

20 Claims, 29 Drawing Sheets

SOLUBLE β-N-ACETYLGLUCOSAMINIDASE BASED ANTIBIOFILM COMPOSITIONS AND USES THEREOF

CROSS-REFERENCE TO RELATED APPLICATIONS

This application is a Continuation-in-Part of U.S. Ser. No. 12/445,403, filed Sep. 23, 2010, and of U.S. Ser. No. 13/195, 573, filed Aug. 1, 2011; U.S. Ser. No. 12/445,403, which is a national stage entry under 35 U.S.C. §371 of PCT/CA2007/001807, filed Oct. 12, 2007, which claims benefit under 35 U.S.C. §119(e) of U.S. Ser. No. 60/969,355, filed Aug. 31, 2007, U.S. Ser. No. 60/950,416, filed Jul. 18, 2007, U.S. Ser. No. 60/945,474, filed Jun. 21, 2007, U.S. Ser. No. 60/890, 320, filed Feb. 16, 2007, U.S. Ser. No. 60/870,762, filed Dec. 19, 2006, and U.S. Ser. No. 60/829,420, filed Oct. 13, 2006; U.S. Ser. No. 13/195,573 is a continuation of U.S. Ser. No. 11/833,705, filed Aug. 3, 2007, now issued as U.S. Pat. No. 7,989,604, which is a divisional of U.S. Ser. No. 10/538,902, filed May 15, 2006, now issued as U.S. Pat. No. 7,294,497, which is national stage entry under 35 U.S.C. §371 of PCT/US2003/034683, filed Oct. 31, 2003, which claims benefit under 35 U.S.C. §119(e) of U.S. Ser. No. 60/435,817, filed Dec. 20, 2002, the entire disclosures of which are hereby incorporated by reference. To the extent appropriate, a claim of priority is made to each of the above disclosed applications.

FIELD OF THE INVENTION

The present invention relates to antibiofilm enzyme DispersinB™-based antimicrobial compositions that inhibit growth and proliferation of biofilm-embedded microorganisms, and methods of administering the compositions.

BACKGROUND

From a microbiological perspective, the primary function of normal, intact skin is to control microbial populations that live on the skin surface and to prevent underlying tissue from becoming colonized and invaded by potential pathogens. Exposure of subcutaneous tissue (i.e. a wound) provides a moist, warm and nutritious environment that is conducive to microbial colonization and proliferation.

Since wound colonization is mostly polymicrobial, involving numerous microorganisms that are potentially pathogenic, any wound is at some risk of becoming infected. In the event of an infection a wound fails to heal, the patient suffers increased trauma as well as increased treatment costs. General wound management practices become more resource demanding. Wounds are an enormous problem worldwide. Approximately 1% of the world's population suffers a venous leg ulcer (Ruckley, 1997. Angiology, 48: 67-69). Friedberg et al. estimated the annual cost for dealing with venous leg ulcers in 192 patients to be $1.26 million (Friedberg et al., 2002. *J. Wound. Ostomny. Continence. Nurs.* 29: 186-192). This equals 6.5 billion of direct wound care cost for every 1 million venous leg ulcer patients. Pressure ulcers are a common and expensive wound care problem in acute care, nursing homes and home care populations. For decubitus ulcer, Stausberg et al. (2005) demonstrated 1% incidence rate along with a 5% prevalence rate for hospital patients (Stausberg et al., 2005. *Adv. Skin Wound. Care,* 18: 140-145). Bennett et al. found that the management of decubitus ulcers costs approximately 3-4 billion dollars annually in the United Kingdom, which is over 4% of the total National Health Service expenditure in the United Kingdom (Bennett et al., 2004. *Ageing,* 33: 230-235). In the United States, diabetic foot ulcers in 2004 consumed approximately 10 billion dollars in direct cost (approximately 4% of the total personal health spending of the United States) and another $5 billion in indirect cost (disability, nursing homes, etc.). Diabetic foot ulcers caused over 100,000 major diabetic limb amputations. The cost for each amputation when factoring in associated costs was $100, 000 in 2005, resulting in $10 billion in direct cost (Heyneman and Lawless-Liday, 2002. *Critical Care Nurse,* 22: 52-60). Wounds are becoming an increased portion of the cost of the healthcare system.

Thus, concern among health care practitioners regarding the risk of wound infection is justifiable not only in terms of increased trauma to the patient but also in view of its burden on financial resources and the increasing requirement for cost-effective management within the health care system. Most wound infections are caused by *Staphylococcus aureus* (20%), *Staphylococcus epidermidis* (14%), Enterococci spp. (12%), *Escherichia coli* (8%), *Pseudomonas aeruginosa* (8%), *Enterobacter* spp. (7%), *Proteus* spp. (3%), *Klebsiella pneumoniae* (3%), Streptococci (3%) and *Candida albicans* (3%) (CDC Report on common bacterial species associated with wound infections, 1996).

In recent years, there have been numerous efforts to use antibiotics and antimicrobials for the treatment of non-healing, clinically infected wounds. These antimicrobial agents are of varying chemical composition and can include peptides (Zaleski et al., 2006, *Antimicrob. Agents Chemother.,* 50: 3856-3860), antiseptics (U.S. Pat. No. 6,700,032), antibiotics (Rothstein, et al., 2006, *Antimicrob. Agents Chemother,* 50: 3658-3664; Rittenhouse, et al., 2006, *Antimicrob. Agents Chemother.* 50: 3886-3888), silver ions/compounds (US patent appl. pub. no. 2005/0035327), chitosan (US patent appl. pub. no. 2006/0210613; U.S. Pat. No. 6,998,509), nitrofurazone (Munster, 1984, *J. Trauma* 24: 524-525), bismuth thiols (Domenico, et al., 2000, *Infect. Med.* 17: 123-127), and xylitol (WO 2005/058381).

There have been various attempts by others to create wound care devices such as dressings or bandages, gels and ointments comprising antimicrobial agents. For example, U.S. Pat. No. 3,930,000 discloses the use of a silver zinc allantoinate cream for killing bacteria and fungi associated with burn wounds. Another example is silver sulfadiazine (SILVA-DINE®), which has been shown to be effective when tested in vitro against 50 strains of methicillin resistant *S. aureus* (MRSA). Numerous products are commercially available with different trade names that employ silver as antimicrobial agents such as STERIPURE®, A.M.Y., ACTI-COAT™, ACTISORB®, and SILVERLON®.

U.S. Pat. No. 7,091,336 teaches the process of making a gel containing gellan gum that increases in viscosity once applied to the wound to form an immobile gel. One example of a commercially available wound gel is INTRASITE®, contains carboxymethyl cellulose as a main ingredient. U.S. Pat. No. 6,700,032 discloses the application of triclosan in wound dressing fabricated from a natural or synthetic film-forming material, such as hydrophobic polymeric membrane. DeBusk and Alleman disclose a wound dressing that has been infused with a suspension of starch hydrolysate containing collagen and α-tocopherol acetate (U.S. patent appl. Pub. No. 2004/0001878). Wounds, in particular those occurring in the skin as second and third degree burns, stasis ulcers, tropic lesions, such as decubitus ulcers, severe cuts and abrasions that are commonly resistant to the natural healing process, may be treated with the infused dressing. Progress has been made on developing wound care devices, but each of the wound etiologies are increasing at double digit rates annually, causing the number of wounds to double every 4-5 years (Drosou et al., 2003, *Wounds*, 15:149-166).

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment (biofilm) following their attachment to a surface, the ability of the host to control these organisms is likely to decrease as the biofilm community matures. Within a stable biofilm community, interactions between aerobic and anaerobic bacteria are likely to increase their net pathogenic effect, enhancing their potential to cause infection and delay healing. Over the last few years, some have linked biofilm to chronic wounds (Mertz, 2003, *Wounds*, 15: 1-9). Microscopic evaluation or chronic wounds showed well organized biofilm with extracellular polymeric substance adhered around colony bacteria in at least 60% of the chronic wounds (Mertz, 2003, *Wounds*, 15: 1-9).

In addition to a direct effect on wound healing by the production of destructive enzymes and toxins, mixed communities of microorganisms may also indirectly affect healing by promoting a chronic inflammatory state. Prolonged exposure to bacteria within a chronic wound leads to a prolonged inflammatory response, resulting in the release of free radicals and numerous lytic enzymes that could have a detrimental effect on cellular processes involved in wound healing. Proteinases released from a number of bacteria, particularly *Pseudomonas aeruginosa*, are known to affect growth factors and many other tissue proteins that are necessary for the wound healing process (Steed et al., 1996, *J. Am. Coll. Surg*, 183: 61-64; Travis et al., 1995, *Trends Microbiol.* 3: 405-407). The increased production of exudates that often accompanies increased microbial load has been associated with the degradation of growth factors and matrix metalloproteinases (MMPs), which subsequently affect cell proliferation and wound healing (Falanga et al., 1994, *J Invest Dermatol.* 1: 125-127).

Dental plaque is a host-associated biofilm that adheres to the tooth surface both above and below the gingival margin. Dental plaque consists mainly of microorganisms with a small number of epithelial cells, leukocytes, and macrophages in an intracellular matrix. It has been postulated that there are approximately 300 to 400 different bacterial species in dental plaque (Moore, 1987, *J. Periodont. Res.* 22: 335-341). Periodontal disease comprises a collection of inflammatory conditions of the periodontium (gingiva, periodontal ligament, cementum, and alveolar bone) due to a chronic bacterial infection, i.e., dental plaque. Over 90% of the population of the United States is affected by periodontal disease (Brown et al., 1996, *J. Dent. Res.* 75: 672-683).

In addition to periodontal diseases, other conditions/diseases caused by biofilms include cystic fibrosis, pneumonia, native valve endocarditis and otitis media (Costerton et al. Science 1999 284:1318-1322). Biofilm is also implicated in the infection of various medical devices such as urinary catheters, mechanical heart valves, cardiac pacemakers, prosthetic joints, and contact lenses (Donlan, R. M. 2001 Emerging Infect. Dis. 7:277-281). For example, urinary tract infection (UTI) is the most common hospital-acquired infection, accounting for up to 40% of all nosocomial infections. The majority of cases of UTIs are associated with the use of urinary catheters, including trans-urethral folcy, suprapubic, and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTIs continue to pose a major problem. For instance, it is estimated that almost one-quarter of hospitalized spinal cord-injured patients develop symptomatic UTIs during their hospital course. Gram-negative bacilli account for almost 60-70%, Enterococci for about 25%, and *Candida* species for about 10% of cases of catheter-associated UTI.

Furthermore, indwelling medical devices including vascular catheters are becoming essential in the management of hospitalized patients by providing venous access. The benefit derived from these catheters as well as other types of medical devices such as peritoneal catheters, cardiovascular devices, orthopedic implants, and other prosthetic devices is often offset by infectious complications. The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. Fungi also form biofilms of clinical significance. *Candida albicans*, a fungal agent, accounts for 10-15% of catheter infections.

Bacteria and fungi growing in biofilms exhibit increased resistance to antimicrobial agents and are nearly impossible to eradicate using known techniques. The present invention teaches applications of an antibiofilm enzyme DispersinB™-based antimicrobial composition in devices, methods for preparing such devices, and methods of treating wounds and oral infections.

SUMMARY OF THE INVENTION

In one embodiment, the present invention provides a composition for preventing and/or inhibiting growth or proliferation of biofilm-embedded microorganisms comprising: (a) a first compound comprising DispersinB™, an active fragment or variant thereof that disperses a biofilm; and (b) a second compound comprising an antimicrobial agent active against bacteria or fungi.

In an embodiment, DspB is in a concentration of about 5 to about 500 µg/ml. In another embodiment, DspB is in a concentration of about 10 to about 250 µg/ml. In another embodiment, DispersinB™ is in a concentration of about 25 ng/ml to about 100 µg/ml.

In another embodiment, an antimicrobial agent can include triclosan, antibiotics (such as rifampicin, cefamandole nafate and ciprofloxacin), nitrofurazone, bismuth-thiols [such as bismuth ethanedithiol (BisEDT)], chitosan, epigallocatechin gallate (EGCG), sodium usnate, antineoplastic agents (such as 5-fluorouracil), detergents (such as SDS, benzalkonium chloride), chlorhexidine, chelating agents (such as EDTA), silver compounds, bacteriophage, antimicrobial enzymes (such as glucose oxidase and lactoperoxidase), sugar alcohols (such as xylitol), maleimides [such as N,N-(1,2 phenylene) dimaleimide (oPDM) and N-(1-pyrenyl) maleimide (PyrM)], cadexomer iodine, methylene blue, gentian violet, or medium chain dextrans (such as honey).

In a further embodiment, an antimicrobial agent can include triclosan, and can be in a concentration of about 0.1 µg/ml to about 50 mg/ml. In another embodiment, the concentration is about 0.2 µg/ml to about 25 mg/ml and in a still further embodiment, the concentration is about 0.325 µg/ml to about 10 mg/ml.

In yet another embodiment, an antimicrobial agent can include, but is not limited to, (i) rifampicin in a concentration of about 0.1 to about 1000 µg/ml, preferably about 1 to about 100, and more preferably about 10 to about 50 µg/ml; (ii) cefamandole nafate in a concentration of about 0.01 to about 10 µg/ml, preferably about 0.05 to about 5 µg/ml, and more 0.1 to about 2 µg/ml. (iii) nitrofurazone in a concentration of about 0.01 to about 1 mg/ml, preferably about 0.1 to about 1 mg/ml, and more preferably about 0.5 to about 1 mg/ml; (iv) bismuth ethanedithiol (BisEDT) in a concentration of about 0.01 to about 5 mM, preferably about 0.1 to about 2 mM, and more preferably about 1 mM, (v) ciprofloxacin in a concentration of about 0.01 to about 1.0 mg/ml; preferably about 0.05 to about 0.5 mg/ml and more preferably about 0.1 mg/ml; (vi) epigallocatechin gallate in a concentration of about 10 to about 100 µg/ml, preferably about 25 to about 50 µg/ml, or more preferably about 50 µg/ml; (vii) sodium usnate in a concentration of about 10 to about 750 µg/ml, preferably about 100 to about 500 µg/ml or more preferably 200 to about 400 µg/ml; (vii) ovotransferrin in a concentration of about 10 to about 1000 mg/ml, preferably about 25 to about 500 mg/ml or more preferably about 50 to about 200 mg/ml; (ix) sodium doceyl sulfate in a concentration of about 0.01 to about 100 mg/ml, more preferably about 0.05 mg/ml to about 50 mg/ml and more preferably about 0.1 mg/ml to about 10 mg/ml; (x) 5-fluorouracil in a concentration of about 1 to about 1000 µg/ml, preferably about 10 to about 500 µg/ml and more preferably about 25 to 100 µg/ml; (xi) chlorhexidine in a concentration of about 0.01 µg/ml to about 100 µg/ml, preferably about 0.1 µg/ml to about 10 µg/ml, and more preferably about 1 µg/ml to about 5/g/ml; (xii) benzalkonium chloride 0.01 µg/ml to about 100 µg/ml, preferably about 0.1 µg/ml to about 10 µg/ml, and more preferably about 1 µg/ml to about 5 µg/ml; (xiii) EDTA in a concentration of about 1 to about 1000 µg/ml, preferably about 10 to about 100 µg/ml and more preferably about 25 to about 50 µg/ml; or (xv) silver nanopowder in a concentration of 0.01 µg/ml to about 100 µg/ml, preferably about 0.1 µg/ml to about 10 µg/ml, and more preferably about 1 µg/ml to about 5 µg/ml.

An embodiment of the invention includes a method of inhibiting biofilm-embedded microorganisms comprising administering an effective amount of DispersinB™, an active fragment, or variant thereof that disperses a biofilm; and an effective amount of an antimicrobial agent or a mixture of an antimicrobial agent.

In another embodiment, the DispersinB™, an active fragment, or variant thereof is administered prior to administration of the antimicrobial agent and the antimicrobial agent is sodium doceyl sulfate, chlorhexidine, or benzalkonium chloride.

An embodiment of the invention includes a method of treating an infection by administering a composition comprising (a) DispersinB™, a DispersinB™ fragment, or variant thereof; and (b) an antimicrobial agent or a mixture of an antimicrobial agent.

In yet another embodiment, a DispersinB™-based antimicrobial composition can treat various kinds of wounds, including, but not limited to, cutaneous abscess, surgical wounds, sutured lacerations, contaminated lacerations, burn wounds such as partial and full thickness burns, decubitus ulcers, stasis ulcers, leg ulcers, foot ulcers, venous ulcers, diabetic ulcers, ischemic ulcers, and pressure ulcers.

In another embodiment, a DispersinB™-based antimicrobial composition can treat an oral infection. Oral infections include microorganisms in the subgingival and supragingival plaque. Subgingival plaque comprising microorganisms can cause periodontal disease. The compositions of the present invention can be used in the treatment of periodontal disease. The compositions of the present invention can be used in the treatment of localized juvenile periodontitis.

Biofilm microorganisms can be bacteria, such as gram-negative *Escherichia coli*, *Proteus mirabilis*, *Klebsiella pneumoniae*, *Bacteroides* spp., *Porphyromonas* spp., *Prevotella* spp., *Fusobacterium nucleatum*, *Aggregatibacter actinomycetemcomitans* (formerly *Actinobacillus actinomycetemcomitans*), *Treponema denticola*, or *Pseudomonas aeruginosa*, and gram-positive *Enterococcus faecalis*, *Enterococcus cloacae*, Vancomycin Resistant Enterococci (VRE), *Streptococcus* spp. *Peptostreptococcus* spp., *Staphylococcus epidermidis*, or *Staphylococcus aureus*. Furthermore, a wound-associated microorganism can be fungi, such as *Candida albicans*.

One embodiment of the present invention includes providing methods of using a DispersinB™-based composition or compositions in wound care devices such as non-resorbable gauze/sponge dressing, hydrophilic wound dressing, occlusive wound dressing, hydrogel wound, and burn dressing. The present invention also includes use of a spray-applicator containing a DispersinB™-based antimicrobial composition as a wound care device. Another embodiment of the invention includes a wound care device comprising a DispersinB™ based composition or compositions.

An additional aspect of the present invention includes wound care ointments, gels, and lotions comprising DispersinB™ and an antimicrobial agent. An embodiment of the present invention also includes wound care sutures coated with DispersinB™ and an antimicrobial agent.

Furthermore, a composition can comprise binders, wetting agents, odor absorbing agents, levelling agents, adherents, thickeners, and the like. Other additives may be present on and/or within a fabric of bandage including antistatic agents, optical brightening compounds, opacifiers (e.g., titanium dioxide), nucleating agents, antioxidants, UV stabilizers, fillers, permanent press finishes, softeners, lubricants, curing accelerators, adhesives, and the like.

In another embodiment, the present invention includes wound gel compositions for: (a) DispersinB™ antimicrobial wound gel with a viscosity improving agent; and (b) Triclosan-DispersinB™ antimicrobial wound gel with a viscosity improving agent. A DispersinB™ or Triclosan-DispersinB™ wound gel can include DispersinB™, an active fragment or variant thereof.

In another embodiment, an antimicrobial agent can include, but is not limited to, triclosan, antibiotics (such as rifampicin, cefamandole nafate and ciprofloxacin) nitrofurazone, bismuth-thiols [such as bismuth ethanedithiol (BisEDT)], chitosan, Epigallocatechin gallate (EGCG), sodium usnate, antineoplastic agents (such as 5-fluorouracil), detergents (such as SDS, benzalkonium chloride), chlorhexidine, chelating agents (such as EDTA), silver compounds, bacteriophage, antimicrobial enzymes (such as glucose oxidase and lactoperoxidase), sugar alcohols (such as xylitol), maleimides [such as N,N-(1,2 phenylene)dimaleimide (oPDM) and N-(1-pyrenyl) maleimide (PyrM)], cadexomer iodine, methylene blue, gentian violet, medium chain dextrans (such as honey), and mixtures thereof can be used in combination with DispersinB™.

In a further embodiment, a Triclosan-DispersinB™ wound gel comprises of about 1 to about 10% triclosan, preferably of about 5 to about 10% triclosan and more preferably, about 1% triclosan. In a further embodiment, a DispersinB™ wound gel and a Triclosan-DispersinB™ wound gel can optionally further comprise a gelling agent and/or a viscosity increasing agent.

Triclosan-DispersinB™ wound gel can be prepared in polyethylene glycol (PEG)/ethanol. PEG of different molecular weights ranging from about 200 to about 511,000 can be used in a gel formulation. In an embodiment, a Triclosan-DispersinB™ wound gel is prepared in 10% PEG-400/10% ethanol.

In a further embodiment, gelling agents in a wound gel include, but are not limited to, gums, polysaccharides, alginates, synthetic polymeric compounds, natural polymeric compounds, and mixtures thereof.

DispersinB™-based antimicrobial wound gels of the present invention can be used to inhibit the proliferation of biofilm-embedded gram-negative and gram-positive bacteria, which include, but are not limited to, *Escherichia coli, Proteus mirabilis, Klebsiella pneumoniae, Pseudomonas aeruginosa, Klebsiella oxytoca, Providentia sturtii, Serratia marcescens, Enterococcus faecalis*, Vancomycin Resistant Enterococci (VRE), *Peptostreptococcus* spp., *Corynebacterium* spp., *Clostridium* spp., *Bacteriodes* spp., *Prevotella* spp., *Streptococcus pyogenes, Streptococcus viridans, Micrococcus* spp., Beta-hemolytic *streptococcus* (group C), Beta-hemolytic *streptococcus* (group B), *Bacillus* spp., *Porphyromonas* spp., *Enterobacter cloacae, S. epidermidis, S. aureus, Staphylococcus agalactiae*, and *Staphylococcus saprophyticus*.

Additionally, DispersinB™ based antimicrobial compositions of the invention can also be used to inhibit proliferation of biofilm-embedded fungi, such as *Candida albicans, Candida parapsilosis*, and *Candida utilis*.

In one embodiment, a DispersinB™-based antimicrobial wound gel can be used for treating wounds including, but is not limited to, a cutaneous abscess, surgical wound, sutured laceration, contaminated laceration, blister wound, soft tissue wound, partial thickness burn, full thickness burn, decubitus ulcer, stasis ulcer, foot ulcer, venous ulcer, diabetic ulcer, ischemic ulcer, pressure ulcer, or combinations thereof.

Another embodiment, the present invention provides a method of preparing a device comprising treating at least one surface of the device with a composition as herein described. For example, the composition can be incorporated into polymers, wherein said polymers are used to form the device. Another aspect of the present invention is a method of preparing a device comprising coating the composition as herein described onto the inner and/or outer surface of a device.

In another embodiment, the DispersinB™ is about 0.1 to about 500 μg/ml of the composition, preferably about 1 to about 350 μg/ml of the composition or more preferably about 10 to about 100 μg/ml of the composition. In yet another embodiment, the antimicrobial agent is triclosan, rifampicin, cefamandole nafate, nitrofurazone, ciprofloxacin, minocycline, gentamycin, silver compounds, chlorhexidine, 5-fluorouracil or a bisphosphonate, preferably rifampicin, cefamandole nafate, nitrofurazone, or triclosan, more preferably triclosan. In one embodiment, the triclosan is in a concentration of about 0.01 to about 100 mg/ml of the composition, preferably about 0.1 to about 100 mg/ml of the composition or more preferably about 1 to about 100 mg/ml of the composition. In another embodiment, the antibacterial agent is rifampicin in a concentration of about 10 to about 1000 μg/ml of the composition, preferably about 100 to about 1000 μg/ml of the composition or more preferably about 10 to about 100 μg/ml of the composition. In another embodiment, the antibacterial agent is cefamandole nafate in a concentration of about 0.05 to 5 μg/ml of the composition, preferably about 0.5 to about 5 μg/ml of the composition, or more preferably, about 1 to about 5 μg/ml of the composition. In another embodiment, the antibacterial agent is nitrofurazone in a concentration of about 0.01 to about 1 mg/ml of the composition, preferably about 0.1 to about 1 mg/ml of the composition, and more preferably about 0.5 to about 1 mg/ml of the composition. In one embodiment of the present invention, the composition comprises effective amounts of DispersinB™ and triclosan. In another embodiment of the present invention, the composition comprises effective amounts of DispersinB™ and rifampicin. In yet another embodiment of the present invention, the composition comprises effective amounts of DispersinB™ and cefamandole nafate. In yet another embodiment of the present invention, the composition comprises effective amounts of DispersinB™ and nitrofurazone.

In one aspect of the present invention, the device is a medical device, such as a catheter, for example, an indwelling catheter such as a central venous catheter, a peripheral intravenous catheter, an arterial catheter, a peritoneal catheter, a haemodialysis catheter, an umbilical catheter, percutaneous nontunneled silicone catheter, a cuffed tunneled central venous catheter, an endotracheal tube, a subcutaneous central venous port, urinary catheter, a peritoneal catheter, a peripheral intravenous catheter or a central venous catheter.

In another embodiment of the present invention, the medical devices are catheters, pacemakers, prosthetic heart valves, prosthetic joints, voice prostheses, contact lenses, a shunt, heart valve, penile implant, small or temporary joint replacement, urinary dilator, cannula, elastomer, or intrauterine devices.

In another embodiment of the present invention, the device is a catheter lock, a needle, a Leur-Lok® connector, a needleless connector, a clamp, a forcep, a scissor, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopedic implant, or a saw.

Another embodiment of the present invention is a method of preparing a device comprising coating a composition herein described onto at least one surface of the device.

Another embodiment of the present invention is a device coated, impregnated, or treated with a composition as herein described, for example, a medical device such as a catheter, for example an indwelling catheter such as a central venous catheter, a peripheral intravenous catheter, an arterial catheter, a peritoneal catheter, a haemodialysis catheter, an umbilical catheter, percutaneous nontunneled silicone catheter, a cuffed tunneled central venous catheter, an endotracheal tube, a urinary catheter, a peritoneal catheter, a peripheral intravenous catheter and central venous catheter or a subcutaneous central venous port.

A device may also be catheters, pacemakers, prosthetic heart valves, prosthetic joints, voice prostheses, contact lenses, a stunt, heart valve, penile implant, small or temporary joint replacement, urinary dilator, cannula, elastomer, intrauterine devices, catheter lock, a needle, a Leur-Lok® connector, a needleless connector, a clamp, a forcep, a scissor, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopedic implant, or a saw.

Another embodiment of the present invention is a method of preventing device or catheter-related infection in a mammal, said method comprising coating, incorporating, or treating a device or catheter to be implanted with a composition as herein described. Another embodiment of the present invention is a method of preventing an infection caused by a device or catheter in a mammal, said method comprising coating, incorporating or treating the device or catheter with a composition as herein described.

Another embodiment of the present invention is the use of a composition as herein described in the preparation of a medical device for implantation in a mammal. In one embodiment, a medical device may be coated, incorporated, or treated with a composition. In another embodiment, the composition may prevent urinary tract infection. Another aspect of the present invention is the use wherein the composition prevents urinary or vascular infection.

In another embodiment, the present invention provides a composition for inhibiting biofilm-embedded microorganisms comprising: (a) DispersinB™, an active fragment or variant thereof that disperses a biofilm; and (b) a bacteriophage. The composition can comprise about $10^8$ bacteriophage. The bacteriophage can comprise more than one species of bacteriophage.

In another embodiment, the present invention provides a composition for inhibiting biofilm-embedded microorganisms comprising a recombinant bacteriophage, wherein the recombinant bacteriophage displays DispersinB™. The displayed DispersinB™ can be fused to a phage coat protein. The DispersinB™ can be fused to the major coat protein or the minor coat protein. In another embodiment, the present invention provides a fusion protein comprising at least a portion of a phage coat protein bonded to DispersinB™.

DETAILED DESCRIPTION

Definitions

Figure 1:
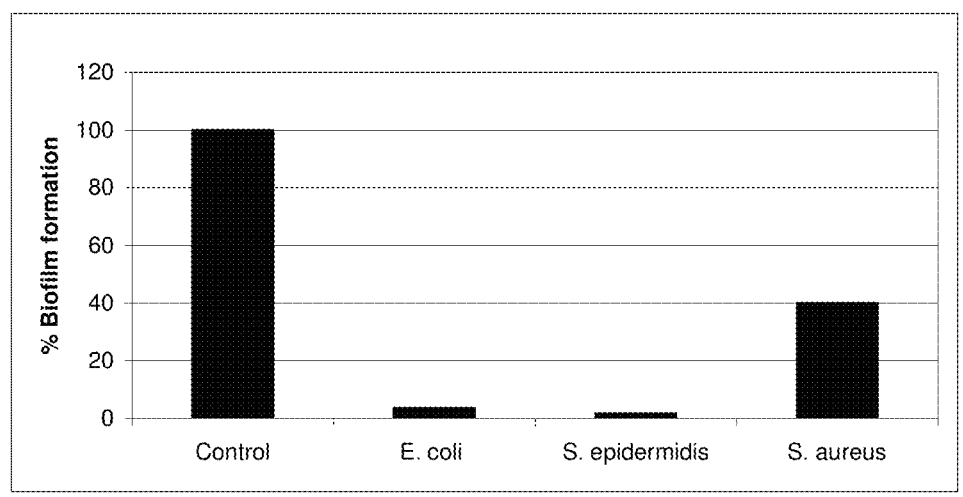
FIG. 1 is a bar graph showing the effect of DispersinB™ on *Escherichia coli*, *Staphylococcus epidermidis* and *Staphylococcus aureus* biofilm formation. All three bacterial strains were grown separately in a media without DispersinB™ as a negative control.

The term "active fragment" refers to smaller portions of the DispersinB™ polypeptide that retains the ability to disperse bacteria or fungi.

The term "antimicrobial" means a compound or a composition that kills or slows/stops the growth of microorganisms, including, but not limited to bacteria and yeasts, and but not including agents which specifically disperse bacteria or fungi. Some examples of antimicrobials are triclosan, rifampicin, or cefamandole nafate.

The term "biofilm embedded microorganisms" refers to any microorganism that forms a biofilm during colonization and proliferation on a surface, including, but not limited to, gram-positive bacteria (e.g., *Staphylococcus epidermidis*), gram-negative bacteria (e.g., *Pseudomonas aeruginosa*), and/or fungi (e.g., *Candida albicans*).

The term "biofilm formation" means the attachment of microorganisms to surfaces and the subsequent development multiple layers of cells.

A "composition" refers to of this invention can comprise (a) DispersinB™, an active fragment or variant thereof that disperses a biofilm; and (b) an antimicrobial agent active against bacteria or fungi, optionally in combination with a physiologically acceptable carrier. The composition can further comprise an additional antimicrobial agent.

The term "detergent" is used to mean any substance that reduces the surface tension of water. A detergent may be a surface active agent that concentrates at oil-water interfaces, exerts emulsifying action and thereby aids in removing soils e.g., common sodium soaps of fatty acids. A detergent may be anionic, cationic, or monionic depending on their mode of chemical action. Detergents include linear alkyl sulfonates (LAS) often aided by "builders." A LAS is preferably an alkyl benzene sulfonate ABS that is readily decomposed by microorganisms (biodegradable). A LAS is generally a straight chain alkyl comprising 10 to carbon atoms. A detergent may be in a liquid or a solid form.

A "viscosity increasing agent", "viscosity improving agent" or "gelling agent" refers to agents that increase viscosity thereby making compositions, such as wound gels, thick and stable. Examples of a viscosity improving agents include, but are not limited to, natural products such as alginic acid, sodium alginate, potassium alginate, ammonium alginate, calcium alginate, agar, carrageenana, locust bean gum, pectin, gelatine, carboxymethyl cellulose (CMC), and chemically synthesized polymers, such as carbopol.

The term "disperse" or "disperse a biofilm" refers to individual bacterial or fungal cells detaching from a surface or detaching from a biofilm. The term "disperse" also refers to disaggregation of autoaggregating bacterial or fungal biofilm cells. "Disperses a biofilm" does not require all biofilm embedded microorganisms to detach, but rather a portion to detach from a surface or a biofilm.

The term "inhibition" or "inhibiting" refers to a decrease of biofilm associated microorganism formation and/or growth. The microorganisms can include bacteria (e.g., streptococci) or fungi (e.g., *Candida* spp.)

"Modulating detachment" as used herein, is meant to be inclusive of increases as well as decreases in bacterial or fungal biofilm detachment or release of bacterial or fungal cells from a biofilm. Further, "modulating detachment", is also meant to be inclusive of changes in the ability of the bacteria or fungal to attach as a biofilm. For example, as demonstrated herein, DispersinB™ modulates detachment of *S. epidermidis*, *Staphylococcus aureus* and *Escherichia coli* not only by promoting detachment but also by inhibiting the ability of the bacteria to attach to surfaces and form a biofilm.

The term "mammal" for purposes of treatment refers to any animal classified as a mammal, including humans, domestic, farm, sport and zoo animals, or pet animals, such as dogs, horses, cats, cattle, pigs, sheep, etc. Preferably, the mammal is human.

The term "therapeutically effective amount" refers to an amount of a composition of this invention effective to "alleviate" or "treat" a disease or disorder in a subject or mammal. A "therapeutically effective amount" as used herein includes a prophylactic amount, for example, an amount effective for preventing or protecting against infectious diseases, and symptoms thereof, and amounts effective for alleviating or treating infectious diseases, related diseases, and symptoms thereof. A "therapeutically effective amount" as used herein also includes an amount that is bacteriostatic or bacteriocidal, for example, an amount effective for inhibiting growth of biofilm associated bacteria or killing biofilm associated bacteria, respectively. A "therapeutically effective amount" as used herein also includes an amount that is fungistatic or fungicidal, for example, an amount effective for inhibiting further growth of biofilm associated fungi or killing biofilm associated fungi, respectively. By administering a DispersinB™ compound suitable for use in methods of the invention concurrently with an antimicrobial compound, the therapeutic antimicrobial compound may be administered in a dosage amount that is less than the dosage amount required when the therapeutic antimicrobial compound is administered as a sole active ingredient. By administering lower dosage amounts of the active ingredient, the side effects associated therewith should accordingly be reduced.

The term "treatment", "treating", or "alleviating" refers to an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

A chronic wound defined herein is a wound that fails to progress through an orderly and timely sequence of repair or a wound that does not respond to treatment and/or the demands of treatment are beyond the patient's physical health, tolerance or stamina. Many wounds that are first considered to be acute wounds ultimately become chronic wounds due to factors still not well understood. One significant factor is the transition of planktonic bacteria within the wound to form a biofilm.

In the context of wound treatment, "biofilm disruption" or "inhibition of biofilm reconstitution" refers to biofilm clearance from a chronic or acute wound, or to inhibit reconstitution of a biofilm mass from remnants remaining after debridement and thereby promote healing of a wound.

A "wild type" or "reference" sequence or the sequence of a "wild type" or "reference" protein/polypeptide, such as a coat protein, or a CDR or variable domain of a source antibody, maybe the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

A "variant" of a polypeptide refers to a polypeptide that contains an amino acid sequence that differs from a wild type or reference sequence. A variant polypeptide can differ from the wild type or reference sequence due to a deletion, insertion, or substitution of a nucleotide(s) relative to said reference or wild type nucleotide sequence. The reference or wild type sequence can be a full-length native polypeptide sequence or any other fragment of a full-length polypeptide sequence. A polypeptide variant generally has at least about 80% amino acid sequence identity with the reference sequence, but may include 85% amino acid sequence identity with the reference sequence, 86% amino acid sequence identity with the reference sequence, 87% amino acid sequence identity with the reference sequence, 88% amino acid sequence identity with the reference sequence, 89% amino acid sequence identity with the reference sequence, 90% amino acid sequence identity with the reference sequence, 91% amino acid sequence identity with the reference sequence, 92% amino acid sequence identity with the reference sequence, 93% amino acid sequence identity with the reference sequence, 94% amino acid sequence identity with the reference sequence, 95% amino acid sequence identity with the reference sequence, 96% amino acid sequence identity with the reference sequence, 97% amino acid sequence identity with the reference sequence, 98% amino acid sequence identity with the reference sequence, 98.5% amino acid sequence identity with the reference sequence, 99% amino acid sequence identity with the reference sequence, or 99.5% amino acid sequence identity with the reference sequence.

"Percent (%) nucleic acid sequence identity" is defined as the percentage of nucleotides in a candidate sequence that are identical with the nucleotides in a reference polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNAS-TAR) software. Appropriate parameters for measuring alignment, including any algorithms needed to achieve maximal alignment over the full-length of the sequences being compared can be determined by known methods.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence 1) is calculated as follows:

100 times the fraction W/Z, where W is the number of nucleotides scored as identical matches by the sequence alignment program in that program's alignment of C and D, and where Z is the total number of nucleotides in D. Where the length of nucleic acid sequence C is not equal to the length of nucleic acid sequence D, the % nucleic acid sequence identity of C to D will not equal the % nucleic acid sequence identity of D to C.

The term "protein" has an amino acid sequence that is longer than a peptide. A "peptide" contains 2 to about 50 amino acid residues. The term "polypeptide" includes proteins and peptides. Examples of proteins include, but are not limited to, antibodies, enzymes, lectins and receptors; lipoproteins and lipopolypeptides; and glycoproteins and glycopolypeptides.

A "phage coat protein" comprises at least a portion of the surface of the phage virus particle. Functionally, a coat protein is any protein that associates with a virus particle during the viral assembly process in a host cell and remains associated with the assembled virus until infection. A major coat protein is that which principally comprises the coat and is present in 10 copies or more copies/particle; a minor coat protein is less abundant. A phage coat protein may be a variant coat protein. Some variant coat proteins have improved display of the fused polypeptide.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "phage display" is a technique by which polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage (Wells & Lowman, *Curr. Opin. Struct. Biol.*, 3:355-362 (1992)).

"PCR" refers to the technique in which minute amounts of a specific piece of nucleic acid, RNA and/or DNA, are amplified as described in U.S. Pat. No. 4,683,195. PCR can be used to amplify specific RNA sequences, specific DNA sequences from total genomic DNA, and cDNA transcribed from total cellular RNA, bacteriophage or plasmid sequences, etc.

sion of *A. actinomycetemcomitans*. This polypeptide is referred to as DispersinB™. The first 20 amino acids are a signal peptide, and amino acids 21-381 are the mature polypeptide. The mature DispersinB™ polypeptide has the following sequence (SEQ ID NO:11; Accession No. AY228551.1):

```
  1 nccvkgnsiy pqktstkqtg lmldiarhfy speviksfid tislsggnfl hlhfsdheny
 61 aieshllnqr aenavqgkdg iyinpytgkp flsyrqlddi kayakakgie lipeldspnh
121 mtaifklvqk drgvkylqgl ksrqvddeid itnadsitfm qslmsevidi fgdtsqhfhi
181 ggdefgysve snhefityan klsyflekkg lktrmwndgl ikntfeqinp nieitywsyd
241 gdtqdkneaa errdmrvslp ellakgftvl nynsyylyiv pkasptfsqd aafaakdvik
301 nwdlgvwdgr ntknrvqnth eiagaalsiw gedakaikde tiqkntksll eavihktngd
361 e
```

DNA is "purified" when the DNA is separated from non-nucleic acid impurities. The impurities may be polar, non-polar, ionic, etc.

The term "nucleic acid" as used herein includes (but is not limited to) unmodified RNA or DNA or modified RNA or DNA. Thus, by nucleic acid it is meant to be inclusive of The closely related *Actinobacillus pleuropneumoniae* also encodes a DispersinB™, which is a 377 amino acid polypeptide that includes a signal peptide from amino acids 1 to 34. The *A. pleuropneumoniae* DispersinB™ has the following full polypeptide sequence (SEQ ID NO:12; Accession No. AY618481.1; AAT46094.1 GI:48727581):

```
  1 mkkaitlftl lcavllsfst atyanamdlp kkesgltldi arrfytvdti kqfidtihqa
 61 ggtfihlhfs dhenyaless yleqreenat ekngtyfnpk tnkpfltykq lneiiyyake
121 rnieivpevd spnhmtaifd lltlkhgkey vkglkspyia eeidinnpea veviktlige
181 viyifghssr hfhiggdefs yavennhefi ryvntlndfi nskglitrvw ndglthnnls
241 elknieity wsydgdaqak ediqyrreir adlpellang fkvlnynsyy lyfvpksgsn
301 ihndgkyaae dvlnnwtlgk wdgknssnhv qntqniigss lsiwgerssa lneqtiqqas
361 knllkaviqk tndpksh
``` single- and double-stranded DNA, DNA that is a mixture of single- and double-stranded regions, single- and double-stranded RNA, and RNA that is a mixture of single- and double-stranded regions, hybrid molecules containing DNA and RNA that may be single-stranded or, more typically, double-stranded or a mixture of single- and double-stranded regions. Further, the DNA or RNA sequences of the present invention may comprise a modified backbone and/or modified bases. A variety of modifications to DNA and RNA are known in the art for multiple useful purposes. The term "nucleic acid" as it is employed herein embraces such chemically, enzymatically or metabolically modified forms of nucleic acids, as well as the chemical forms of DNA and RNA characteristic of viruses and cells, including simple and complex cells.

By the term "allelic variant" as used herein it is meant one of two or more alternative naturally occurring forms of a gene, each of which comprises a unique nucleic acid sequence. Allelic variants encompassed by the present invention encode proteins with similar or identical enzymatic activities.

DispersinB™

Biofilm-embedded *Aggregatibacter* (formerly *Actinobacillus*) *actinomycetemcomitans* can release individual cells into liquid medium. These detached cells can attach to the surface of a culture apparatus and start a new colony. The dspB gene encodes a 381 amino acid soluble β-N-acetylglucosaminidase that is responsible for the detachment/disper- Embodiments of the invention also include active fragments and variants of SEQ ID No:11 and SEQ ID No:12. DispersinB™ active fragments and variants only include those fragments and variants that retain an ability to disperse a bacterial or fungal cell from a biofilm.

A substrate for both DispersinB™ is a high-molecular weight hexosamine-containing extracellular polysaccharide adhesin encoded in the pgaABCD locus and pgaCD in *A. actinomycetemcomitans* and *A. pleuropneumoniae*, respectively (Kaplan et al., 2004, *J. Bacteriol.* 186:8213-8220). These polysaccharide adhesins are a component of the *Aggregatibacter* biofilm. A PGA component of the biofilm functions as a protective barrier for cells of a biofilm. *Aggregatibacter* PGA is structurally and functionally similar to *E. coli* PGA and *S. epidermidis* PTA, both polysaccharides comprising N-acetyl-D-glucosamine residues in a (1,6) linkage (Kaplan et al., 2004). Thus, embodiments of this invention can be used to detach bacterial cells other than *A. actinomycetemcomitans* or *A. pleuropneumoniae*.

Nucleic acid sequences encoding orthologs of DispersinB™ protein have been identified in *A. lingniersii* strain 19393, *A. actinomycetemcomitans* strain IDH 781, *Haemophilus aphrophilus* strain NJ8700 and *A. pleuropneumoniae* strain IA5 and are depicted in SEQ ID No: 3, 5, 7, and 9, respectively. Accordingly, preferred isolated nucleic acid sequences of the present invention comprise SEQ ID No. 1, 3, 5, 7 or 9.

Also included within the present invention are allelic variants of the exemplified DispersinB™ nucleic acid sequence for SEQ ID No: 1, 3, 5, 7, or 9 encoding proteins with similar enzymatic activities to DispersinB™ and nucleic acid sequences with substantial percent sequence identity to the exemplified DispersinB™ nucleic acid sequences of SEQ ID NO: 1, 3, 5, 7 or 9 encoding proteins with similar enzymatic activities There are similarities between the amino acid sequence of DispersinB™ and these orthologs and the consensus sequence or the Family 20 glycosyl hydrolase. More specifically, amino acid residues 40 to 297 of the predicted DispersinB™ protein sequence are homologous to the catalytic domain of the family 20 glycosyl hydrolases (NCBI Conserved Domain Database accession Number pfam00728). This family of enzymes includes bacterial chitinases, chitobiases and lacto-N-biosidases (Sano et al. J. Biol. Chem. 1993 268:18560-18566; Tews et al. Gene 1996, 170:63-67; Tsujibo et al. Biochim. Biophys. Acta 1998, 1425:437-440.), and eukaryotic hexosaminidases (Graham et al. J. Biol. Chem. 1988, 263:16823-16829). A protein related to *A. actinomycetemcomitans* DispersinB™ is lacto-N-biosidase of *Lactococcus lactis* (GenBank accession no. AAK05592), which displays 28% identity over 281 amino acid residues not counting gaps and terminal extensions.

Similarity between DispersinB™ and lacto-N-biocidases is high in the regions surrounding Arg47 and the acidic amino acid pair Asp202 and Glu203. These residues have been shown to participate in substrate binding and catalysis in other family 20 glycosyl hydrolases (Mark et al. J. Biol. Chem. 2001, 276:10330-10337; Mark et al. J. Biol. Chem. 1998, 273:19618-19624; Prag et al. J. Mol. Biol. 2000, 300: 611-617). The C-terminal half of DispersinB™ contained three Trp residues that were conserved in *L. lactis* lacto-N-biosidase (positions 236, 279, and 353). Multiple Trp residues are present in the C-terminal regions of the catalytic domains of all family 20 glycosyl hydrolases (Graham et al. J. Biol. Chem. 1988, 263:16823-16829; Tews et al. Gene 1996, 170:63-67). These Trp residues line the part of the substrate binding pocket that is complementary to the hydrophobic surfaces of the hexosamine sugar ring (Tews et al. Nature Struct. Biol. 1996, 3638-648). It is expected that mutation of amino acids in these regions of DispersinB™ and its orthologs will alter enzymatic activity.

In a preferred embodiment an isolated amino acid sequence of the present invention comprises SEQ ID NO: 2, 4, 6, 8, 10, 11 or 12 or an active fragment or variants thereof. Preferred active fragments are those comprising a portion of the amino acid sequence of SEQ ID NO: 2, 4, 6, 8, 10, 11 or 12 with similarities to the consensus sequence of the family 20 glycosyl hydrolase.

"Active variants or "functionally equivalent variants" as used herein are polypeptide sequences structurally different from the DispersinB™ protein, but having no significant functional difference from the protein. For example, when orthologous polypeptide sequences from various strains of *A. actinomycetemcomitans* are aligned, divergence in amino acid sequence is observed, usually 0 to 10 percent (Kaplan et al. Oral Microbiol. Immunol. December 2002, 17:354-359; Kaplan et al. Infect. Immun. 2001, 69:5375-5384). Proteins displaying this amount of divergence are considered functionally equivalent variants because of the fact that mixing of genetic alleles that encode these variants is often observed in populations (Kaplan et al. Oral Microbol. Immunol. December 2002 17:354-359). The DispersinB™ sequence from *A. actinomycetemcomitans* strain IDH781 (SEQ ID NO:6), therefore, is expected to be a functionally equivalent or active variant of SEQ ID NO:2, and is included in the scope of the present invention. Similarly, DispersinB™ sequences from other strains of *A. actinomycetemcomitans*, such as those that exhibit different serotypes, restriction fragment length polymorphism genotypes, 16S ribosomal RNA genotypes, or arbitrarily-primed PCR genotypes that are commonly observed among phylogenetically diverse strains isolated from different subjects (Kaplan et al. J. Clin. Microbiol. 2002 40:1181-1187; Kaplan et al., Oral Microbial. Immunol. December 2002 17:354-359), are also expected to be functionally equivalent or active variants of SEQ ID NO:2, and are included in the scope of the present invention.

Similarly, orthologous proteins from phylogenetically diverse species of bacteria are usually functionally equivalent or active variants, as evidenced by the fact that a common method for cloning genes of interest into plasmids is to screen a plasmid library for plasmids that complement a genetic mutation in a different species of bacteria (Kaplan et al. J. Mol. Biol. 1985 183:327-340). This is especially true of bacterial enzymes. Orthologous enzymes of different bacterial species can exhibit up to 50% divergence or greater, yet still utilize the identical substrate, catalyze the same chemical reaction, and produce the same product. This sequence divergence results from genetic drift coupled with fixation of selected genetic changes in the population. The genetic changes that are selected and fixed are those that alter characteristics of the enzyme other than substrate, reaction, and product, as for example, reaction rate, pH optimum, temperature optimum, level of expression, and interactions with other enzymes, such that these genetic changes confer upon a bacterial cell a selective advantage in its environment. Since *A. actinomycetemcomitans* is genetically closely related to *A. pleuropneumoniae* (Dewhirst et al. J. Bacterial. 1992 174: 2002-2013) and produces a biofilm similar to that produced by *A. actinomycetemcomitans*, which detaches upon contact with *A. actinomycetemcomitans* DispersinB™, it is expected that the *A. pleuropmoniae* DispersinB™ homologue identified in SEQ ID NO:10 is a functionally equivalent or active variant of SEQ ID NO:2, and is included in, the scope of the present invention, Similarly, since *Actinobacillus lignieresii* is genetically closely related to *Actinobacillus pleuropneumoniae* (Dewhirst et al. J. Bacteriol. 1992 174:2002-2013) and *Haemophilus aphrophilus* is genetically closely related to *A. actinomycetemcomitans* (Dewhirst et al. J. Bacteriol. 1992 174:2002-2013; Kaplan et al. J. Clin. Microbiol. 2002 40:1181-1187), and since both *A. lignieresii* and *Haemophilus aphrophilus* produce biofilms similar to that produced by *A. actinomycetemcomitans*, it is expected that the *Actinobacillus lignieresii* and *Haemophilus aphrophilus* DispersinB™ homologues identified in SEQ TD NO:4 and SEQ ID NO:5, respectively, are functionally equivalent or active variants of SEQ ID NO:2, and are included in the scope of the present invention.

The above mentioned examples demonstrate functionally equivalent or active variants of *A. actinomycetemcomitans* DispersinB™ that occur in nature. As will be understood by those of skill in the art upon reading this disclosure, however, artificially produced genes that encode functionally equivalent or active variants of *A. actinomycetemcomitans* DispersinB™ can also be produced routinely in accordance with the teachings herein using various well known genetic engineering techniques. For example, a genetically engineered dispersin enzyme that lacks 20 N-terminal amino acid residues, and also contained a 32 amino acid residue C-terminal tail, which it functionally equivalent to the natural DispersinB™ enzyme has been produced. It has also been shown that the methionine residue at the N-terminus of this genetically engineered DispersinB™ enzyme, when expressed in *E. coli*, was removed by the action of methionine aminopeptidase, yet the absence of the methionine did not affect enzyme activity. It has also been shown that cleavage of the C-terminal 28 amino acid residues from this genetically engineered DispersinB™ enzyme has no affect on enzyme activity. These examples demonstrate that artificial genes can be produced that encode functionally equivalent variants of *A. actinomycetemcomitans* DispersinB™. These artificially produced functionally equivalent variants of *A. actinomycetemcomitans* DispersinB™ are included in the scope of the present invention.

The above mentioned examples demonstrate genetically-engineered, functionally equivalent variants of *A. actinomycetemcomitans* DispersinB™ that contain either a deletion of amino acid residues at the N-terminus of the protein, or the fusion of an additional polypeptide at the C-terminus of the protein. It is expected that other genetically-engineered alterations, such as the fusion of an additional polypeptide at the N-terminus at the protein, a deletion of amino acid residues at the C-terminus of the protein, internal deletions and insertions of amino acid residues, and amino acid substitutions, would also result in functionally equivalent variants of *A. actinomycetemcomitans* DispersinB™. Information about which deletions, insertions, and amino acid substitutions would produce functionally equivalent variants of *A. actinomycetemcomitans* DispersinB™ can be obtained from amino acid sequence alignments, and from commonly available computer software that predicts polypeptide secondary structures based on both primary amino acid sequences and on amino acid sequence alignments with homologous proteins having known three-dimensional structures. *A. actinomycetemcomitans* DispersinB™, for example, is a member of the family 20 glycosyl hydrolases, a family that includes several well-studied enzymes, and a family represented by numerous homologous primary amino acid sequences in the public databases. In some cases, three-dimensional structures of family 20 glycosyl hydrolases are known (Tews et al. Nature Struct. Biol. 1996 3:638-648).

All family 20 glycosyl hydrolases exhibit a $(\alpha\beta)_8$-barrel motif (also known as a TIM-barrel motif; Tews et al., Nature Struct. Biol. 1996 3:638-648; Prag et al. J. Mol. Biol. 2000 300:611-617), which is by far the most common enzyme fold in the Protein Data Bank (PDB) database of known protein structures. It is estimated that 10% of all known enzymes have this domain (Wierenge, R. K., FEBS Lett. 2001 492:193-198). The $(\alpha\beta)_8$-barrel motif is seen in many different enzyme families, catalyzing completely unrelated reactions. The availability of numerous homologous primary amino acid sequences, combined with the availability of the three-dimensional structures of several *A. actinomycetemcomitans* DispersinB™ homologues, forms the basis of these sequence alignments and secondary structure predictions. For example, the $(\alpha\beta)_8$-barrel motif consists of eight α-helices and eight β-strands such that eight parallel β-strands form a barrel on the inside of the protein, which are covered by eight α-helices on the outside of the protein. Based on the above mentioned protein sequence alignments and structural predictions, it is expected that the eight β-strands in *A. actinomycetemcomitans* DispersinB™ comprise the amino acid residues surrounding positions 41-44, 69-81, 130-134, 169-171, 189-200, 253-256, 288-300, and 348-360 of SEQ ID NO:2. Any alteration in the amino acid sequence that disrupts the β-strand architecture of these eight regions would be expected to result in a decrease in enzyme activity because of a concomitant disruption in the three-dimensional structure of the $(\alpha\beta)_8$-barrel of the enzyme. Similarly, based on the above mentioned protein sequence alignments and structural predictions, it is expected that the eight α-helices in *A. actinomycetemcomitans* DispersinB™ comprise the amino acid residues surrounding positions 52-63, 89-93, 143-149, 176-183, 214-228 269-284, 309-321, and 361-374 of SEQ ID NO:2. Any alteration in the amino acid sequence that disrupts the β-helical architecture of these eight regions would be expected to result in a decrease in enzyme activity because of a concomitant disruption in the three-dimensional structure of $(\alpha\beta)_8$-barrel of the enzyme.

Similarly, because the α-strands consist or four inward pointing side chains (pointing into the $(\alpha\beta)_8$-barrel) and four outward pointing side chains (pointing towards the α-helices), it is expected that alterations in the inward-pointing amino acid residues will reduce enzyme activity because of concomitant alterations to the substrate binding pocket inside the $(\alpha\beta)_8$-barrel, and that alterations in the outward-pointing amino acid residues will reduce enzyme activity when they interfere with the interactions, between the β-strands and the α-helices. Similarly, the active site of family 20 glycosyl hydrolases is always located at the C-terminal end of the eight parallel β-strands of the barrel. It is expected that alterations in the homologous region, of *A. actinomycetemcomitans* DispersinB™ will affect enzyme activity. Similarly, it is predicted that the introduction of insertions and deletions into the regions between the α-helices and the β-strands, namely in positions 45-51, 64-68, 82-88, 94-129, 135-142, 150-168, 172-175, 182-188, 201-213, 229-252, 257-268, 285-287, 301-308, 322-347, and 351-360, in SEQ ID NO:2, will not effect enzyme activity. Similarly, it is expected that almost any alteration of residues 47 (Arginine), 203 (Aspartate) and 204 (Glutamate) will result in complete loss of enzyme activity, because these three residues have been shown to participate directly in substrate binding and catalysis in all family 20 glycosyl hydrolases (Mark et al. J. Biol. Chem. 1998 273: 19618-19624; Prag et al. J. Mol. Biol. 2000, 300:611-617; Mark et al. Biol. Chem. 2001 276:10330-10337). Similarly, it is expected that alteration of the three tryptophan residues at positions 236, 257 and 350, to any non-aromatic amino acid residue will result in a decrease in enzyme activity because these three tryptophan residues have been shown to line part of the substrate-binding pocket that is complementary to the hydrophobic surfaces of the substrate hexosamine sugar ring (Tews et al. Nature Struct. Biol. 1996 3:638-648). As a result of the locations of these essential amino acid residues in *A. actinomycetemcomitans* DispersinB™, it is predicted that no more than 46 amino acid residues can be deleted from the N-terminus, and no more that 31 amino acids can be deleted from the C-terminus, without loss of enzyme activity. All of those genetic alterations that result in functionally equivalent variants are included in the scope of the present invention.

Genes encoding functionally different variants of *A. actinomycetemcomitans* DispersinB™ can also be produced in accordance with the teachings of the instant application using well known genetic engineering techniques. For example, as mentioned above, it is expected that almost any alteration of residues 47 (Arginine), 203 (Aspartate) and 204 (Glutamate) in SEQ ID NO:2 will result in complete loss of enzyme activity. Alternatively, variants of *A. actinomycetemcomitans* DispersinB™ that exhibit characteristics that may be useful in a clinical setting could also be artificially produced. For example, the temperature optimum of *A. actinomycetemcomitans* DispersinB™ is 30° C. It may be desirable to produce a genetically-engineered variant of DispersinB™ that exhibits a temperature optimum of 37° C., thereby resulting in an increased effectiveness of the enzyme or decreased cost of treatment, such variants can be artificially produced by first creating random mutations in the *A. actinomycetemcomitans*

DispersinB™ gene sequence, for example by using UV light or a chemical mutagen like nitrosoguanidine and then screening large numbers of these random variants, for example in a quantitative 96-well microtiter plate assay (Kaplan et al. J. Bacteriol. 2003 185:4693-4698), for ones that exhibit higher temperature optima. An alternative method is to utilize directed evolution of sequences by DNA shuffling (Christians et al. Nature Biotechnol. 1999 17:259-264; Dichek at al. J. Lipid Res. 1993 34:1393-1340), combined with a high-throughput robotic screen based upon a quantitative 96-well microtiter plate assay (Kaplan et al. J. Bacteriol. 2003 18S:4693-4698) to identify variants with increased temperature optima. The aforementioned methods can also be used to produce variants of *A. actinomycetemcomitans* DispersinB™ that exhibit increased substantivity to biomaterials, increased pH optima, increased stability in aqueous solutions, increased reaction rate, increased stability upon desiccation, and other characteristics that could result in increased effectiveness of the enzyme or decreased cost of treatment. An alternative method that can be used to produce useful variants is site-directed mutagenesis. For example, it is expected that the eight α-helices of the $(\alpha\beta)_8$-barrel in *A. actinomycetemcomitans* DispersinB™ contain many amino acid residues that are exposed on the outer surface of the enzyme, and that altering the outward-pointing amino acid residues of the eight α-helices will alter the outer surface properties of the enzyme, thereby potentially increasing the substantivity of the enzyme for biomaterials without affecting enzyme activity. Accordingly, these outward painting amino acid residues can be systematically mutated, for example from polar residues to charged residues, and the resulting mutants screened to identify variants with increased substantivity to biomaterials. Functionally different variants of *A. actinomycetemcomitans* DispersinB™ that are intended to improve the clinical efficiency or cost effectiveness of the enzyme, when applied to detaching bacterial or fungal cells from biofilms, are included in the scope of the present invention.

Compositions

Antibiofilm enzyme-based antimicrobial compositions comprising DispersinB™ or an active fragment or variant thereof, and an antimicrobial agent, can inhibit biofilm formation as well as biofilm growth. In particular, a composition comprising DispersinB™ or an active fragment or variant thereof, and triclosan, a broad-spectrum antimicrobial has enhanced antibiofilm and antimicrobial activity. Such compounds are effective for inhibiting growth and proliferation of biofilm-embedded microorganisms, including both bacterial and fungal species. An enhanced antimicrobial activity of antimicrobials used in combination with DispersinB™ enzyme is evidenced by the low concentration of each compound required to inhibit bacterial growth effectively. In particular, it is possible to use small amounts of DispersinB™, or an active fragment or variant thereof, which are biologically acceptable, and a small amount of triclosan, which is biologically acceptable at lower concentrations.

It will be appreciated that DispersinB™ or active fragments or variants thereof and antimicrobial agents can be used together in the form of a single composition in one embodiment or together in the form of separate compositions for inhibiting growth and proliferation of biofilm-embedded microorganisms in another embodiment. In embodiments wherein separate compositions comprising DispersinB™ or an active fragment or variant thereof and antimicrobial agents are employed, the separate compositions can be used at the same time or sequentially. In a preferred embodiment, a composition comprising DispersinB™ or an active fragment or variant thereof is administered separately to a biofilm to be treated followed by separate administration of a composition comprising an antimicrobial agent for inhibiting growth and proliferation of biofilm-embedded microorganisms. In a further preferred embodiment, the composition comprising an antimicrobial agent, comprises sodium doceyl sulfate, benzalkonium chloride or chlorhexidine as the antimicrobial agent.

Accordingly, an embodiment of the present invention provides compositions for preventing growth and proliferation of biofilm embedded-microorganisms comprising: (a) DispersinB™, an active fragment, or variant thereof; and (b) triclosan.

Also, other antimicrobials including, but not limited to, triclosan, antibiotics (such as rifampicin, cefamandole nafate and ciprofloxacin) nitrofurazone, bismuth-thiols [such as bismuth ethanedithiol (BisEDT)], chitosan, epigallocatechin gallate (EGCG), sodium usnate, antineoplastic agents (such as 5-fluorouracil), detergents (such as sodium doceyl sulfate (SDS), benzalkonium chloride), chlorhexidine, chelating agents (such as EDTA), silver compounds, bacteriophage, antimicrobial enzymes (such as glucose oxidase and lactoperoxidase), sugar alcohols (such as xylitol), maleimides [such as N,N-(1,2 phenylene) dimaleimide (oPDM) and N-(1-pyrenyl)maleimide (PyrM)], cadexomer iodine, methylene blue, gentian violet, medium chain dextrans (such as honey), and mixtures thereof can be used in combination with DispersinB™.

An enhanced antimicrobial composition of the invention requires remarkably small amounts of active ingredients (compared to that used in the past) to be effective against the microbial growth and biofilm formation. A composition according to the invention may have properties that include those of separate compounds but go beyond them in efficacy and scope of application. Extremely low levels, and hence increased efficacy, of active compounds or ingredients, make embodiments of this invention very desirable and relatively economical to manufacture, although higher concentrations of these compounds can be used if it is desired for certain applications. A further advantage of using these compositions is the effectiveness for preventing growth of biofilm embedded bacteria and fungus, and in particular, bacterial and fungal species that colonize wounds.

DispersinB™-based antimicrobial compositions of the invention can be used to inhibit the proliferation of biofilm-embedded gram-negative and gram-positive bacteria, which include, but are not limited to: *Escherichia coli, Proteus mirabilis, Klebsiella pneumoniae, Pseudomonas aeruginosa, Klebsiella oxytoca, Providentia stuarii, Serratia marcescens, Enterococcus faecalis*, Vancomycin Resistant Enterococci (VRE), *Peptostreptococcus* spp., *Corynebacterium* spp., *Clostridium* spp., *Bacteroides* spp., *Prevotella* spp., *Streptococcus pyogenes, Streptococcus viridans, Micrococcus* spp., β-hemolytic *streptococcus* (group C), Beta-hemolytic *streptococcus* (group B), *Bacillus* spp., *Porphyromonas* spp., *Aggregatibacter actinomycetemcomitans, Fusobacterium nucleatum, Treponema denticola, Staphylococcus epidermidis, Staphylococcus aureus* and *Staphylococcus saprophyticus*.

Additionally, DispersinB™-based antimicrobial compositions of the invention can also be used to inhibit the proliferation of biofilm-embedded fungi, such as *Candida albicans, Candida parapsilosis*, and *Candida utilis*.

In one aspect, a DispersinB™-based antimicrobial composition can treat various kinds of wounds, including, but not limited to, cutaneous abscesses, surgical wounds, sutured lacerations, contaminated lacerations, blister wounds, soft tissue wounds, partial thickness and full thickness burns, decubitus ulcers, stasis ulcers, leg ulcers, foot ulcers, venous ulcers, diabetic ulcers, ischemic ulcers, and pressure ulcers Another aspect includes methods of using DispersinB™-based antimicrobial compositions in wound care devices including, but not limited to, non-resorbable gauze/sponge dressing, hydrophilic wound dressing, occlusive wound dressing, hydrogel wound and burn dressing, spray-applicator, and also in ointments, lotions, and suture.

Suitable substrates for receiving a topically applied DispersinB™-based antimicrobial composition finish include, without limitation, fibres, fabrics, and alginates. A fabric may be formed from fibres such as synthetic fibres, natural fibres, or a combination thereof. Synthetic fibres include, for example, polyester, acrylic, polyamide, polyolefin, polyaramid, polyurethane, regenerated cellulose (i.e., rayon), and blends thereof. Suitable polymeric materials include but are not limited to silastic or other silicone-based material, polyethylenetecephtalate (PET), Dacron®, knitted Dacron®, velour Dacron®, polyglacin, chromic gut, nylon, silk, bovine arterial graft, polyethylene (PE), polyurethane, polyvinyl chlorides silastic elastomer, silicone rubber, PMMA [poly(methylmethacrylate), latex, polypropylene (PP), polyolefin, cellulose, poly vinyl]alcohol (PVA), poly(hydroxyethyl methacrylate (PHEMA), poly(glycolic acid), poly(acrylonitrate) (PAN), fluoroethylene-cohexa-fluoropropylene (FEP), Teflon® (PTFE), Cobalt-Cromium alloys, copolymers thereof and mixtures thereof.

A method of incorporating a therapeutically active DispersinB™-based composition of the present invention into the polymeric material includes direct compounding of a therapeutically active substance into a plastic resin before casting or the like.

In addition, a DispersinB™-based antimicrobial composition can further comprise binders, wetting agents, odour absorbing agents, levelling agents, adherents, thickeners, and the like. Other additives may also be present on and/or within a fabric of bandage including antistatic agents, optical brightening compounds, opacifiers (such as titanium dioxide), nucleating agents, antioxidants, UV stabilizers, fillers, permanent press finishes, softeners, lubricants, curing accelerators, adhesives, and the like.

In another embodiment, a DispersinB™-based antimicrobial composition can include a detergent. A detergent may be anionic, cationic, or non-ionic. Detergents can include: sodium dodecyl sulfate (SOS) (also known as lauryl sulfate, sodium salt (other salts are also useful including lithium and potassium salts); sodium cocomonoglyceride sulfonate; sodium lauryl sarcosinate; sodium cholate; sodium deoxycholate; octylglucoside; dodecyldimethylamine oxide; 3-[(3-cholamidopropyl)dimethylammonio]-1-propanesulfonate (CHAPS); dodecyltriethylammonium bromide (DTAB); cetyltrimethylammonium bromide (CTAB); polyoxyethylene-p-isooctylphenyl ether (e.g., Triton® X-20, Triton® X-100, Triton® X-114); alkyl sulfate; alkyl sulfonate; quaternary amines; octyldecyldimethylammonium chloride; dioctyldimethylammonium chloride; didecyldimethylammonium chloride; cetylpyridinium chloride; benzalkonium chloride; benzyldodecyldimethylammoniumn bromide; thonzonium bromide; cholic acid; chenodeoxycholic acid; glycodeoxychlic acid sodium salt; cremophor EL; N-Nonanoyl-N-methylglucamine; saponin; surfactin; protamine, and colistin.

Therapeutic Use for Treating Oral Infections

In an embodiment, a DispersinB™-based antimicrobial composition can treat an oral infection. Oral infections include microorganisms in the subgingival and supragingival plaque. Subgingival plaque comprises microorganisms can cause periodontal disease. Periodontal disease includes gingivitis, periodontitis, acute necrotizing ulcerative gingivitis (ANUG), and localized juvenile periodontitis (LJP). Symptoms of periodontal disease include inflammation of the gingiva, deepening periodontal pockets, and alveolar bone loss.

*A. actinomycetemcomitans* is the principal etiologic agent of LIP and is considered a putative etiologic agent for generalized periodontitis, also referred to as adult periodontitis. *Prevotella intermedia* is considered the chief etiologic agent for ANUG and is also considered a putative etiologic agent of adult periodontitis. *Porphyromonas gingivalis* is considered the main etiologic agent of chronic and severe adult periodontitis, but other microorganisms are thought to contribute to adult periodontitis as well. Other etiologic agents of periodontal diseases include *Fusobacterium nucleatum, Treponema denticola, Eikenella corrodens, P. nigrescens, Campylobacter rectus, Prevotella nigrescens,* and *Bacteroides forsythus.*

In an embodiment, a DispersinB™-based composition can be used to treat oral infections. Preferably, an oral infection would include dental plaque that causes periodontal disease. In another embodiment, an oral infection includes *Streptococcus mutans,* the etiologic agent of caries.

In an embodiment, a method includes administering a composition comprising (a) DispersinB™, an active fragment or variant thereof that disperses a biofilm; and (b) an antimicrobial agent. The antimicrobial agent can be an amount to kill or inhibit microorganisms that cause periodontal disease. In another embodiment, the antimicrobial agent can be an amount to kill or inhibit *S. mutans.*

A structural matrix established during biofilm formation can make colonizing cells able to withstand normal treatment doses of an antimicrobial. In a biofilm, a glycocalyx matrix serves as a barrier that protects and isolates microorganisms from antimicrobials and host defenses (e.g., antibodies, macrophages, etc.) (Costerton et al., 1981, *Ann. Rev. Microbiol.* 35:299-324). In one study, biofilm-associated bacteria were able to survive a concentration of antibiotic 20 times the concentration effective to eliminate the same species of bacteria grown in planktonic culture (Nickel et al., 1985, *Antimicrob. Agents Chemother.* 27:619-624). Higher doses of antimicrobials necessary to eliminate biofilm growth may not be well tolerated in a mammal, particularly a human. A DispersinB™-based composition can overcome this structural protection of biofilm-embedded microorganisms. DispersinB™ can break up a biofilm matrix, whereby the antimicrobial then has access to the microorganisms.

Gel Formulations

In another embodiment, the present invention provides antibiofilm enzyme-based wound gel compositions comprising DispersinB™, or an active fragment or variants thereof, and an antimicrobial agent, can inhibit biofilm formation as well as biofilm growth. In particular, a composition can include (a) DispersinB™, an active fragment or a variant thereof, and (b) triclosan or a broad-spectrum antimicrobial. Such compositions are effective in inhibiting growth and proliferation of biofilm-embedded microorganisms, including both bacterial and fungal species. A composition can further comprise a viscosity improving agent.

Accordingly, an embodiment of the present invention provides wound gel compositions for: (a) DispersinB™ antimicrobial wound gel with a viscosity improving agent (gelling agent); and (b) Triclosan-DispersinB™ antimicrobial wound gel with a viscosity improving agent. In both the wound gels DispersinB™ or an active fragment or variants thereof could be used.

Also, other antimicrobials including, but not limited to, triclosan, antibiotics (such as rifampicin, cefamandole nafate and ciprofloxacin) nitrofurazone, bismuth-thiols [such as bismuth ethanedithiol (BisEDT)], chitosan, epigallocatechin gallate (EGCG), sodium usnate, antineoplastic agents (such as 5-fluorouracil), detergents (such as SDS, benzalkonium chloride), chlorhexidine, chelating agents (such as EDTA), silver compounds, bacteriophage, antimicrobial enzymes (such as glucose oxidase and lactoperoxidase), sugar alcohols (such as xylitol), maleimides [such as N,N-(1,2 phenylene) dimaleimide (oPDM) and N-(1-pyrenyl) maleimide (PyrM)], cadexomer iodine, methylene blue, gentian violet, medium chain dextrans (such as honey), and mixtures thereof can be used in combination with DispersinB™.

According to another embodiment, a Triclosan-DispersinB™ wound gel comprises about 1% triclosan. In a further embodiment, a DispersinB™ wound gel and a Triclosan-DispersinB™ wound gel can optionally further comprises a gelling agent and/or a viscosity improving agent.

Triclosan-DispersinB™ wound gel can be prepared in polyethylene glycol (PEG)/ethanol. PEG of molecular weights ranging between 200 and 511000 can be used in the gel formulation. According to another embodiment, a Triclosan-DispersinB™ wound gel is prepared in 10% polyethylene glycol (PEG) 400 plus 10% ethanol.

According to another embodiment, a viscosity increasing agent is an alginate based material. There are a number of suitable viscosity increasing agents available and, as previously indicated, preferred embodiments of the present invention will rely on gelling agents. A number or gelling agents are available including various gums and polysaccharides, alginates, and both synthetic and natural polymeric compounds. Such gelling agents are well known in the art, in particular in the food and medical arenas and will not be discussed in any specific detail herein apart from some representative examples given later herein. Some useful prior art referencing the use of gelling agents in medical type applications include U.S. Pat. Nos. 4,948,575, 5,674,524, 5,197,954, 5,735,812, 5,238,685, 5,470,576, 5,738,860 5,336,501, 5,482,932. Reference is made to these documents as a background to various viscosity increasing agents, which may find with the present invention.

A DispersinB™ based antimicrobial wound gel can be used to inhibit the proliferation of biofilm-embedded gram-negative and gram-positive bacteria, which include, but are limited to: *Escherichia coli, Proteus mirabilis, Klebsiella pneumoniae, Pseudomonas aeruginosa, Klebsiella oxytoca, Providentia sturtii, Serratia marcescens, Enterobacter cloacae, Enterococcus faecalis*, Vancomycin Resistant Enterococci (VRE), *Peptostreptococcus* spp., *Corynebacterium* spp., *Clostridium* spp., *Bacteriodes* spp., *Prevotella* spp., *Streptococcus pyogenes, Streptococcus viridans, Micrococcus* spp., Beta-hemolytic *streptococcus* (groupC), Beta-hemolytic *streptococcus* (groupB), *Bacillus* spp., *Porphyromonas* spp., *Staphylococcus epidermidis, S. aureus. S. agalactiae* and S. saprophyticus.

Additionally, a DispersinB™ based antimicrobial composition can also be used to inhibit the proliferation of biofilm-embedded fungi, such as *Candida albicans, Candida parapsilosis*, and *Candida utilis*.

Use of Gel Formulations

DispersinB™ based antibiofilm gel formulations can be administered to subjects to inhibit biofilms. Such biofilms can include bacteria, fungi, or a mixture of bacteria and fungi. Biofilms can be associated with wounds. Administration of a DispersinB™ based antibiofilm wound gel can also be achieved wherein a wound dressing or device comprises said DispersinB™ based antibiofilm gel formulations.

A DispersinB™ based antibiofilm gel formulation that is administered to treat a biofilm can also include an antimicrobial, such as triclosan. As further described in the examples, a triclosan-DispersinB™ antibiofilm formulation significantly, if not totally, ablates biofilm growth and/or survival.

In one aspect, a DispersinB™ based antibiofilm wound gel can be used for treating a wounds that includes but is not limited to, a cutaneous abscess, surgical wound, sutured laceration, contaminated laceration, blister wound, soft tissue wound, partial thickness burn, full thickness burn, decubitus ulcer, stasis ulcer, foot ulcer, venous ulcer, diabetic ulcer, ischemic ulcer, pressure ulcer, or combinations thereof.

A wound gel is preferably applied following wound debridement. Although biofilm bacteria cannot be completely eradicated from a wound area by debridement, decreasing biofilm mass and providing increased exposure of the debrided tissue and remaining biofilm bacteria to a wound gel increases wound healing. The slough that fills a chronic wound, previously thought to be comprised of dead cells, cellular debris, bacteria, and tissue fluid, has recently been demonstrated to be comprised primarily of a mixed-species bacterial biofilm. It is therefore of benefit to debride the slough from the wound as completely as possible. Debridement can be performed by surgical, mechanical, autolytic, enzymatic, or a combination of means known to those of skill in the art of wound care.

A wound gel could be applied on chronic wounds along with systemic administration of antibiotics. At present antibiotics are not effective against some chronic wounds as biofilm embedded cells are more resistant to antibiotics. Application of a wound gel with antibiofilm activity will disrupt biofilm embedded cells and systemically administered antibiotics will kill dispersed cells. Therefore, a wound gel of present invention will improve the activity of antibiotics.

A DispersinB™ wound gel could be used sequentially along with antimicrobial agents, which are not compatible with enzymes such as detergents. A DispersinB™ wound gel can be applied on wounds first to disperse biofilm embedded cells and then antimicrobial agents.

A wound gel of the present invention utilizes alginate salts to form a product of the desired viscosity (e.g. gel, putty or pliable sheet, etc.). Alginates appear to be especially suitable for use with a wound gel since physical properties of a gel product appear to be relatively easily controlled. Introduction of polyvalent cations helps to form a gel product of desired consistency. Any moulding, extruding, or forming processes should also be performed at this time so that a final product could be formed into desired configuration. Machining (e.g. slicing) into a final form, such as sheets cut from a block, can also be incorporated into any manufacturing process.

Alginates can also have other potentially realisable advantages by introducing cations or cations that are already a part of the selected alginate. For instance, calcium containing alginates may be selected where there is bleeding, as calcium can promote blood clotting. Another example of advantageous cation exchange by an alginate includes alginate fibre dressings that are high in mannuronic acid, wherein the fibre dressings can readily exchange calcium ions for sodium ions. This increases fluid uptake by the dressing, which consequently forms a soft gel that can be easily flushed away with saline. Fibre dressings high in guluronic acid form stronger gels that keep their shape, making removal in one piece possible.

Alginates can exhibit gelling and cross linking properties promoted by the presence of polyvalent cations. These often, tend to form tougher and less soluble alginate materials and thus may find use in a number of products for altering physical characteristics. Such a modification can be used for a sheet-like embodiment, particularly as a way of increasing the strength or solubility properties of a resulting sheet.

Polyvalent cations may be introduced in a number of ways, including introduction of a soluble solution of polyvalent cations during the blending procedure. Preferably, this should be after gelling of a blend has been initiated to avoid thickening reactions, which interfere with the dispersion and hydrating of all of the sodium (or other) alginate being blended with DispersinB™ and triclosan. However, adding polyvalent cations at different points can theoretically substantially alter the characteristics of the resulting product and thus a number of options open to the user to allow thorn to tailor the physical characteristics of products according to the intended end use and user requirements. It is anticipated that soluble calcium salts, such as calcium chloride, may be introduced at relatively low concentrations to promote the various gelling and cross reactions.

Sheets from wound gels can be formed by placing wound gel in between sheets of a non-wettable material and rolling it to uniform thickness. As a variation, a gauze fabric or other suitable material may be placed on top of a lower non-wettable sheet prior to pouring a wound gel. The rolling procedure is completed with a sheet-like gel bonded to gauze. Various materials could be used to apply DispersinB™ based wound gel including, without limitations, fibres, and fabrics. A fabric may be formed from fibres such as synthetic fibres, natural fibres, or combinations thereof. Synthetic fibres include, for example, polyester, acrylic, polyamide, polyolefin, polyaramid, polyurethane, regenerated cellulose (i.e. rayon), and blends thereof. Suitable polymeric materials include but are not limited to silastic or other silicone-based material, polyethylenetecephtalate (PET), Dacron®, knitted Dacron®, velour Dacron®, polyglacin, chromic gut, nylon, silk, bovine arterial graft, polyethylene (PE), polyurethane, polyvinyl chlorides silastic elastomer, silicone rubber, PMMA[poly(methylmethacrylate), latex, polypropylene (PP), polyolefin, cellulose, poly vinyl]alcohol (PVA), poly (hydroxymethyl)methacrylate (PHEMA), Poly(glycolic acid), poly (acrylonitrate) (PAN), fluoroethylene-cohexafluoropropylene (FEP), Teflon® (PTFE), Cobalt-Cromium alloys, copolymers thereof and mixtures thereof.

Other potentially useful gelling agents include hydrocolloids and hydrogels. These components tend to absorb moisture to form a moist healing environment and tend to absorb less fluid than the alginates. Consequently it is envisaged that they would not be used for embodiments for heavily exuding wounds in which alginates would tend to offer better performance. However, it is envisaged that combinations of various viscosity increasing agents may be used in particular embodiments, particularly each imparts a slightly difference property which helps fulfil a particular specification required by the user. For instance the hydrocolloids or hydrogels may be incorporated into gelling blends to vary properties such as the amount of fluid absorbed from a wound, etc.

In addition, DispersinB™ based wound gels can further comprise binders, wetting agents, odour absorbing agents, levelling agents, adherents, thickeners, coupling agents, pH adjusters, and the like.

A formulation of the present invention may be used for human wound therapy or for veterinary use. A formulation may be applied topically to one or more wounds of, for example, a dog, cat, or other mammal. A formulation may be applied to a bite wound to protect a human from developing an ulcerated wound as the result of infection (often with biofilm fragments from the mouth of the animal).

Compositions of the invention can also include quorum sensing inhibitors (QSIs). Quorum sensing is a means of communication between bacteria, most notably in a biofilm. Quorom sensing is mediated by N-acyl-homoserine lactones (AHLs) in gram-negative bacteria and mostly through small peptides in gram positive bacteria (March & Bentley, *Curr. Opin. Biotechnol.* 15: 495-502 (2004)). Quorom sensing inhibitors can inhibit AHL expression, dissemination, and signal reception. For instance, the *Bacillus* enzyme AiiA hydrolyzes AHLs (Dong et al., *Proc. Natl. Acad. Sci. USA* 97: 3526-3531 (2000)). Other QSIs can include AHL analogs that compete and/or interfere with AHL binding to a receptor (e.g., LuxR). These antagonist AHLs can include AHLs with a longer acyl side chains (e.g., extended with at least one methylene), AHLs with decreased acyl side chain rotation (e.g., introduction of an unsaturated bond close to the amide linkage), or a substitution to the phenyl ring (e.g., parabromo). Other QSIs include furanone compounds (Wu et al., *J. Antimicrob. Chemother.* 53; 1054-1061 (2004)) such as (5Z)-4-bromo-5-(bromomethylene)-3-butyl-2(5H)-furanone (Jones et al., *J. Infect. Dis.* 191: 1881-1888 (2005)), 4-nitropyridine-N-oxide, garlic extract, p-benzoquinone, 2,4,5-tribromo-imidazole, 3-amino-benzen-sulfonamide, and 3-nitro-benzen-sulfonamide (Rasmussen et al., J. Bacteriol. 187: 1799-1814 (2005)).

Compositions of the invention can also include RNAIII inhibitory peptide (RIP) (U.S. Pat. No. 6,291,431). RIP is a heptapeptide (YSPWTNF-NH$_2$; SEQ TD NO: 5) that inhibits *S. aureus* and *S. epidermidis* adhesion to surfaces (e.g., epithelial cells, polymers). Compositions can also include bacterial transcription inhibitors which are known to be active against biofilms (Guillot et al., 2007, *Antimicrob. Agents Chemother.* 51:3117-3121).

Methods to modulate biofilm detachment can include DispersinB™ and other molecules mentioned above. DispersinB™ can be administered to a biofilm concurrently or prior to administering QSIs and/or an antimicrobial. Further, a combination of DispersinB™ and QSIs can be administered concurrently or prior to administering an antimicrobial.

Therapeutic Delivery of Bacteriophages

"Bacteriophage" or "phage" are viruses that infect bacteria. Many phage have the ability to lyse bacteria, usually occurring after viral assembly is completely so fully assembled virus can exit the host cell.

Phage display is a system in which a protein and small peptides are displayed on the surface of a phage as a fusion with one of the coal proteins of the virus. Phage display is a powerful tool that allows the discovery and characterization of proteins that interact with a desired target. Phage display peptide libraries are produced with billions of unique displayed proteins (see, e.g., U.S. Pat. No. 5,702,892). Phage display libraries are well known and extensively used to investigate ligand-receptor binding.

Due to accessibility to solvents, displayed proteins and peptides frequently adopt their native conformation, and behave essentially as it is not attached to the surface of a phage. Therefore, most proteins and peptides attached to phage surfaces are biologically active, and can be used directly without time consuming purification and refolding steps that is otherwise needed for proteins expressed using bacterial and eukaryotic expression systems.

Using phages as antimicrobial agents for infection control has been demonstrated in animal models for *Escherichia coli* (Merrill et al., *Proc. Natl. Acad. Sci. USA* (1996) 93: 3188-3192; Smith & Huggins, *J. Gen. Microbiol.* (1982) 128: 307-

318; Smith & Huggins, *J. Gen. Microbiol.* (1983) 129: 2659-2675; Smith et al., *J. Gen. Microbiol.* (1987) 133: 1111-1126; Smith et al., *J. Gen. Microbiol.* (1987) 133: 1127-1135)); *Pseudomonas aeruginosa* (Soothill, *J. Med. Microbiol.* (1992) 37: 258-261; Soothill, *Burns* (1994) 20: 209-211); *Salmonella enterica* serovar *typhimurium* (Berchieri et al., *Res. Microbiol.* (1991) 142: 541-549); *Staphylococcus aureus* (Matsuzaki et al., *J. Infect. Dis.* (2003) 187: 613-624); and *Vibrio vulnificus* (Cerveny et al., *Infect. Immun.* (2002) 70: 6251-6262). Using bacteriophage to treat biofilm-associated infection, however, is problematic because a biofilm acts as a diffusion barrier to the phage (Doolittle et al., *Can. J. Microbiol.* (1995) 41: 12-18; Doolittle et al, *Ind. J. Microbiol.* (1996) 16: 331-341).

Routes of administration of phage therapy include but are not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Excipients which can be used as a vehicle for the delivery of phage are well known. For example, free phage could be in lyophilized form and be dissolved just prior to administration by IV injection. Dosage of administration is contemplated to be about $10^6$ pfu/kg/day, about $10^7$ pfu/kg/day, about $10^8$ pfu/kg/day, about $10^9$ pfu/kg/day, about $10^{10}$ pfu/kg/day, about $10^{11}$ pfu/kg/day, about $10^{12}$ pfu/kg/day, or about $10^{13}$ pfu/kg/day. Phage can be administered until successful elimination of pathogenic bacteria is achieved.

With respect to aerosol administration, antimicrobial phage can be incorporated into an aerosol formulation specifically designed for administration to the lungs by inhalation. Many such aerosols are well known, and the present invention is not limited to any particular formulation. An example of such an aerosol is the Proventil™ inhaler manufactured by Schering-Plough, the propellant of which contains trichloromonofluoromethane, dichlorodifluoromethane, and oleic acid. Concentrations of propellant ingredients and emulsifiers are adjusted if necessary based on the phage being used in the treatment. The number of phage to be administered per aerosol treatment can be about $10^6$ pfu, about $10^7$ pfu, about $10^8$ pfu, about $10^9$ pfu, about $10^{10}$ pfu, about $10^{11}$ pfu, about $10^{12}$ pfu, or about $10^{13}$ pfu.

Treatment of Devices

In a further embodiment, a composition(s) of the present invention can be used to inhibit the growth and proliferation of biofilm embedded microorganisms on devices, and in particular, medical devices. The compositions of the present invention can be used in the preparation of medical devices for implantation in a mammal. A medical device to be implanted can be coated, incorporated or treated with a composition(s) of the present invention. A composition(s) of the present invention can also be used to prevent infections caused by an implanted medical device, including but not limited to urinary tract infections and vascular infections.

In one embodiment, a composition comprises DispersinB™ or an active fragment thereof in combination with triclosan. An amount of DispersinB™ included in a composition is preferably between about 0.1 and 500 µg/ml and more preferably about 40 µg/ml. The higher end of this range can be used to prepare a concentrated product which may be diluted prior to use. The amount of triclosan included in a composition is preferably between about 0.1 and 100 mg/ml and more preferably about 10 mg/ml. The higher end of this range can be used to prepare a concentrated product which may be diluted prior to use.

In another embodiment of the present invention, the composition comprises effective amounts of DispersinB™ and rifampicin. In yet another embodiment of the present invention, the composition comprises effective amounts of DispersinB™ and cefamandole nafate. In yet another embodiment of the present invention, the composition comprises effective amounts of DispersinB™ and nitrofurazone.

Higher concentrations of a compound can be used for certain applications depending on targeted bacteria and a device to be treated. Suitable working concentrations can easily be determined using known methods.

In an embodiment of the present invention, wound dressings including but not limited to sponges or gauzes can be impregnated with the isolated DispersinB™ protein or active fragment or variant thereof to prevent or inhibit bacterial or fungal attachment and reduce the risk of wound infections, Similarly, catheter shields as well as other materials used to cover a catheter insertion sites can be coated or impregnated with a DispersinB™ protein or active fragment or variant thereof to inhibit bacterial or fungal biofilm attachment thereto. Adhesive drapes used to prevent wound infection during high risk surgeries can be impregnated with the isolated protein or active fragment or variant thereof as well. Additional medical devices which can be coated with a DispersinB™ protein or active fragment or variant thereof include, but are not limited to, central venous catheters, intravascular catheters, urinary catheters, Hickman catheters, peritoneal dialysis catheters, endotracheal catheters, mechanical heart valves, cardiac pacemakers, arteriovenous shunts, schleral buckles, prosthetic joints, tympanostomy tubes, tracheostomy tubes, voice prosthetics penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buttered saline (pH approximately 7.5) and bicarbonate butter (pH approximately 9.0). In yet another embodiment, an isolated DispersinB™ protein or active fragment or variant thereof can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok® connectors, needleless connectors and hubs as well as other implantable devices. These solutions can also be used to coal or disinfect surgical instruments including, but not limited to, clamps, forceps, scissors, skin hooks, tubing, needles, retractors, scalers, drills, chisels, rasps and saws. In a preferably embodiment, the composition comprising DispersinB™, an active fragment, or a variant thereof, and triclosan, is used to coat a medical device, such as a catheter. Alternatively, the composition comprising DispersinB™, an active fragment or a variant thereof, and triclosan, can be incorporated into the medical device as it is being made, for example, through an extrusion process. Compositions of the invention can be prepared using known methods. Generally, components are dissolved in a suitable solvent, such as water, glycerol, organic acids, and other suitable solvents Compositions of the invention useful for the treatment of devices may include any number of well known active components and base materials. Such compositions may further comprise ingredients such as, but not limited to: suitable solvents such as water; antibiotics such antibacterials and antifungals; binding, bonding, or coupling agent, cross-linking agent; or a pH adjuster.

Compositions of the invention useful for the treatment of devices may further comprise additional antimicrobial ingredients such as bis-phenols, biguanides, anilides, diamidines, halogen-releasing agents, metallic ions, chelating agents, cationic peptides/polypeptides, N-substituted maleimides, and quaternary ammonium compounds. Examples of bis-phenols useful for preparing compositions of the present invention include, but are not limited to, triclosan and hexachlorophene. Examples of biguanides useful for preparing compositions of the present invention include, but are not limited to, chlorhexidine, chlorhexidine salts, alexidine and polymeric biguanides. Examples of anilides useful for preparing compositions of the present invention include, but are not limited to, triclocarban. Examples of diamidines useful for preparing compositions of the present invention include, but are not limited to, propamidine and dibromopropamidine. Examples of halogen-releasing agents useful for preparing compositions of the present invention include, but are not limited to, iodine compounds, silver compounds, silver nanoparticles and halophenols. Examples of metallic ions useful for preparing compositions of the present invention include, but are not limited to, gallium and other related metal derivatives. Examples of chelating agents useful for preparing compositions of the present invention include, but are not limited to, lactoferrin, ovotransferrin, serotransferrin, EDTA and EGTA. Examples of cationic peptides/polypeptides useful for preparing compositions of the present invention include, but are not limited to, protamine sulfate, lyzozyme and polylysine. Examples of N-maleimides useful for preparing compositions of the present invention include, but are not limited: to N-ethylmaleimide (NEM), 5,5-dithiobis-(2-nitrobenzoic acid) (DTNB), N-phenylmaleimide (PheM), N-(1-pyrenyl) maleimide (PyrM), naphthalene-1,5-dimaleimide (NDM), N,N'-(1,2-phenylene)dimaleimide (oPDM), N,N'-1,4-phenylene dimaleimide (pPDM), N,N'-1,3-phenylene dimaleimide (mPDM), and 1,1-(methylenedi-4,1-phenylene)bismaleimide (BM). Examples of quaternary ammonium compounds useful for preparing compositions of the present invention include, but are not limited to benzalkonium chloride, tridodecyl methyl ammonium chloride, cetrimide and didecyl dimethyl ammonium chloride.

Other possible components of the composition include, but are not limited to, buffer solutions, phosphate buffered saline, saline, polyvinyl, polyethylene, polyurethane, polypropylene, silicone (e.g., silicone lassoers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylamineoethyl methacrylate), poly-(dialkylaminomethyl styrene) or poly-(vinylpyridine), polyammonium ions (e.g., poly-(2-methacryloxyethyl trialkyl ammonium ion), poly-(vinylbenzyl trialkyl ammonium ions), poly-(N,N-alkylypyridinium ion) or poly-(dialkyloctamethylene ammonium ion) and polysulfonates (e.g. poly-(vinyl sulfonate) or poly-(styrene sulfonate), collodion, nylon, rubber, plastic, polyesters, Dacron™ (polyethylene tetraphthalate), Teflon™ (polytetrafluoroethylene), latex, and derivatives thereof; elastomers and Dacron (sealed with gelatin, collagen or albumin, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above-exemplified polymers may also be used.

Examples of biofilm embedded bacteria that may be inhibited using compositions according to the invention include gram-negative bacteria such as, but not limited to: *Escherichia coli, Proteus mirabilis, Klebsiella pneumoniae, Pseudomonas aeruginosa, Klebsiella oxytoca, Providentia stuartii*, or *Serratia marcescens* and gram-positive bacteria such as, but not limited to: *Enterococcus faecalis*, Vancomycin Resistant Enterococci (VRE), *Streptococcus viridans, Staphylococcus epidermidis*, and *Staphylococcus aureus* or *Staphylococcus saprophyticus*. These bacteria are commonly found associated with medical devices including catheters.

Compositions according to the invention can also be used to inhibit the growth and proliferation of biofilm embedded fungus such as *Candida albicans, Candida parapsilosis*, and *Candida utilis*. In another aspect, the present invention provides a method of preparing a device comprising treating at least one surface of the device with an effective amount of DispersinB™, an active fragment or variant thereof, and an effective amount of triclosan, according to the invention.

The term "effective" refers to a sufficient amount of active components to substantially prevent growth or proliferation of biofilm embedded microorganisms on at least one surface of a medical device coated with an embodied composition; and as a sufficient amount of the active components to substantially penetrate, or break-up, a biofilm on at least one surface of a medical device, thereby facilitating access of active components, antimicrobial agents, and/or antifungal agents to microorganisms embedded in a biofilm, and thus, removal of substantially all microorganisms from at least one surface of a medical device treated with a solution of an embodied composition. An amount will vary for each active component and upon known factors such as pharmaceutical characteristics; type of medical device; degree of biofilm embedded microorganism contamination; and use and length of use.

Examples of devices that can be treated using the compositions of the invention include medical devices such as tubing and other medical devices, such as catheters, pacemakers, prosthetic heart valves, prosthetic joints, voice prostheses, contact lenses, and intrauterine devices.

Medical devices include disposable or permanent or indwelling catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, endotracheal tubes, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, wound dressings, orthopedic implants, and any other device used in the medical field.

Medical devices also include any device which may be inserted or implanted into a human being or other animal, or placed at the insertion or implantation site such as the skin near the insertion or implantation site, and which include at least one surface which is susceptible to colonization by biofilm embedded microorganisms.

Medical devices for the present invention include surfaces of equipment in operating rooms, emergency rooms, hospital rooms, clinics, and bathrooms.

Implantable medical devices include orthopedic implants, which may be inspected for contamination or infection by biofilm embedded microorganisms using endoscopy. Insertable medical devices include catheters and shunts, which can be inspected without invasive techniques such as endoscopy.

Medical devices may be formed of any suitable metallic materials or non-metallic materials. Examples of metallic materials include, but are not limited to, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex™ (polytetrafluoroethylene), Dacron™ (polyethylene tetraphthalate), Teflon™ (polytetrafluoroethylene), latex, elastomers, and Dacron™ sealed with gelatin, collagen, or albumin, and derivatives or combinations thereof.

In a preferred embodiment, the method of treating at least one surface of a medical device comprises contacting a medical device with a composition according to the invention. As used herein, the term "contacting" includes, but is not limited to: coating, spraying, soaking, rinsing, flushing, submerging, and washing. A medical device is contacted with a composition for a period of time sufficient to remove substantially all biofilm embedded microorganisms from a treated surface of a medical device.

In a more preferred embodiment, a medical device is submerged in a composition for at least 5 minutes. Alternatively, a medical device may be flushed with a composition. In the case of a medical device being tubing, such as dental drain tubing, a composition may be poured into a dental drain tubing and both ends of the tubing clamped such that the composition is retained within the lumen of the tubing. The tubing is then allowed to remain filled with the composition for a period of time sufficient to remove substantially all of the microorganisms from at least one surface of the medical device, generally, for at least about 1 minute to about 48 hours. Alternatively, tubing may be flushed by pouring a composition into the lumen of the tubing for an amount of time sufficient to prevent substantial growth of all biofilm embedded microorganisms. Concentrations of active components in a composition may vary as desired or necessary to decrease the amount of time the composition is in contact with a medical device.

In another embodiment of a method for treating a surface of a device, a composition of the invention may also include an organic solvent, a medical device material penetrating agent, or adding an alkalinizing agent to the composition, to enhance reactivity of a surface of the medical device with the composition. An organic solvent, medical device material penetrating agent, and/or alkalinizing agent are those which preferably facilitate adhesion of a composition to at least one surface of a medical device.

Another aspect provides a method of coating a composition of the invention onto at least one surface of a device. Preferably, the device is a medical device. Broadly, a method for coating a medical device includes the steps of providing a medical device; providing or forming a composition coating; and applying the composition coating to at least one surface of the medical device in an amount sufficient to substantially prevent growth or proliferation of biofilm embedded microorganisms on at least one surface of the medical device. In one specific embodiment, a method for coating a medical device includes the steps of forming a composition of the invention of an effective concentration for activating an active component, thereby substantially preventing growth or proliferation of microorganisms on at least one surface of the medical device, wherein the composition of the invention is formed by combining an active component and a base material. At least one surface of a medical device is then contacted with a composition of the invention under conditions wherein the composition of the invention covers at least one surface of the medical device. The term "contacting" further includes, but is not limited to: impregnating, compounding, mixing, integrating, coating, spraying and dipping.

In another embodiment of a method for coating a medical device, a composition coating is preferably formed by combining an active component and a base material at room temperature and mixing the composition for a time sufficient to evenly disperse active agents in the composition prior to applying the composition to a surface of the device. A medical device may be contacted with a composition for a period of time sufficient for a composition to adhere to at least one surface of the device. After a composition is applied to a surface of a device, it is allowed to dry.

A device is preferably placed in contact with a composition by dipping the medical device in the composition for a period of time ranging from about 30 seconds to about 180 minutes at a temperature ranging from about 25° C. to about 60° C. Preferably, a device is placed in contact with a composition by dipping the medical device in the composition for about 60 minutes at a temperature of about 37° C. A device is removed from a composition and then allowed to dry. A medical device may be placed in an oven or other heated environment for a period of time sufficient for a composition to dry.

Although one layer, or coating, of a composition is believed to provide a desired composition coating, multiple layers are preferred. Multiple layers of a composition are preferably applied to at least one surface of a medical device by repeating steps discussed above. Preferably, a medical device is contacted with a composition three times, allowing the composition to dry on at least one surface of the medical device prior to contacting the medical device with the composition for each subsequent layer. Thus, a medical device preferably includes three coats, or layers, of a composition on at least one surface of the medical device.

In another embodiment, a method for coating medical devices with a composition coating includes the steps of forming a composition coating of an effective concentration to substantially prevent the growth or proliferation of biofilm embedded microorganisms on at least one surface of a medical device by dissolving an active component in an organic solvent, combining a medical device material penetrating agent to the active component(s) and organic solvent, and combining an alkalinizing agent to improve reactivity of the material of the medical device. A composition is then heated to a temperature ranging from about 30° C. to about 60° C. to enhance adherence of a composition coating to at least one surface of the device. A composition coating is applied to at least one surface of a medical device, preferably by contacting the composition coating to the at least one surface of the medical device for a sufficient period of time for the composition coating to adhere to at least one surface of the medical device. A medical device is removed from a composition coating and allowed to dry, preferably, for at least 18 hours at room temperature. A medical device may then be rinsed with a liquid, such as water and allowed to dry for at least 2 hours, and preferably 4 hours, before being sterilized. To facilitate drying of a composition of the invention onto a surface of a medical device, a medical device may be placed into a heated environment such as an oven.

In another aspect, the invention provides a method of incorporating a composition according to the invention into a device. Preferably, a device is a medical device and a composition is incorporated into a material forming the medical device during formation of the medical device. For example, a composition may be combined with a material forming the medical device, e.g., silicone, polyurethane, polyethylene, Gortex™ (polytetrafluoroethylene), Dacron™ (polyethylene tetraphthalate), and Teflon™ (polytetrafluoroethylene), and/or polypropylene, and extruded with the material forming the medical device, thereby incorporating the composition into material forming the medical device. In this embodiment, the composition may be incorporated in a septum or adhesive, which is placed at the medical device insertion or implantation site. One example of a medical device having a composition incorporated into the material forming the medical device in accordance with this embodiment is a catheter insertion seal having an adhesive layer described below in greater detail. Another example of a medical device having a composition incorporated into the material is an adhesive. A composition of the invention can be integrated into an adhesive, such as tape, thereby providing an adhesive, which may prevent growth or proliferation of biofilm embedded microorganisms on at least one surface of the adhesive.

EXAMPLES

Example 1

Effect of DispersinB™ on Biofilm Formation

An in vitro microplate assay was performed to determine the effect of DispersinB™ on the growth and biofilm formation of *E. coli*, *S. epidermidis*, and *S. aureus*. *E. coli* biofilm was grown in colony forming antigen (CFA) medium. Purified DispersinB™ was obtained from Jeffrey Kaplan (University of Medicine and Dentistry of New Jersey) and was produced as described in Kaplan et al., 2003, *J. Bacteriol.* 185: 4693-4698. *S. epidermidis* and *S. aureus* biofilm was grown in tryptic soy broth (TSB). Bacteria were separately grown in 96-well microtiterplate in the absence and presence of DispersinB™ at different concentrations. The *E. coli* plate was incubated at 26° C. for 24 hours. The *S. epidermidis* and *S. aureus* biofilm plates were incubated at 37° C. for 24 hours. Growth of planktonic cells based on the absorbance at 600 nm was determined using Labsystems Multiskan Ascent microplate reader. Biofilm was measured by discarding the medium; rinsing the wells with water (three times), and staining bound cells with crystal violet. The dye was solubilized with 33% acetic acid, and absorbance at 630 nm was determined using a microtiter plate reader. For each experiment, background staining was corrected by subtracting the crystal violet bound to uninoculated control (FIG. 1). The tests showed an appreciable effect by DispersinB™ on biofilm formation among all the cultures tested.

Example 2

Dispersal of *S. epidermidis* Biofilm by DispersinB™

Figure 2:
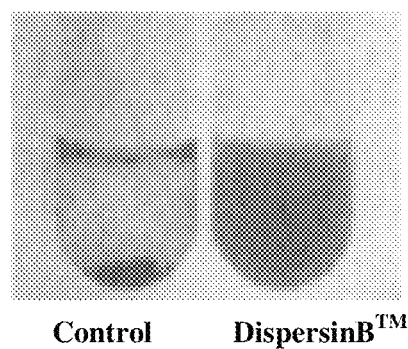
FIG. 2 shows the effect of DispersinB™ in polystyrene tubes on *S. epidermidis* biofilm dispersal.

Dispersal of *S. epidermidis* biofilm by DispersinB™ was demonstrated by growing *S. epidermidis* biofilm in a tube. The biofilm growth from the surface was scraped from the bottom of the tube and transferred to another tube (FIG. 2). Under these condition cells formed a sticky aggregate that rapidly settle to the bottom of the tube. Treatment of the cell aggregates with DispersinB™ resulted in uniformly turbid cell suspensions indicating that the treatment with DispersinB™ detaches the biofilm.

Example 3

Figure 3:
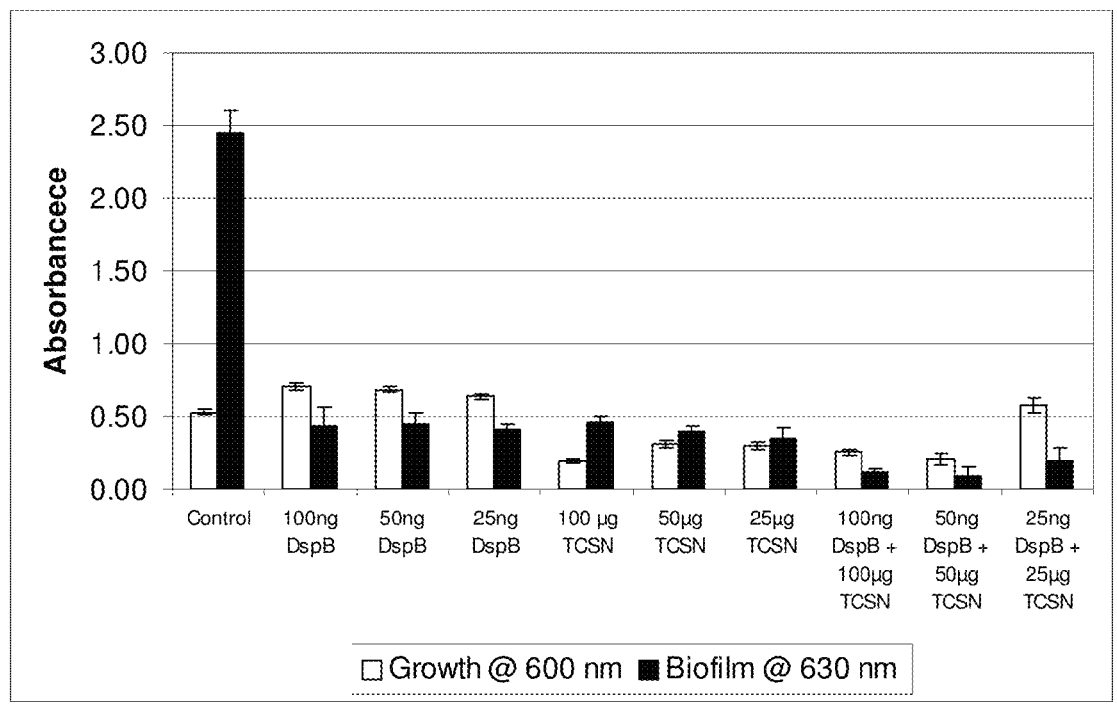
FIG. 3 is bar graph showing an enhanced inhibitory effect of a DispersinB™ and Triclosan (TCSN) combination on *S. epidermidis* biofilm formation. Planktonic (□) and biofilm (■) *S. epidermidis* growth was measured in media with no antimicrobials (control), DispersinB™ (25, 50, and 100 ng/ml), TCSN (25, 50, and 100 µg/ml), and the combination of DispersinB™ (25, 50, or 100 ng/ml) and TCSN (25, 50, and 100 µg/ml).

Enhanced Inhibitory Effect of DispersinB™ and Triclosan (TCSN) Combination on *Staphylococcus epidermidis* Biofilm An in vitro microplate assay was performed to determine the effect of DispersinB™ and triclosan (an antimicrobial agent) on the growth and biofilm formation of *S. epidermidis*. An overnight culture of *S. epidermidis* in Tryptic Soy Broth (TSB) was used as inoculum. Bacteria were grown in TSB on a 96-well microtiterplate in the absence and presence of each compound (DispersinB™ or TCSN) at different concentrations separately and together (DispersinB™+TCSN). Concentrations of DispersinB™ included 25 ng/ml, 50 ng/ml, and 100 ng/ml. Concentrations of TCSN included 25 µg/ml, 50 µg/ml, and 100 µg/ml. The plate was incubated at 37° C. for 24 hours. The growth and biofilm was measured as explained in Example 1. The combination of DispersinB™ and TCSN (50 ng/ml+50 µg/ml, respectively) showed enhanced inhibitory effect on *S. epidermidis* biofilm formation (FIG. 3).

Example 4

Antimicrobial Activity of DispersinB™ and Triclosan (TCSN) Combination Against Wound Infection-Associated Pathogens The combined antimicrobial activity of DispersinB™ and triclosan was studied by determining minimal inhibitory concentrations (MIC) in a 96 well microtiter plate. Briefly, serial two-fold dilutions of triclosan and in presence of DispersinB™ (40 µg/ml) were performed in TSB. A suspension of each microorganism from Table 1 was added to wells at a concentration of 5×10⁵ CFU/mL, and the microtiter plates were incubated at 37° C. The MIC was defined, as the lowest concentration of an antimicrobial required for total inhibition of a test microorganism at 37° C. Triclosan in combination with DispersinB™ was active against all the pathogens tested.

TABLE 1

MIC of triclosan in the presence of DispersinB ™ (40 µg/ml) enzyme against wound infection associated pathogens

| Cultures | MIC (µg/ml) |
| --- | --- |
| S. aureus | <0.097 |
| S. epidermidis | 3.125 |
| E. faecalis | 100 |
| E. faecium Vancomycin resistant | 25 |
| E. faecium | 12.5 |
| E. coli | 6.25 |
| Enterobacter cloacae | 25 |
| P. mirabilis | 12.5 |
| K. pneumoniae | 25 |
| C. albicans | 100 |

Example 5

Figure 4:
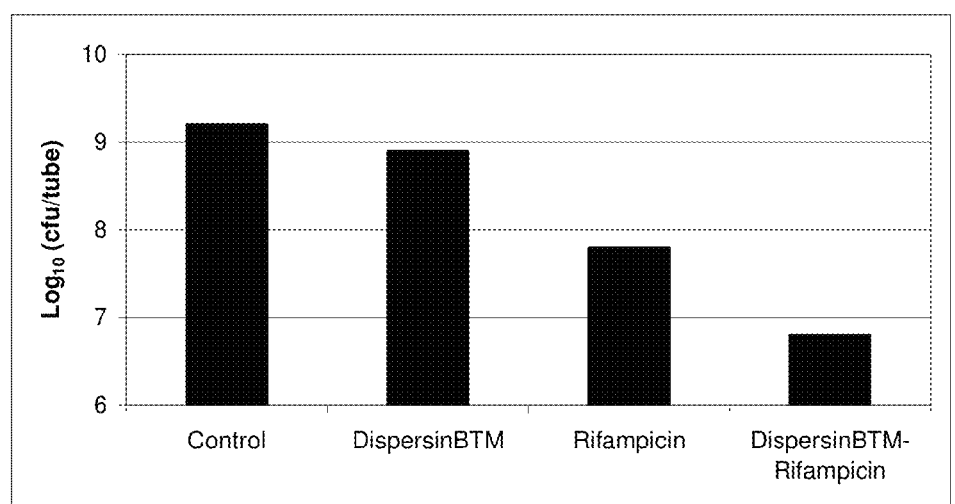
FIG. 4 is bar graph showing an enhanced effect of DispersinB™ on the sensitivity of biofilm-embedded *S. epidermidis* to rifampicin. *S. epidermis* growth was measured in media with no antimicrobials (control), DispersinB™ (20 µg/ml), rifampicin (100 µg/ml), and a combination of DispersinB™ (20 µg/ml) and rifampicin (100 µg/ml).
Figure 5:
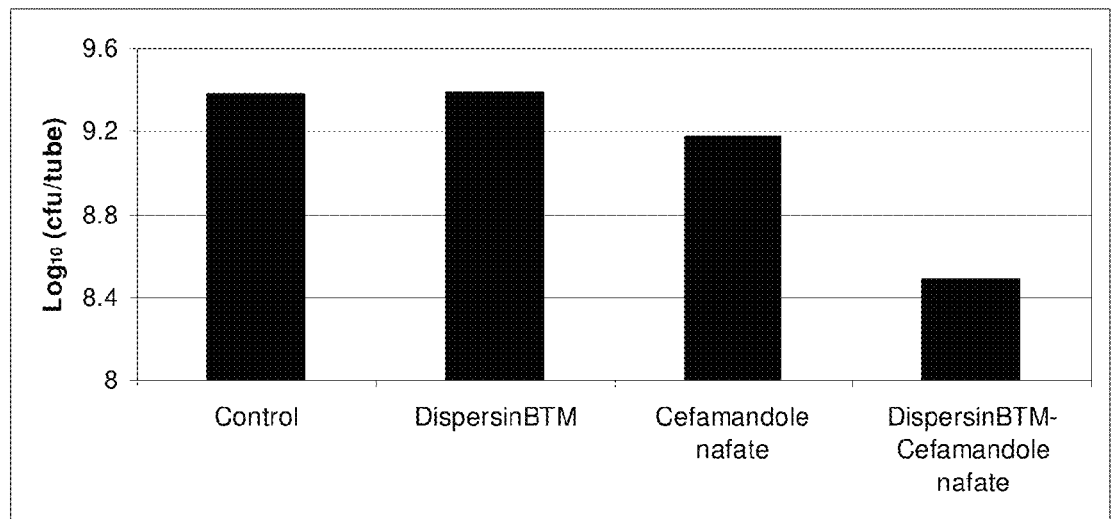
FIG. 5 is bar graph showing an enhanced effect of DispersinB™ on the sensitivity of biofilm-embedded *S. epidermidis* to cefamandole nafate. *S. epidermidis* growth was measured in media with no antimicrobials (control), DispersinB™ (20 µg/ml), cefamandole nafate (0.1 µg/ml), and a combination of DispersinB™ (20 µg/ml) and cefamandole nafate (0.1 µg/ml).

Enhancing Effect of DispersinB™ on the Sensitivity of Biofilm-Embedded *Staphylococcus epidermidis* to Antimicrobials An in vitro biofilm-dispersal assay was performed to determine whether DispersinB™ increased sensitivity of biofilm-embedded *S. epidermidis* to rifampicin and/or cefamandole nafate. *S. epidermidis* biofilm was grown in 1.5 ml polypropylene microcentrifuge tubes (200 µl culture volume), was rinsed with 200 µl of fresh medium and then treated with 200 µl medium containing 100 µg/ml of rifampicin or 0.1 µg/ml cefamandole nafate, each alone or in combination with 20 µg/ml of DispersinB™. After 3 hours at 37° C., 101 of 200 µg/ml DispersinB™ was added to each tube, and tubes were incubated for additional 5 min to detach biofilm. Serial dilutions of cells were plated on TSA. DispersinB™ enhanced the inhibitory effect of rifampicin and cefamandole nafate on biofilm-embedded *S. epidermidis* (FIGS. 4 and 5). DispersinB™ dispersed *S. epidermidis* biofilm and made it susceptible to rifampicin and cefamandole nafate.

Example 6

Figure 6:
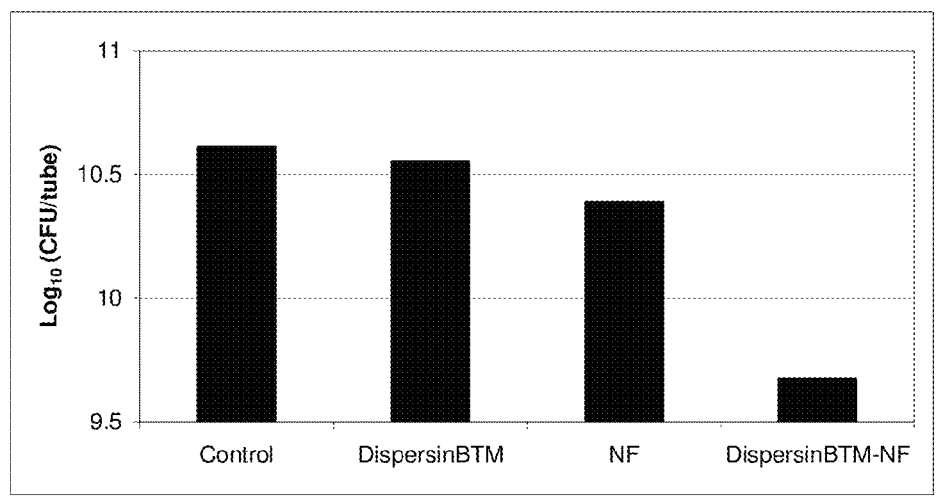
FIG. 6 is bar graph showings an enhanced effect of DispersinB™ on the sensitivity of biofilm-embedded *S. epidermidis* to nitrofurazone. *S. epidermis* growth was measured in media with no antimicrobials (control), DispersinB™ (20 µg/ml), nitrofurazone (25 µg/ml), and a combination of DispersinB™ (20 µg/ml) and nitrofurazone (25 µg/ml).

Enhancing Effect of DispersinB™ on the Sensitivity of *Staphylococcus epidermidis* Biofilm to Nitrofurazone An in vitro biofilm dispersal assay was performed to determine the effect of DispersinB™ on enhancing the sensitivity of *S. epidermidis* biofilm to nitrofurazone (NF). *S. epidermidis* biofilm grown in 1.5 ml polypropylene microcentrifuge tubes was rinsed with 200 µl of fresh medium and then treated with 200 µl medium containing 25 µg/ml of NF and/or 20 µg/ml of DispersinB™. Biofilm detachment and plating biofilm embedded cells were performed as described in Example 5. When DispersinB™ was used in combination with NF, there was increased sensitivity of *S. epidermidis* biofilm to NF (FIG. 6). Thus, the DispersinB™ and NF combination had an enhanced inhibitory effect on biofilm-embedded *S. epidermidis*.

Example 7

Enhancing Effect of DispersinB™ on the Sensitivity of *Staphylococcus epidermidis* Biofilm to Bismuth Ethanedithiol (BisEDT)

Figure 7:
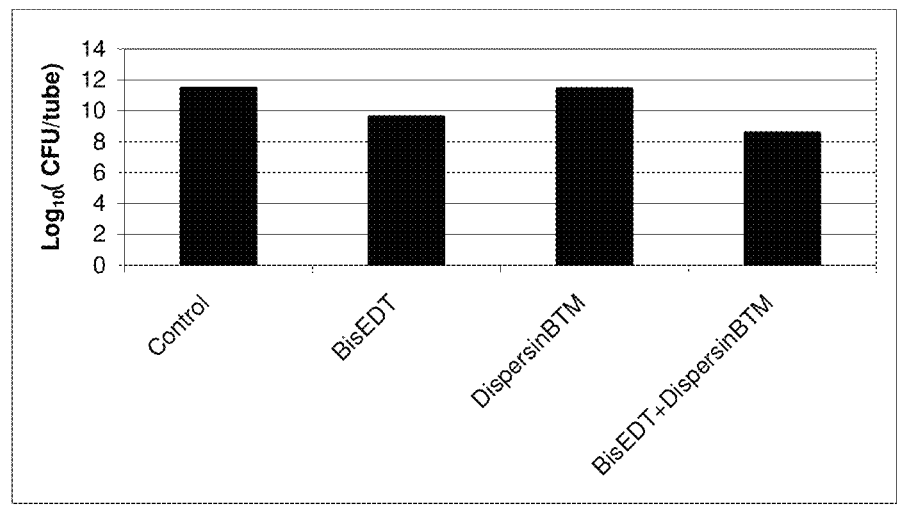
FIG. 7 is bar graph showing an enhanced effect of DispersinB™ on the sensitivity of biofilm-embedded *S. epidermidis* to bismuth ethanedithiol (BisEDT). *S. epidermidis* growth was measured in media with no antimicrobials (control), DispersinB™ (20 µg/ml), BisEDT (0.5 mM), and a combination of DispersinB™ (20 µg/ml) and BisEDT (0.5 mM).

An in vitro biofilm dispersal assay was performed to determine the effect of DispersinB™ on enhancing the sensitivity of *S. epidermidis* biofilm to bismuth ethanedithiol (BisEDT). *S. epidermidis* biofilm grown in 1.5 ml polypropylene microcentrifuge tubes was rinsed with 200 µl of fresh medium and then treated with 200 µl medium containing 0.5 mM of BisEDT and/or 20 µg/ml of DispersinB™. Biofilm detachment and plating biofilm embedded cells were performed as described in Example 5. DispersinB™ in combination with BisEDT increased the sensitivity of *S. epidermidis* biofilm to BisEDT (FIG. 7). Thus, the DispersinB™ and BisEDT combination bad an enhanced inhibitory effect on biofilm-embedded *S. epidermidis*.

Example 8

Enhancing Effect of DispersinB™ on the Sensitivity of *Staphylococcus epidermidis* Biofilm to Ciprofloxacin (CF)

Figure 8:
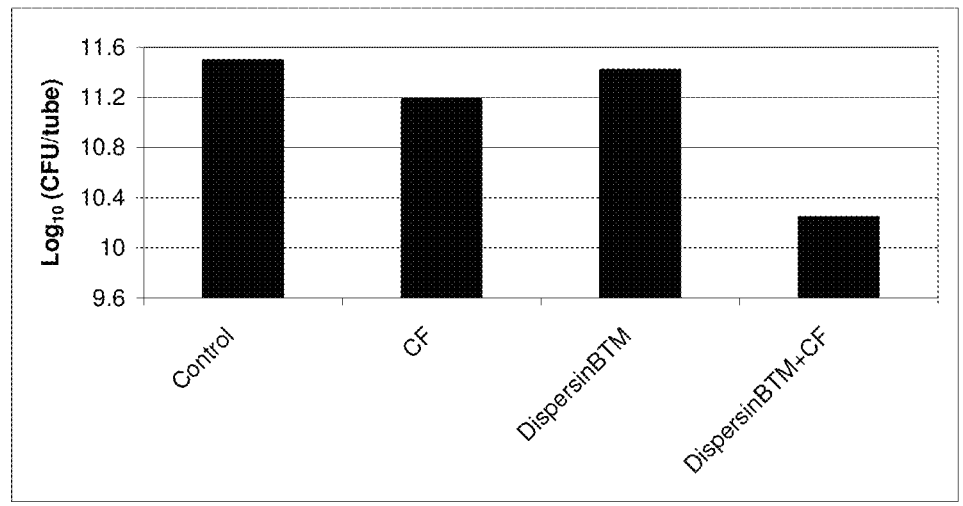
FIG. 8 is bar graph showing an enhanced effect of DispersinB™ on the sensitivity of biofilm-embedded *S. epidermidis* to ciprofloxacin (CF). *S. epidermidis* growth was measured in media with no antimicrobials (control), DispersinB™ (20 µg/ml), CF (200 µg/ml), and a combination of DispersinB™ (20 µg/ml) and CF (200 µg/ml).

An in vitro biofilm dispersal assay was performed to determine the effect of DispersinB™ on enhancing the sensitivity of *S. epidermidis* biofilm to Ciprofloxacin (CF). *S. epidermidis* biofilm grown in 1.5 ml polypropylene microcentrifuge tubes was rinsed with 200 µl of fresh medium and then treated with 200 µl medium containing 200 µg/ml of CF and/or 20 µg/ml of DispersinB™. Biofilm detachment and plating biofilm embedded cells were performed as described in Example 5. DispersinB™ in combination with CF increased the sensitivity of *S. epidermidis* biofilm to CF (FIG. 8). Thus, the DispersinB™ and CF combination had an enhanced inhibitory effect on biofilm-embedded *S. epidermidis*.

Example 9

Effect of DispersinB™ on the Sensitivity of *Staphylococcus epidermidis* Biofilm to Lactoferrin (Lf)

Figure 9:
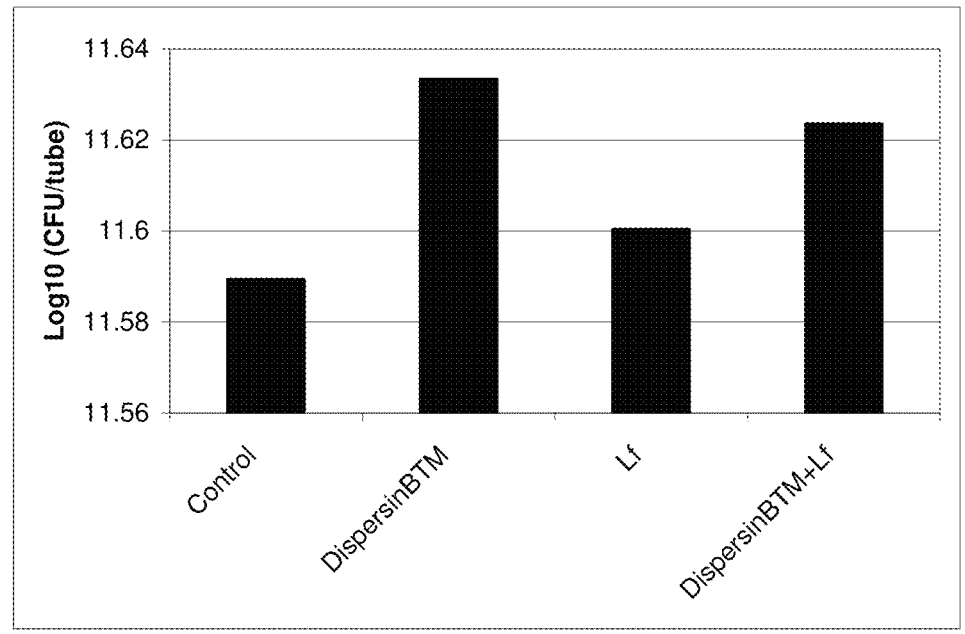
FIG. 9 is a bar graph showing an enhanced effect of DispersinB™ on the sensitivity of biofilm-embedded *S. epidermidis* to lactoferrin (Lf). *S. epidermis* growth was measured in media with no antimicrobials (control), DispersinB™ (20 µg/ml), Lf (5 mg/ml), and a combination of DispersinB™ (20 µg/ml) and Lf (5 mg/ml).

An in vitro biofilm dispersal assay was performed to determine the effect of DispersinB™ on the sensitivity of *S. epidermidis* biofilm to lactoferrin (Lf). *S. epidermidis* biofilm grown in 1.5 ml polypropylene microcentrifuge tubes was rinsed with 200 µl of fresh medium and then treated with 200 µl medium containing 5 mg/ml of Lf and/or 20 µg/ml of DispersinB™. Biofilm detachment and plating biofilm embedded cells were performed as described in Example 5. DispersinB™ in combination with Lf, did not increase the sensitivity of *S. epidermidis* biofilm to Lf (FIG. 9). Thus, the DispersinB™ and Lf combination did not have an enhanced inhibitory effect on biofilm-embedded *S. epidermidis*.

Example 10

Enhancing Effect of DispersinB™ on the Sensitivity of *Staphylococcus epidermidis* Biofilm to Conalbumin/Ovotransferrin (OT)

Figure 10:
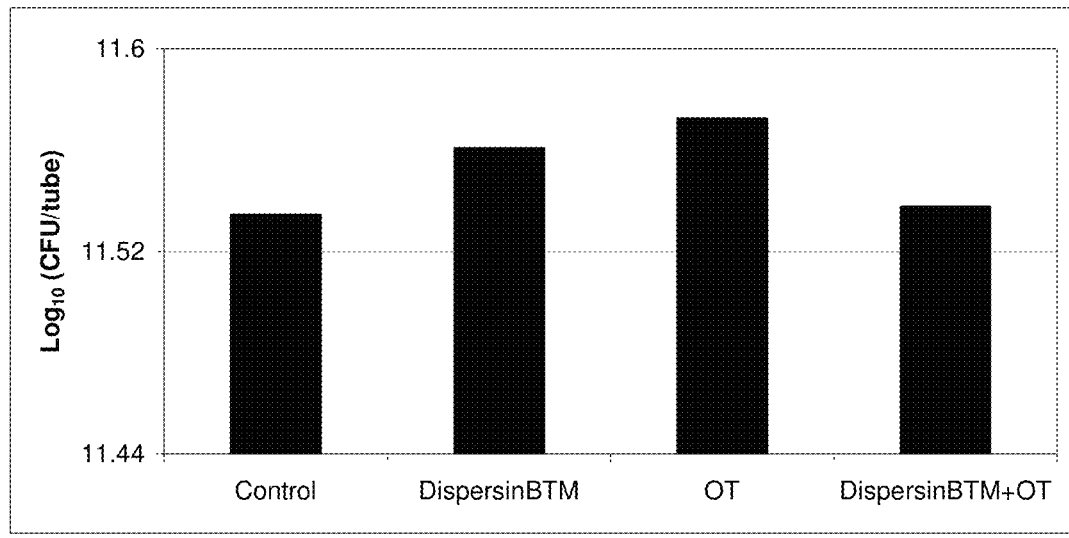
FIG. 10 is bar graph showing an enhanced effect of DispersinB™ on the sensitivity of biofilm-embedded *S. epidermidis* to conalbumin/ovotransferrin (OT). *S. epidermis* growth was measured in media with no antimicrobials (control), DispersinB™ (20 µg/ml), OT (10 mg/ml), and a combination of DispersinB™ (20 µg/ml) and OT (10 mg/ml).

An in vitro biofilm dispersal assay was performed to determine the effect of DispersinB™ on enhancing the sensitivity of *S. epidermidis* biofilm to ovotransferrin (OT). *S. epidermidis* biofilm grown in 1.5 ml polypropylene microcentrifuge tubes was rinsed with 200 µl of fresh medium and then treated with 200 µl medium containing 10 mg/ml of OT and/or 20 µg/ml of DispersinB™ Biofilm detachment and plating biofilm embedded cells were performed as described in Example 5. DispersinB™ in combination with OT slightly increased the sensitivity of *S. epidermidis* biofilm to OT (FIG. 10). Thus, the DispersinB™ and OT combination had a slightly enhanced effect on biofilm-embedded *S. epidermidis*.

Example 11

Figure 11:
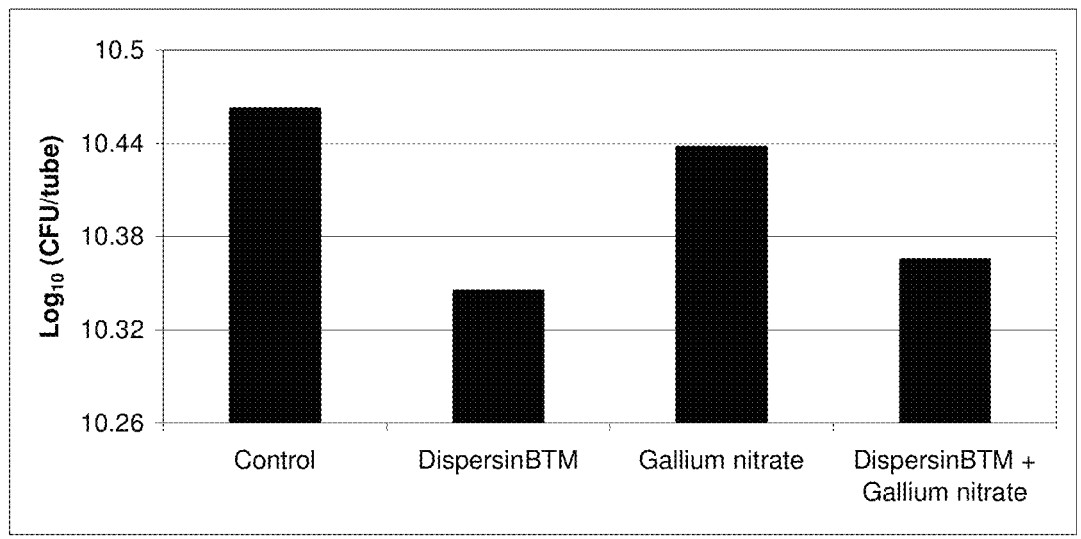
FIG. 11 is bar graph showing an enhanced effect of DispersinB™ on the sensitivity of biofilm-embedded *S. epidermidis* to gallium (III) nitrate. *S. epidermis* growth was measured in media with no antimicrobials (control), DispersinB™ (20 µg/ml), gallium (III) nitrate (5 mg/ml), and a combination of DispersinB™ (20 µg/ml) and gallium (III) nitrate (5 mg/ml).

Effect of DispersinB™ on the Sensitivity of *Staphylococcus epidermidis* Biofilm to Gallium (III) Nitrate An in vitro biofilm dispersal assay was performed to determine the effect of DispersinB™ on enhancing the sensitivity of *S. epidermidis* biofilm to gallium (III) nitrate. *S. epidermidis* biofilm grown in 1.5 ml polypropylene microcentrifuge tubes was rinsed with 200 µl of fresh medium and then treated with 200 µl medium containing 5 mg/ml of gallium (III) nitrate and/or 50 µg/ml of DispersinB™. Biofilm detachment and plating biofilm embedded cells were performed as described in Example 5. DispersinB™ in combination with gallium (III) nitrate did not increase the sensitivity of *S. epidermidis* biofilm to gallium (III) nitrate (FIG. 11). Thus, DispersinB™ and gallium (III) nitrate combination did not have an enhanced inhibitory effect on biofilm-embedded *S. epidermidis*.

Example 12

Figure 12:
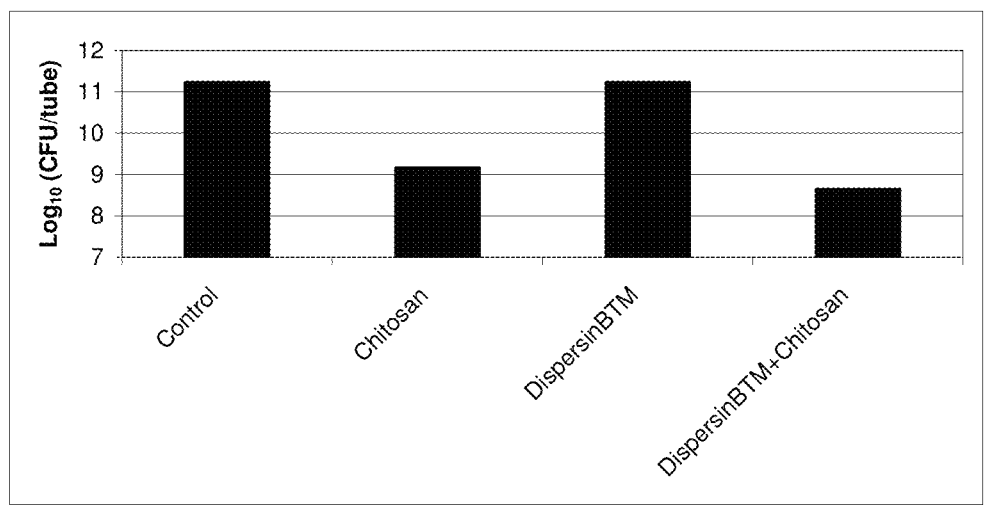
FIG. 12 is bar graph showing an enhanced effect of DispersinB™ on the sensitivity of biofilm-embedded *S. epidermidis* to chitosan. *S. epidermidis* growth was measured in media with no antimicrobials (control), DispersinB™ (20 µg/ml), chitosan (2 mg/ml), and a combination of DispersinB™ (20 µg/ml) and chitosan (2 mg/ml).

Enhancing Effect of DispersinB™ on the Sensitivity of *Staphylococcus epidermidis* Biofilm to Chitosan An in vitro biofilm dispersal assay was performed to determine the effect of DispersinB™ on enhancing the sensitivity of *S. epidermidis* biofilm to chitosan. *S. epidermidis* biofilm grown in 1.5 ml polypropylene microcentrifuge tubes was rinsed with 200 µl of fresh medium and then treated with 200 µl medium containing 2 mg/ml of chitosan and/or 20 µg/ml of DispersinB™. Biofilm detachment and plating biofilm embedded cells were performed as described in Example 5. DispersinB™ in combination with chitosan slightly increased the sensitivity of S. epidermidis biofilm to chitosan (FIG. 12). Thus, the DispersinB™ and chitosan combination had a slightly enhanced inhibitory effect on biofilm-embedded *S. epidermidis*.

Example 13

Effect of DispersinB™ and Epigallocatechin Gallate (EGCG) on Biofilm Formation of *Staphylococcus epidermidis* and *Staphylococcus aureus*

Figure 13:
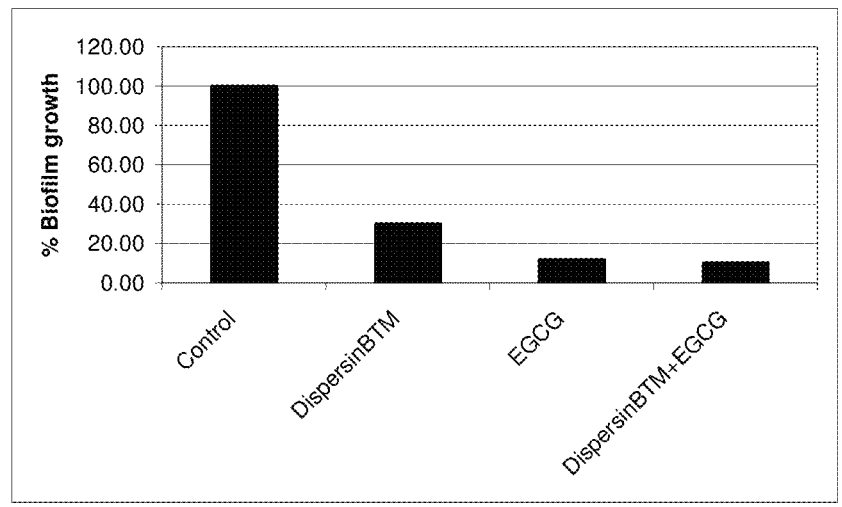
FIG. 13 is bar graph showing an effect of DispersinB™ and Epigallocatechin gallate (EGCG) alone and in combination on *S. epidermidis* biofilm formation. *S. epidermidis* growth was measured in media with no antimicrobials (control), DispersinB™ (50 µg/ml), EGCG (100 ng/ml), and a combination of DispersinB™ (50 µg/ml) and EGCG (100 ng/ml).
Figure 14:
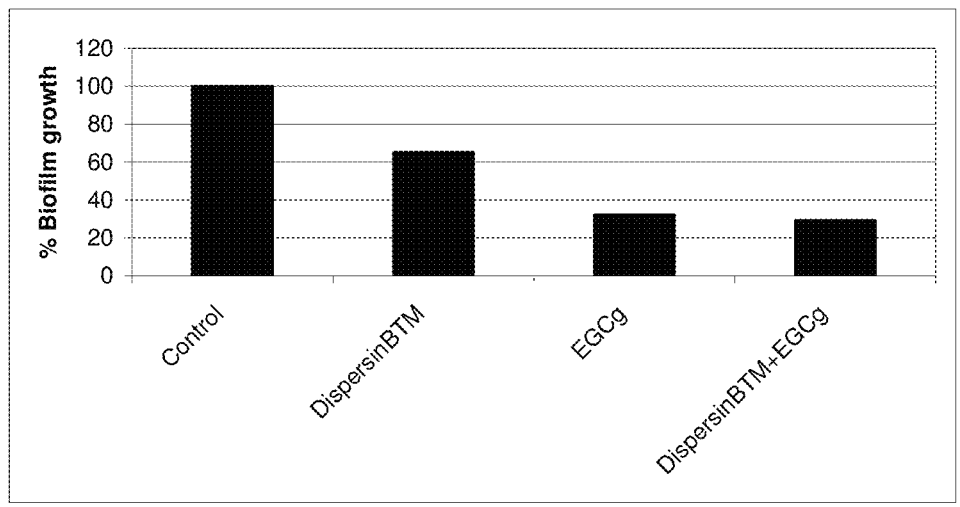
FIG. 14 is bar graph showing an effect of DispersinB™ and Epigallocatechin gallate (EGCG) alone and in combination on *S. aureus* biofilm formation. *S. aureus* growth was measured in conditions of no antimicrobials (control), DispersinB™ (50 µg/ml), EGCG (100 ng/ml), and a combination of DispersinB™ (50 µg/ml) and EGCG (100 ng/ml).

An in vitro microplate assays were performed to determine the effects of a DispersinB™ and EGCG combination on the growth of biofilm embedded *S. epidermidis* and *S. aureus*. Overnight cultures of each bacterial strain grown in Tryptic Soy Broth (TSB) were used as inoculum. Biofilm was developed in TSB on a 12-well microplate in the absence and presence of each test compound (50 ng DispersinB™ or 100 ng/ml ECCG) separately and together (DispersinB™+EGCG). The plates were incubated at 37° C. for 24 hours. Medium containing planktonic cells in each well was removed gently and rinsed with sterile water. A known volume of water was added to each well and sonicated for 30 seconds. The contents of each well was transferred into a sterile tube, vortexed for a minute, followed by 10-fold serial dilution, and plated on agar plates using a spreader. After incubating the plates at 37° C. for 24 hours, colony forming units (CFU) were counted. Although EGCG was more effective than DispersinB™ in inhibiting the growth of biofilm embedded test microorganisms, together the combination of DispersinB™ and ECCG did not have an enhanced inhibitory effect on biofilm-embedded *S. epidermidis* and *S. aureus* (FIGS. 13 and 14).

Example 14

Figure 15:
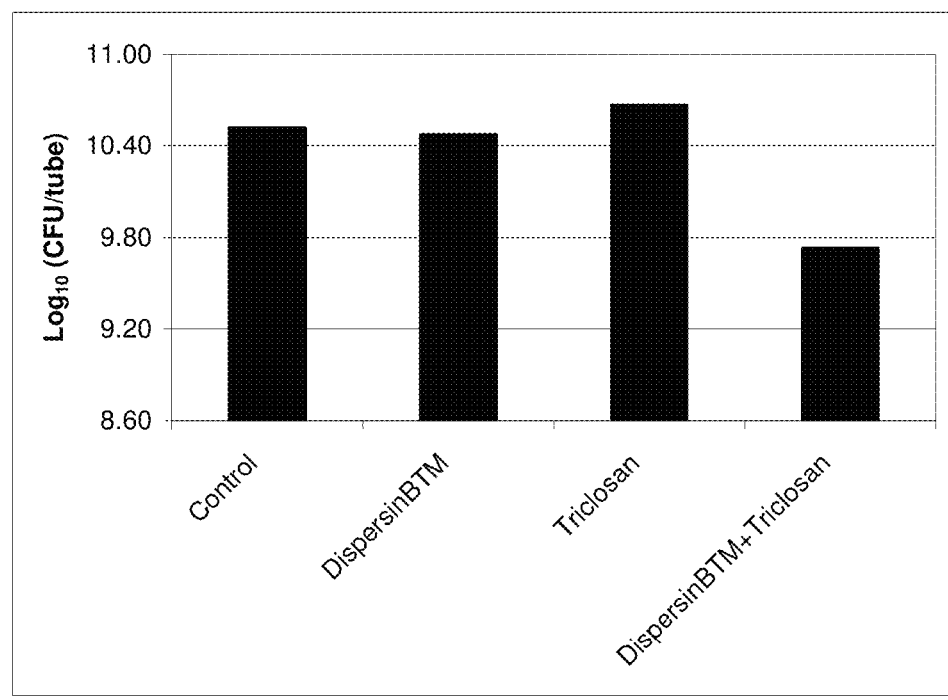
FIG. 15 is bar graph showing an effect of DispersinB™ and triclosan alone and in combination on biofilm-embedded *S. epidermidis*. *S. epidermidis* growth was measured in media with no antimicrobials (control), DispersinB™ (20 µg/ml), triclosan (1 mg/ml), and a combination of DispersinB™ (20 µg/ml) and EGCG (1 mg/ml).

DispersinB™ Increased the Sensitivity of Biofilm-Embedded *Staphylococcus epidermidis* to Triclosan An in vitro biofilm dispersal assay was performed to determine the effect of DispersinB™ on the sensitivity of a *S. epidermidis* biofilm to triclosan. A *S. epidermidis* biofilm grown in 1.5 ml polypropylene microcentrifuge tubes was rinsed with 200 µl of fresh medium and then treated with 200 µl medium containing 1 mg/ml of triclosan and/or 20 µg/ml of DispersinB™. A biofilm dispersal assay was performed as described in the Example 5. When DispersinB™ was used in combination with triclosan, sensitivity of biofilm-embedded *S. epidermidis* to triclosan increased (FIG. 15). The DispersinB™ and triclosan combination had an enhanced inhibitory effect on biofilm-embedded *S. epidermidis*.

Example 15

Figure 16:
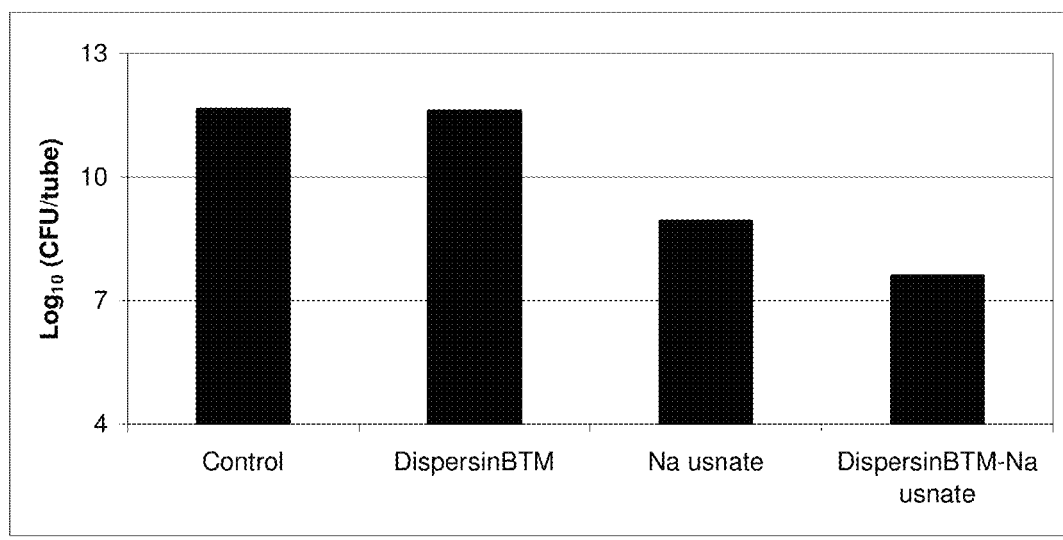
FIG. 16 is bar graph showing an effect of DispersinB™ and sodium (Na) usnate alone and in combination on biofilm-embedded *S. epidermidis*. *S. epidermidis* growth was measured in media with no antimicrobials (control), DispersinB™ (50 µg/ml), Na usnate (500 µg/ml), and a combination of DispersinB™ (50 µg/ml) and Na usnate (500 µg/ml).

Enhancing Effect of DispersinB™ on the Sensitivity of Biofilm-Embedded *Staphylococcus epidermidis* to Sodium Usnate An in vitro biofilm dispersal assay was performed to determine the effect of DispersinB™ on the sensitivity of *S. epidermidis* biofilm to sodium usnate. A *S. epidermidis* biofilm grown in 1.5 ml polypropylene microcentrifuge tubes was rinsed with 200 µl of fresh medium and then treated with 200 µl medium containing 500 µg/ml of sodium usnate and/or 50 µg/ml of DispersinB™. A biofilm dispersal assay was performed as described in Example 5. When DispersinB™ was used in combination with sodium usnate, the sensitivity of biofilm-embedded *S. epidermidis* to sodium usnate increased (FIG. 16). The DispersinB™ and sodium usnate combination had an enhanced effect on biofilm-embedded *S. epidermidis*.

Example 16

Antimicrobial Activity of DispersinB™ and Triclosan (TCSN) Combination Against Clinical Isolates of Wound-Associated Pathogens The antimicrobial activity of DispersinB™ and triclosan combination was studied by determining the minimal inhibitory concentrations (MIC) in 96 well microtiter plates as described in Example 4. Triclosan in combination with DispersinB™ was active against all the pathogens tested (Table 2).

TABLE 2

MIC of triclosan in the presence of DispersinB ™, 40 µg/ml) enzyme for clinical isolates of wound-associated pathogens

| Cultures | MIC (µg/ml) |
| --- | --- |
| *S. aureus* Gav 16A | <0.39 |
| *S. aureus* 120 | <0.39 |
| *S. aureus* 68 | <0.39 |
| Coagulase-negative staphylococci (CNS 11) | 25 |
| CNS 82 | <0.39 |
| CNS 42 | 0.625 |

Example 17

Figure 17:
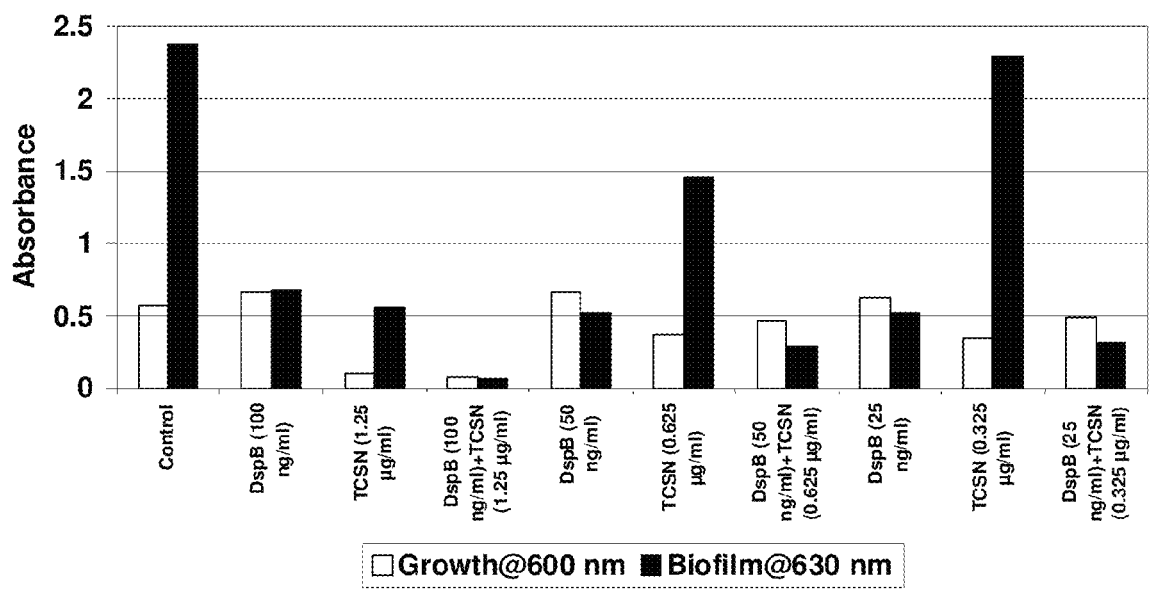
FIG. 17 is bar graph showing an enhanced inhibitory effect of DispersinB™ and Triclosan (TCSN) combination on coagulase-negative Staphylococci (CNS) biofilm formation. Planktonic (□) and biofilm growth (■) were measured in media with no antimicrobials (control), DispersinB™ (25, 50, and 100 ng/ml), TCSN (0.325, 0.625, and 1.25×g/ml), and a combination of DispersinB™ (25, 50, and 100 ng/ml) and TCSN 0.325, 0.625, and 1.25 µg/ml).

Enhanced Inhibitory Effect of DispersinB™ and Triclosan (TCSN) Combination on Coagulase-Negative Staphylococci (CNS) Biofilm An in vitro microplate assay was performed to determine the effect of DispersinB™ and triclosan combination on the growth and biofilm formation of coagulase-negative Staphylococci-42 (CNS-42). The experiment was performed as explained in Example 1. The combination of DispersinB™ and TCSN (100 ng/ml+1.25 µg/ml, respectively) showed enhanced inhibitory effect on CNS-42 biofilm formation (FIG. 17).

Example 18

Figure 18:
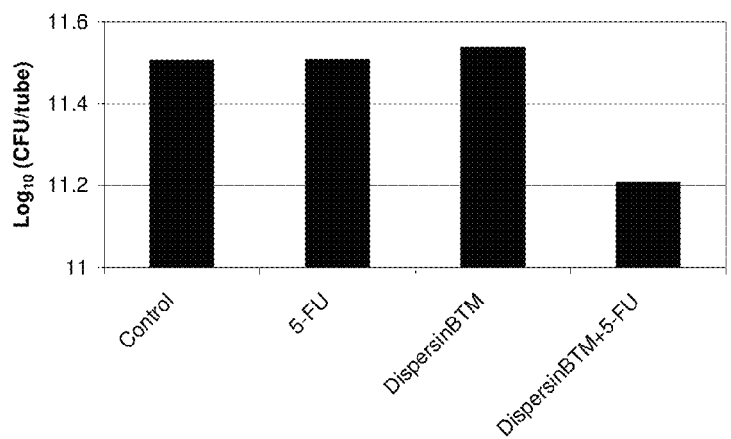
FIG. 18 is bar graph showing enhanced effect of DispersinB™ on the sensitivity of biofilm-embedded *S. epidermidis* to 5-fluorouracil (5-FU). *S. epidermidis* growth was measured in media with no antimicrobials (control), DispersinB™ (20 µg/ml), 5-FU (100 µg/ml), and a combination of DispersinB™ (20 µg/ml) and 5-FU (100 µg/ml).

Enhancing Effect of DispersinB™ on the Sensitivity of Biofilm-Embedded *Staphylococcus epidermidis* to 5-fluorouracil An in vitro biofilm dispersal assay was performed to determine the effect of DispersinB™ on the sensitivity of biofilm-embedded *S. epidermidis* to 5-fluorouracil (5-FU). *S. epidermidis* biofilm grown in 1.5 ml polypropylene microcentrifuge tubes was rinsed with 200 µl of fresh medium and then treated with 200 µl medium containing 100 µg/ml of 5-FU and/or 20 µg/ml of DispersinB™. Biofilm detachment and plating biofilm embedded cells were performed as described in Example 5. When DispersinB™ was used in combination with 5-FU, there was increased sensitivity of biofilm-embedded *S. epidermidis* to 5-FU (FIG. 18). Thus, the DispersinB™ and 5-FU combination had an enhanced inhibitory effect on biofilm-embedded *S. epidermidis*.

Example 19

Figure 19:
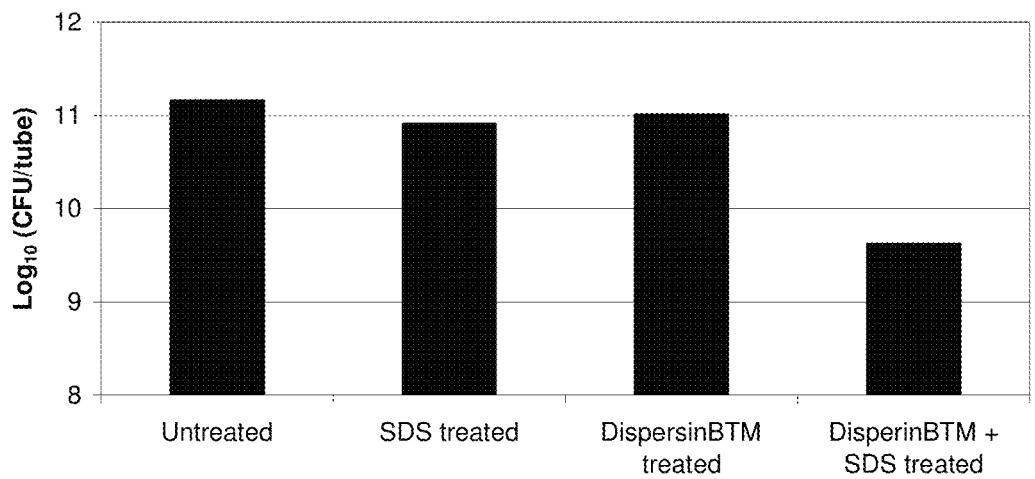
FIG. 19 is bar graph showing the increased susceptibility of biofilm-embedded *S. epidermidis* pretreated with DispersinB™ to killing by sodium dodecyl sulfate (SDS). *S. epidermidis* growth was measured in media with no antimicrobials (control), DispersinB™ (20 µg/ml), SDS (0.2 mg/ml), and a combination of DispersinB™ (20 µg/ml) and SDS (0.2 mg/ml).

Increased Susceptibility of Biofilm-Embedded *Staphylococcus epidermidis* Pretreated with DispersinB™ to Killing by SDS An in vitro biofilm assay was performed to determine the effect of DispersinB™ pre-treatment on the susceptibility of *S. epidermidis* to SDS. *S. epidermidis* biofilm grown in tubes were pretreated with PBS or DispersinB™ (20 µg/ml) for 30 min, and then treated with SDS (0.2 mg/ml) for 5 min at 37° C. The untreated, DispersinB™ alone, or SDS alone did not significantly kill biofilm-embedded *S. epidermidis* (FIG. 19). However, SDS caused a 1.5 log unit decrease in the number of CFUs in tubes pretreated with DispersinB™ pre-treatment made biofilm embedded cells more susceptible to SDS. This shows that sequential application of DispersinB™ enzyme and an antimicrobial agent is possible, when an antimicrobial agent is not compatible with the enzyme.

Example 20

Increased Susceptibility of Biofilm-Embedded *Staphylococcus epidermidis* Pretreated with DispersinB™ to Killing by Chlorhexidine (CHX)

Figure 20:
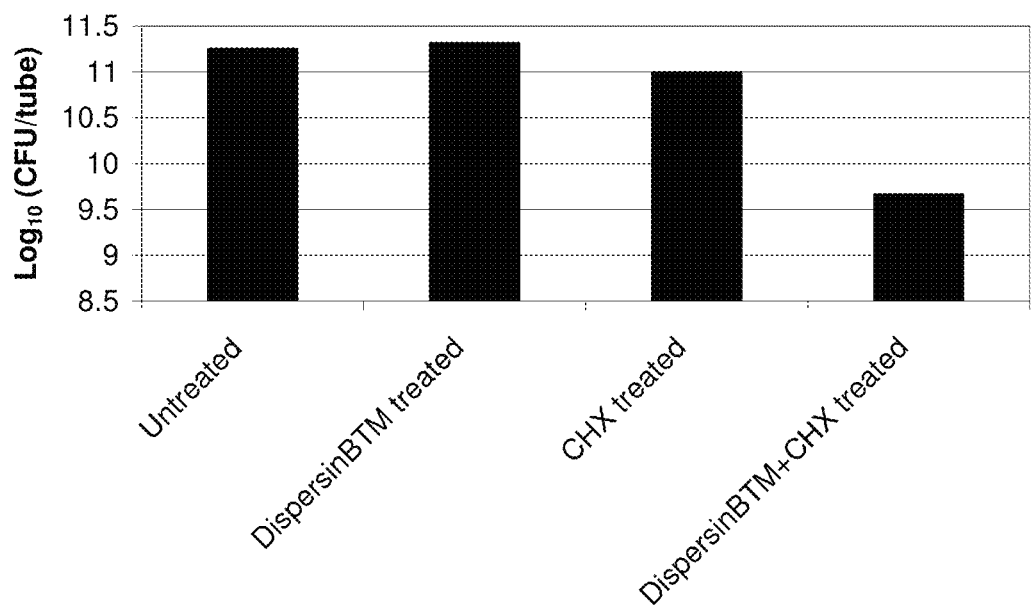
FIG. 20 is bar graph showing the increased susceptibility of biofilm-embedded *S. epidermidis* pretreated with DispersinB™ to killing by chlorhexidine (CHX). *S. epidermidis* growth was measured in media with no antimicrobials (control), DispersinB™ (20 µg/ml), CHX (0.2 µg/ml), and a combination of DispersinB™ (20 µg/ml) and CHX (0.2 µg/ml).

An in vitro biofilm assay was performed to determine the effect of DispersinB™ pre-treatment on the susceptibility of biofilm-embedded *S. epidermidis* to CHX. *S. epidermidis* biofilm grown in tubes were pretreated with PBS or DispersinB™ (20 µg/ml) for 30 min, and then treated with CHX (0.2 µg/ml) for 5 min at 37° C. The untreated, DispersinB™ alone, or CHX alone did not significantly kill *S. epidermidis* biofilm (FIG. 20). However, CHX caused a 1.6 log decrease of CFU in tubes pretreated with DispersinB™. DispersinB™ pre-treatment made biofilm-embedded cells more susceptible to CHX. This shows that sequential application of DispersinB™ enzyme and an antimicrobial agent is possible, when an antimicrobial agent is not compatible with the enzyme.

Example 21

Increased Susceptibility of Biofilm-Embedded *Staphylococcus epidermidis* Pretreated with DispersinB™ to Killing by Benzalkonium Chloride (BKC)

Figure 21:
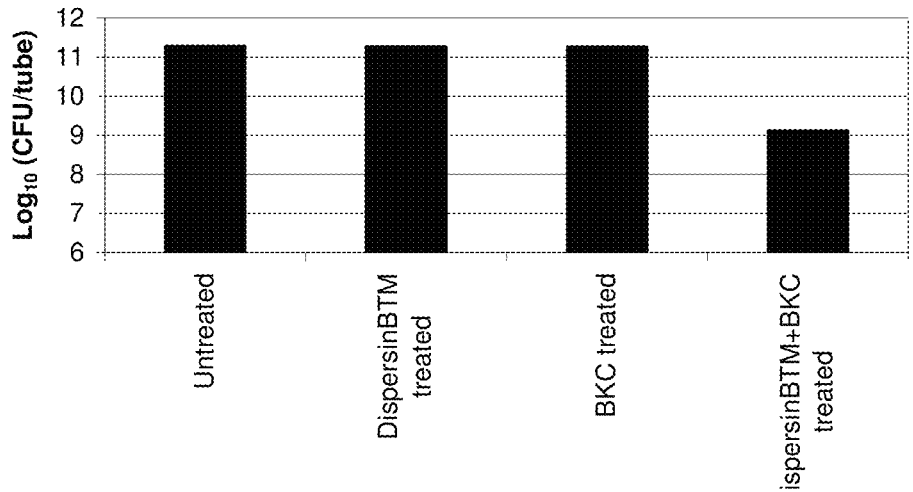
FIG. 21 is bar graph showing the increased susceptibility of biofilm-embedded *S. epidermidis* pretreated with DispersinB™ to killing by benzalkonium chloride (BKC). *S. epidermidis* growth was measured in media with no antimicrobials (control), DispersinB™ (20 µg/ml), BKC (0.4 µg/ml), and a combination of DispersinB™ (20 µg/ml) and BKC (0.4 µg/m).

An in vitro biofilm assay was performed to determine the effect of DispersinB™ pre-treatment on the susceptibility of *S. epidermidis* to BKC. *S. epidermidis* biofilm grown in tubes were pretreated with PBS or DispersinB™ (20 µg/ml) for 30 min, and then treated with BKC (0.4 µg/ml) for 60 min at 37° C. The untreated, DispersinB™ alone, or BKC alone did not significantly kill biofilm-embedded *S. epidermidis* (FIG. 21). However, BKC caused a 2.2 log decrease in CFU in tubes pretreated with DispersinB™. DispersinB™ pre-treatment made biofilm-embedded cells more susceptible to BKC. This shows that sequential application of DispersinB™ enzyme and an antimicrobial agent is possible, when an antimicrobial agent is not compatible with the enzyme.

Example 22

Enhanced Inhibitory Effect of DispersinB™ and EDTA Combination on Biofilm-Embedded *Staphylococcus epidermidis*

Figure 22:
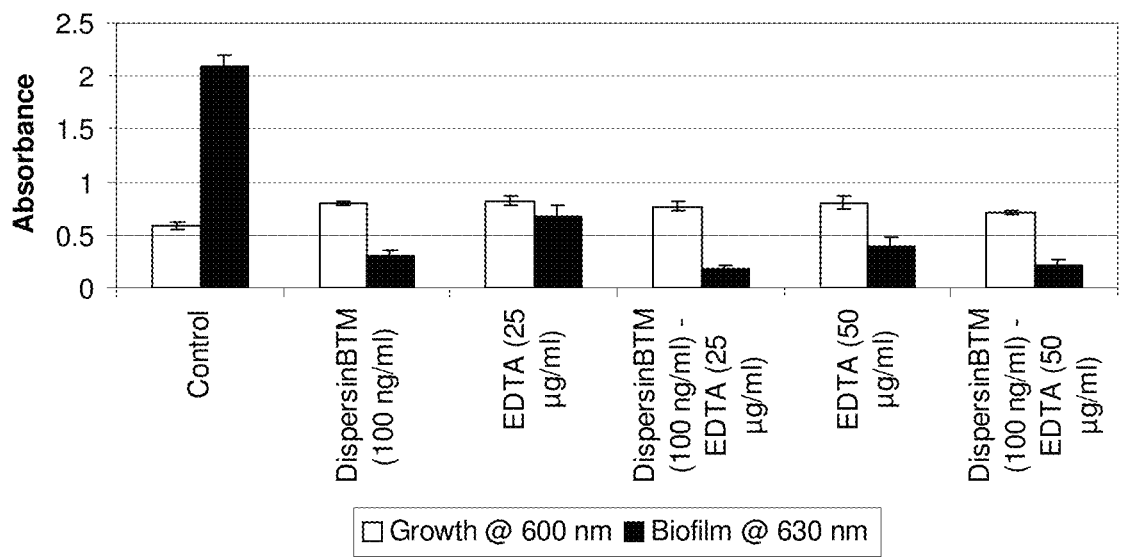
FIG. 22 is bar graph showing an enhanced inhibitory effect of DispersinB™ and EDTA combination on *S. epidermidis* biofilm formation. Planktonic (□) and biofilm (■) *S. epidermidis* growth was measured in media with no antimicrobials (control), DispersinB™ (100 ng/ml), EDTA (25 and 50 µg/ml), and combinations of DispersinB™ (100 ng/ml) and EDTA (25 or 50 µg/ml).

An in vitro biofilm assay was performed to determine the effect of DispersinB™ and EDTA on the growth and biofilm formation of *S. epidermidis*. The experiment was performed as explained in Example 1. The 100 ng/ml DispersinB™ in combination with EDTA at two concentrations such as 25 µg/ml and 50 µg/ml showed enhanced inhibitory effect on *S. epidermidis* biofilm formation (FIG. 22).

Example 23

Increased Susceptibility of Biofilm-Embedded *Staphylococcus epidermidis* Pretreated with DispersinB™ to Killing by Silver Nanopowder (SNP)

Figure 23:
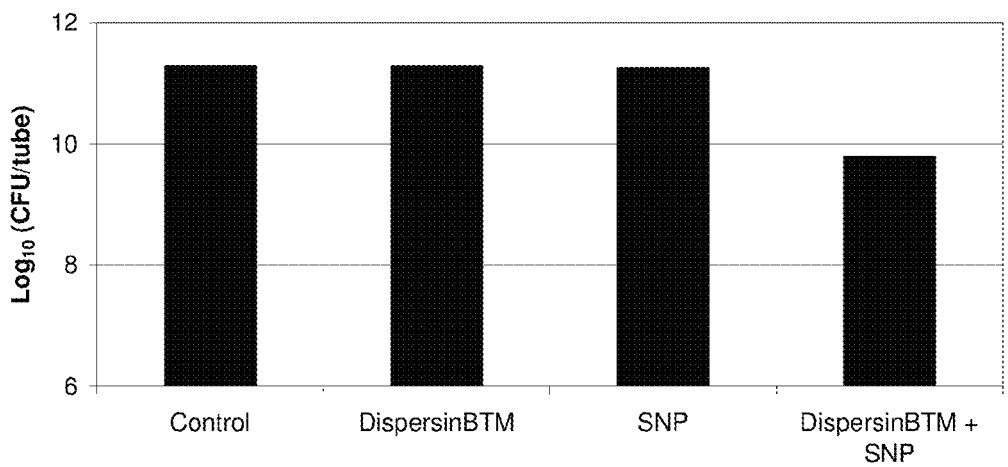
FIG. 23 is bar graph showing the increased susceptibility of biofilm-embedded *S. epidermidis* pretreated with DispersinB™ to killing by silver nanopowder (SNP). *S. epidermidis* growth was measured in media with no antimicrobials (control), DispersinB™ (20 µg/ml), SNP (0.03125 µg/ml), and a combination of DispersinB™ (20 µg/ml) and SNP (0.03125 µg/ml).

An in vitro biofilm assay was performed to determine the effect of DispersinB™ pre-treatment on susceptibility of *S. epidermidis* to silver nanopowder (SNP). *S. epidermidis* biofilm grown in tubes were pretreated with PBS or DispersinB™ (20 µg/ml) for 30 min, and then treated with SNP (0.03125 µg/ml) for 60 min at 37° C. The untreated, DispersinB™ alone, or SNP alone did not significantly kill biofilm-embedded *S. epidermidis* (FIG. 23). However, SNP caused a 1.5 log decrease in CFU in tubes pretreated with DispersinB™. DispersinB™ pre-treatment made biofilm embedded cells more susceptible to SNP treatment. This shows sequential application of DispersinB™ enzyme and an antimicrobial agent is possible, when an antimicrobial agent is not compatible with the enzyme.

Example 24

Enhanced Susceptibility of Biofilm-Embedded *E. coli* to a Combination Therapy of DispersinB™ and Bacteriophage An *E. coli* biofilm was tested for survival after treatment with bacteriophage, DispersinB™, a bacteriophage cocktail, and a combination of DispersinB™ and a bacteriophage cocktail.

*E. coli* TRMG1655 [csrA::kan$^r$] strain was transformed with transposon, mini-TN5 luxCDABE::kan$^r$ for luciferase expression (Kadurugamuwa et al., 2005, *Infect. Immun.* 73: 3878-3887), and the operon integrated into the chromosome. Integration was confirmed by amplification of the genomic DNA upstream of the transposon by inverse PCR using Ssp1-digested genomic DNA. Primers UTCF1 (5'-GTGCAATC-CATTAATTTTGGTG-3'; SEQ ID NO:13) and UTCR (5'-CATACGTATCCTCCAAGCC-3'; SEQ ID NO:14) were used to amplify the upstream region using Pfu DNA polymerase (Sigma-Oligosynthesis, St. Louis, Mo.). The lux operon is derived from *Photorhabdus* luminescence and was obtained from Xenogen Inc. (Alameda, Calif.). These bioluminescent bacteria allow real-time monitoring by noninvasive imaging of biofilms, either in vitro or in vivo.

A cell suspension of $10^6$ *E. coli* csrA luxCDABE kan$^r$ was used to inoculate a filter disc (Millipore Corporation, Billerica, Mass.). The *E. coli* biofilm was maintained in minimal media (M9) supplemented with 50 μg/ml kanamycin and 100 μg/ml ampicillin. The media were changed every day by transferring the disc to new plate. After 3 days, chemoluminescence activity of the established biofilm was measured using a Typhoon™ imaging scanner (General Electric Healthcare Life Sciences) and ImageQuant TL software (Amersham Biosciences, Sunnyvale, Calif.). The measure luminescence directly correlates with the metabolic activity of the biofilm.

Luminescence was measured at day 0 and was used as the control. Following the measurement of luminescence at day 0, each disc was treated with one of the following—media alone (control) and media containing:

1) 50 μg/ml DispersinB™;
2) $10^8$ FF3;
3) $10^8$ K20;
4) $10^8$ T7;
5) $10^8$ U3;
6) a phage cocktail of $10^8$ of K20, FF3, T7, and U3; and
7) 50 μg/ml DispersinB™ plus a phage cocktail of total $10^8$ of K20, FF3, T7, and U3.

Figure 24:
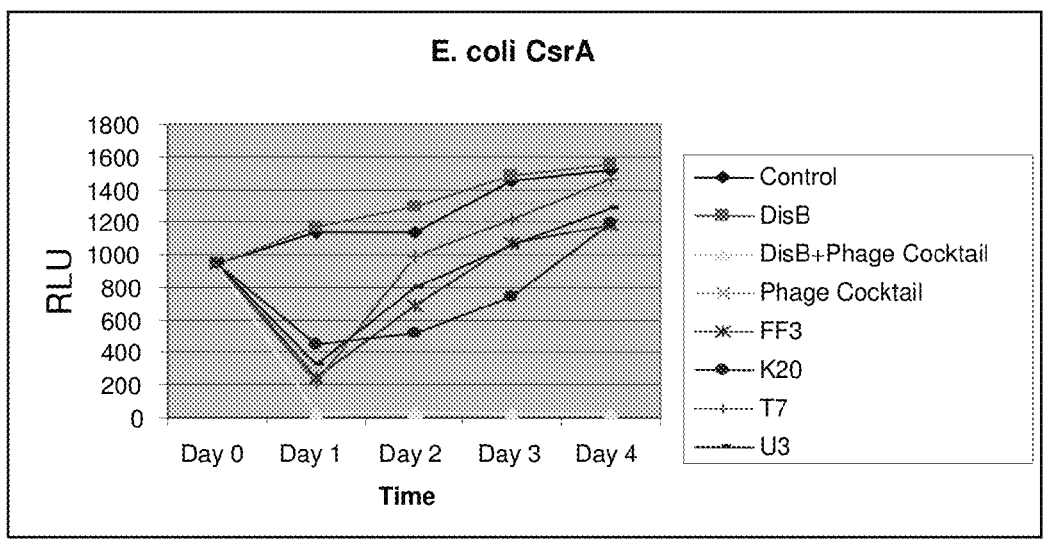
FIG. 24 is line graph showing the increased susceptibility of biofilm-embedded *E. coli* csrA luxCDABE kan$^r$ over time to a combination of DispersinB™ and a phage cocktail of FF3, K20, T7, and U3 (▲). Biofilm-embedded *E. coli* csrA luxCDABE kan$^r$ grown in media without antimicrobials or DispersinB™ was used as a control (◇). Biofilm-embedded *E. coli* csrA luxCDABE kan$^r$ treated with DispersinB™ only (■) had growth similar to the control. Biofilm-embedded *E. coli* csrA luxCDABE kan$^r$ were individually treated with phage FF3 (*), K20 (●), T7 (+), and U3 (−). Treatment with the phage produced a short term decrease in *E. coli* metabolic activity, but the *E. coli* metabolic activity returned to near control levels after 4 days. Biofilm-embedded *E. coli* csrA luxCDABE kan$^r$ treated with a phage cocktail of FF3, K20, T7, and U3 (X) alone produced similar results as the treatments with the individual phages.

Luminescence was measured every 24 hours followed by replacing the media. Thus, every 24 h following the measurement of the luminescence, 10 μl each of the different solutions was applied to the plate and the biofilm disc was placed on top of the drop everyday. The quantitative analysis of the biofilm luminescence from each day was used to compare the biofilm activity after treatment with the different treatments. Table 3 (corresponds to FIG. 24) provides the raw data as measured in relative light units (RLU These data show the relative increase or decrease in luminescence after the particular treatment.

TABLE 3

| Treatment | Day 0 | Day 1 | Day 2 | Day 3 | Day 4 |
|---|---|---|---|---|---|
| Control | 948.72 | 1131.8 | 1135.14 | 1447.05 | 1520.07 |
| DispersinB ™ | 948.72 | 1167.19 | 1297.42 | 1487.76 | 1550.01 |
| DispersinB ™ + Phage Cocktail | 948.72 | 24.42 | 29.48 | 22.72 | 18.99 |
| Phage Cocktail | 948.72 | 287.82 | 974.62 | 1308.72 | 1381.05 |
| FF3 | 948.72 | 252.72 | 684.26 | 1072.27 | 1186.36 |
| K20 | 948.72 | 449.21 | 522.73 | 742.37 | 1196.76 |
| T7 | 948.72 | 212.8 | 987.28 | 1217.28 | 1457.48 |
| U3 | 948.72 | 321.62 | 803.7 | 1057.51 | 1283.72 |

The experiments were repeated using the same *E. coli* strain csrA luxCDABE kan$^r$ and protocols. Biofilm discs were pulsed with media alone (control) and media containing:

1) BisEDT (50 μg/ml);
2) BisEDT (50 μg/ml) plus a phage cocktail of $10^8$ of K20, FF3, T7, and U3;
3) BisEDT (50 μg/ml) plus 50 μg/ml DispersinB™;
4) BisEDT (50 μg/ml) plus 50 μg/ml DispersinB™ plus a phage cocktail of $10^8$ of K20, FF3, T7, and U3;
5) a phage cocktail of $10^8$ of K20, FF3, T7, and U3;
6) 50 μg/ml DispersinB™; and
7) 50 μg/ml DispersinB™ plus a phage cocktail of $10^8$ of K20, FF3, T7, and U3.

TABLE 4

| | Day 0 | Day 1 | Day 2 | Day 3 | Day 4 |
|---|---|---|---|---|---|
| Control | 1815.26 | 2151.4 | 1864.41 | 2318.77 | 2096.8 |
| BisEDT | 1815.26 | 245.27 | 83.51 | 8.02 | 47.62 |
| BisEDT + Cocktail | 1815.26 | 256.32 | 25.11 | 2.53 | 13.1 |
| BisEDT + DispersinB ™ | 1815.26 | 4.11 | 32.08 | 13.35 | 5.52 |
| BisEDT + DispersinB ™ + Cocktail | 1815.26 | 0.22 | 3.16 | 6.7 | 22.77 |
| Cocktail | 1815.26 | 188.3 | 899.35 | 1485.75 | 2127.73 |
| DispersinB ™ | 1815.26 | 2137.73 | 1911.9 | 2982.02 | 2032.06 |
| DispersinB ™ + Cocktail | 1815.26 | 287.93 | 462.37 | 521.27 | 429.25 |

The data indicate that the combination of DispersinB™ and an antimicrobial agent, including phage), provides a longer term anti-biofilm effect. Phage therapy alone produces an initially large decrease in RLU followed by a steady increase over time back to control levels. However, the combination of DispersinB™ and phage therapy produces a sharp decrease in RLU, which is maintained over 4 days.

Example 25

Phage Display of DispersinB™

In the present work, we introduce biofilm dispersal capabilities to phage by expressing DispersinB™ on the phage surface (phage display of DispersinB™). This allows the production of DispersinB™ at the site of bacterial infections using phage replication machinery that infect bacteria, and controls specially targeted pathogenic bacteria. Choosing a lytic phage for displaying DispersinB™ helps to dissolve bacterial biofilms and facilitate the movement of phage to a host organism. Conversely, using a temperate phage (lysogenic) for displaying DispersinB™ would not eliminate host bacteria but allow constant multiplication of phage-displayed DispersinB™ at the infection site and thereby helping to dissolve bacterial biofilm more rapidly. Once the biofilm is dissolved, the bacteria at the infection site are easily accessible to antimicrobial compounds and phages.

Application of phage-displayed DispersinB™ has certain advantages over purified DispersinB™ for infection control. In general, phages replicate at the site of infection and are available in abundance where they are most required (Smith & Huggins, 1982). Use of phage displayed DispersinB™ eliminates time consuming, expensive and elaborate purification process that is required for production of pure DispersinB™. Purified DispersinB™ has a shelf life of approximately 12 months. Once phage-displayed DispersinB™ is applied to an infection site, the phage should multiply exponentially using existing host bacteria, and progressively and effectively dissolve the biofilm by reaching its deeper layers. As an additional advantage, displaying DispersinB™ on lytic phages facilitates lytic phage to dissolve biofilm and kill biofilm-embedded bacteria. Furthermore, a specifically targeted bacterial species can be eliminated and biofilm can be dissolved by choosing specific lytic phages to display DispersinB™.

The lytic phage λ and the lysogenic phage M13 are modified to display DispersinB™ on their surfaces to test this hypothesis.

Materials and Methods
Creation of Recombinant Phage λ, M13, and Plasmid Vectors for DispersinB™ Display Head decorating protein gene D (gpD) and left arm fragments (nucleotide position 1-100086, and 20040-33498) of bacteriophage λ, lamB gene of *E. coli*, rrnB terminator sequence of plasmid vector pQE60, gene VIII and III sequences of M13 phage, DispersinB™ gene of *A. actinomycetemcomitans* are amplified by PCR. Specific restriction sites, linker sequence (GGGSGGGS), and $P_{tac}$ sequences are incorporated to PCR fragments with oligonucleotide primers.

The pfu DNA polymerase, Klenow fragment of DNA polymerase, and restriction endonucleases are purchased from MBI Fermentas (Burlington, ON, Canada). T4 DNA ligase and Shrimp Alkaline Phosphotase (SAP) are from New England Biolabs (Mississauga, ON, Canada) and Roche Diagnostics (Laval, QC, Canada), respectively. Synthetic oligonucleotides are obtained from Sigma Genosys (Oakville, ON, Canada). All enzymatic reactions and in vitro packaging are performed according to manufacturers' instructions. *E. coli* cells are transformed by heat shock using frozen competent cells prepared using calcium chloride method described in *Molecular Cloning* (Sambrook et al., 2001). Plasmid DNA is extracted from *E. coli* following the alkaline lysis method of Sambrook et al. (1989). Bacteriophage DNA is extracted following the proteinase K and SDS method described in *Molecular Cloning* (2001). A Initially the recombinant bacteriophage M13-VIII DispersinB™ and M13-III DispersinB™ are introduced to host bacteria by electroporation.

Figure 25:
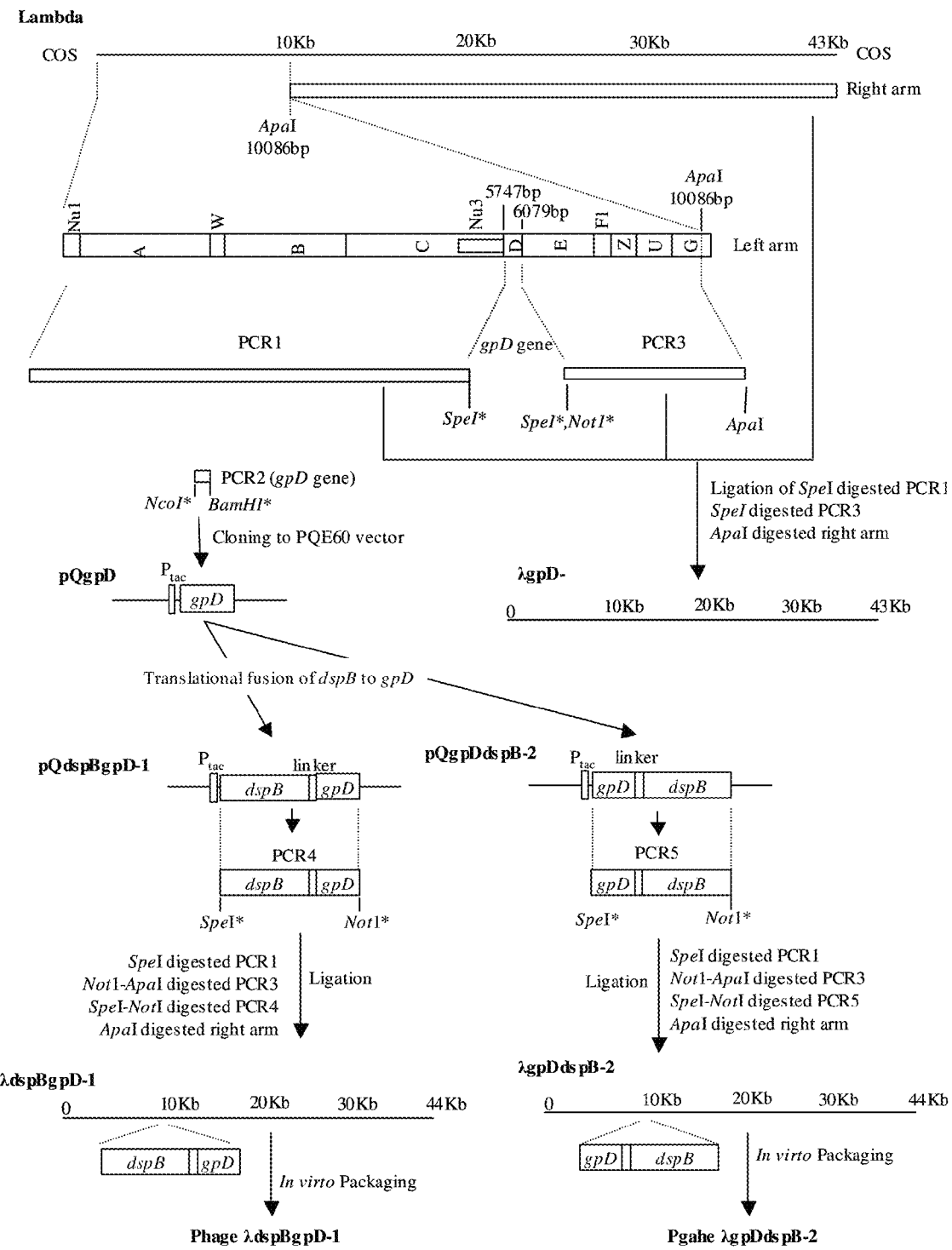
FIG. 25 is a schematic diagram of the construction of recombinant λ phage for DispersinB™ display.
Figure 26:
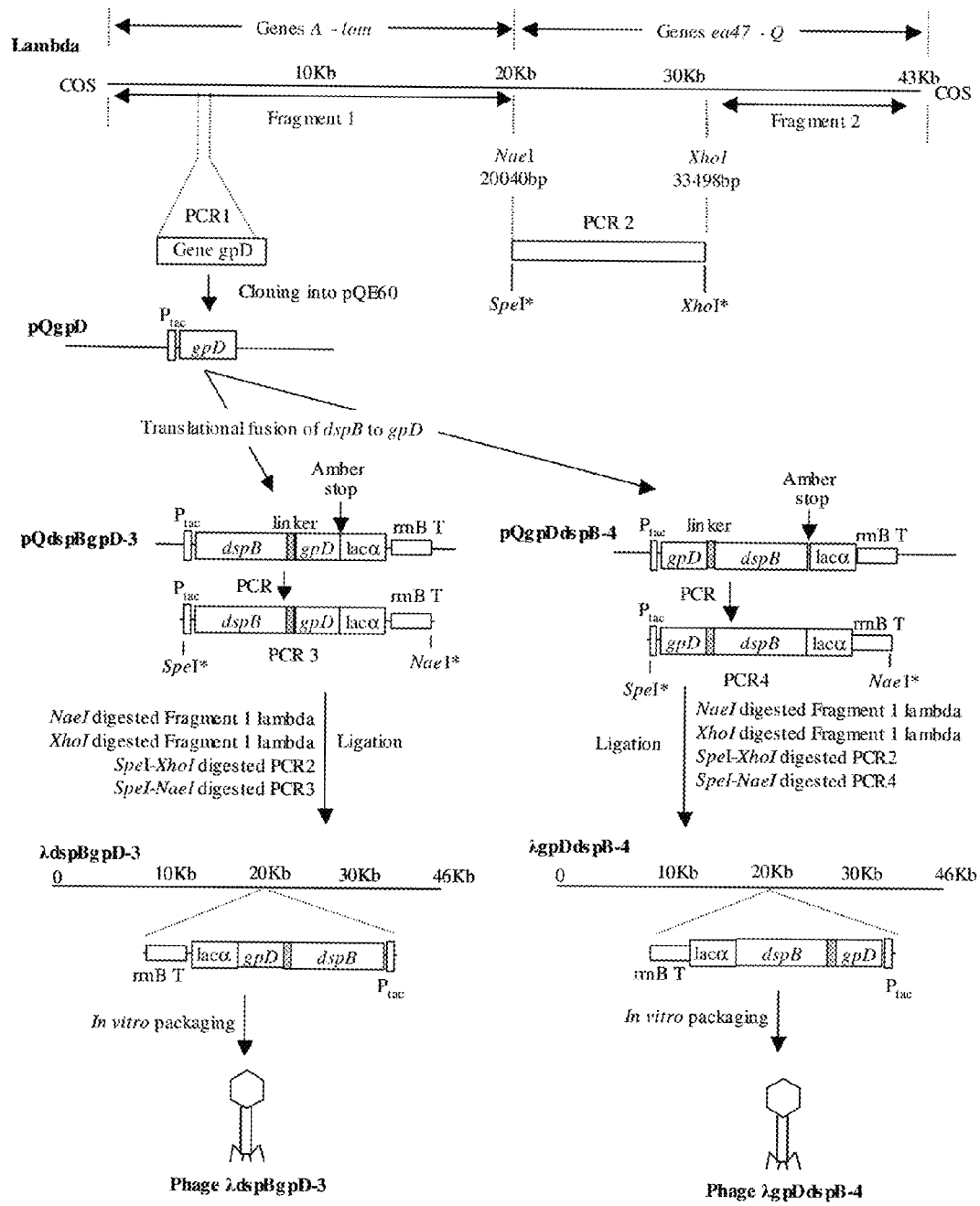
FIG. 26 is a schematic diagram of the construction of recombinant λ phage for DispersinB™ display.
Figure 27:
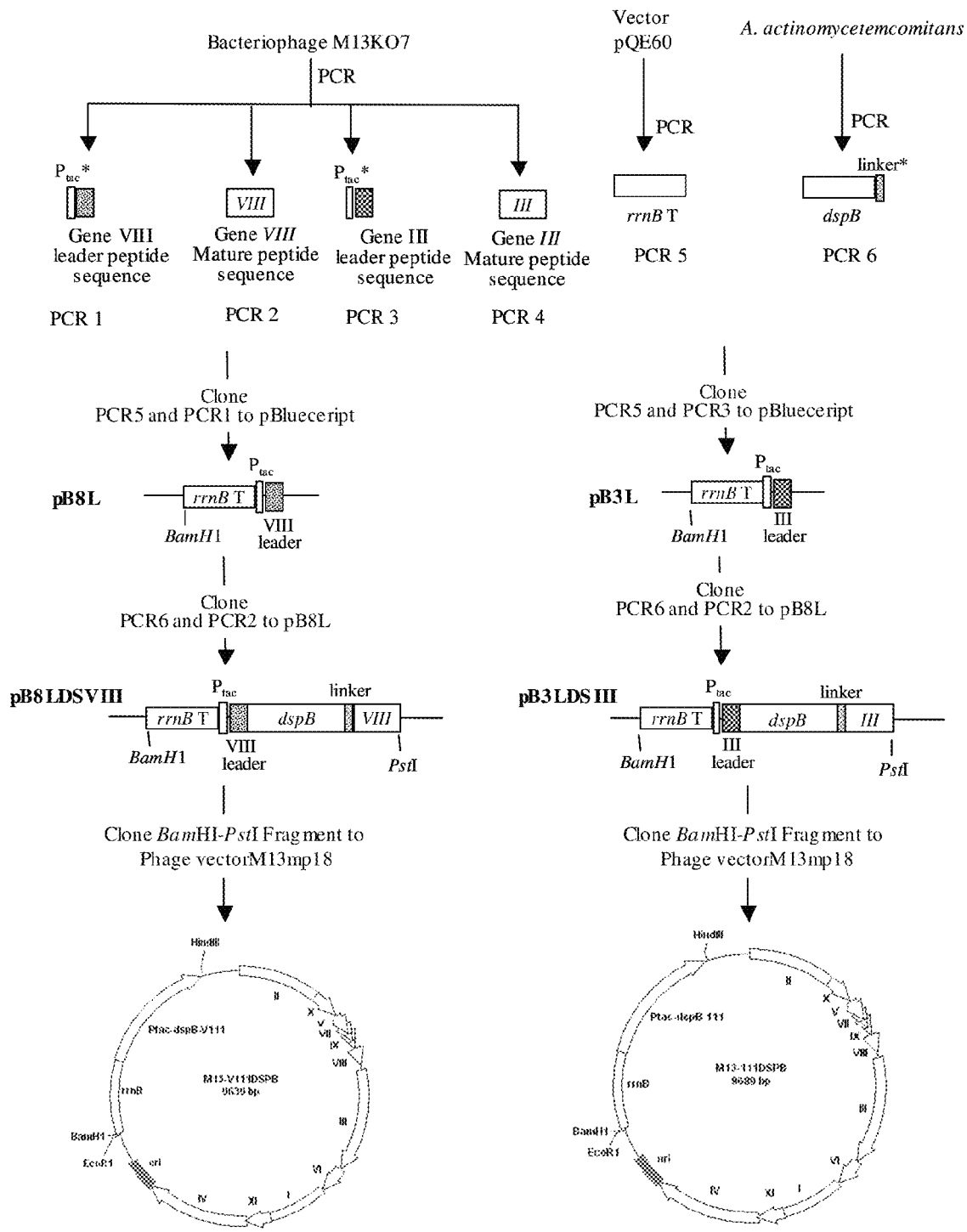
FIG. 27 is a schematic diagram of the construction of recombinant M13 phage for DispersinB™ display.

Plasmid $p^{QDispersinB_{TM}gpD-1}$ and $p^{QgpDDispersinB_{TM}-2}$ are high copy number plasmids with cloned DispersinB™ fused to the N-terminus and C-terminus, respectively, of gpD gene and expression is controlled in both plasmids by the $P_{tac}$ promoter (FIG. 25). To aid purification of the fusion protein, the DispersinB™ gene in vectors $p^{QDispersinB_{TM}gpD-1}$ and $p^{QgpDDispersinB_{TM}-2}$ carry a histidine tag (6×His) at their N- and C-terminus, respectively. λDispersinB™gpD$^{-1}$ and λgpD DispersinB™$^{-2}$ develop by incorporating promoterless DispersinB™-gpD and gpD-DispersinB™ fusion cassettes of $p^{QDispersinB_{TM}gpD-1}$ and $p^{QgpDispersinB_{TM}-2}$, respectively. In both λ DispersinB™ gpD$^{-1}$ and λgpD DispersinB™$^{-2}$, the expression of the DispersinB™ fusion peptide is under the expression signal of the original gpD promoter. Since the gpD gene of phage λ DispersinB™gpD$^{-1}$ and λgpD DispersinB™$^{-2}$ are replaced with DispersinB™-gpD, 100% of head decorating protein molecules carry DispersinB™ as a displayed protein. Phage λgpD- is defective in infection since the gpD gene is deleted. λgpD- can become infective by trans supply of the D protein. Therefore, λgpD- is used for screening expression cassettes (i.e. $p^{QDispersinB_{TM}gpD-1}$, $p^{QgpDDispersinB_{TM}-2}$, $p^{QDispersinB_{TM}gpD-3}$, $p^{QgpDDispersinB_{TM}-4}$) that produce the DispersinB™-gpD fusion (FIGS. 25 and 26). Plasmids $p^{B8LDSVIII}$ and $p^{B3LDSIII}$ are high copy number plasmids that carry DispersinB™ inserted between the leader sequence and the sequence that codes for the mature protein of coat proteins VIII and III, respectively, of phage M13 (FIG. 27). Both expression cassettes are under the control of the $P_{lac}$ promoter, and the rrnB terminator sequence is placed before the $P_{lac}$ promoter to terminate any transcription from upstream promoters. To aid purification of the fusion protein, the DispersinB™ gene in vectors $p^{B8LDSVIII}$ and $P^{B3LDSIII}$ carry a histidine tag (6×His) at their N terminus. Phage M13-VIII DispersinB™ and M13-III DispersinB™ carry the DispersinB™ expression cassettes of $p^{B8LDSVIII}$ and $p^{B3LDSIII}$ respectively (FIG. 27). Since both phages M13-VIII DispersinB™ and M13-III DispersinB™ also carry their wild type copy of genes VIII and II, only a fraction of major coat protein VII and minor coat protein II of M13-VIII DispersinB™ and M13-II DispersinB™, respectively, are fused to DispersinB™.

Growth of bacteria and Phage

All bacterial strains are cultured at 37° C. with agitation at 200 rpm in LB medium that contains 10 g/L each of bactotryptone, 10 g/L sodium chloride, and 5 g/L yeast extract in prepared in distilled deionized water.

Stocks of M13 phages are prepared by first inoculating 20 ml LB culture with 1 ml from a fresh overnight culture of host bacteria. The culture is shaken for 1 hr, after which $10^{10}$ plaque forming units (pfu) of the phage are added and the culture is shaken for an additional 3 hrs. The culture is cleared by centrifugation, and phage are precipitated by addition of 4% (w/v) polyethylene glycol (PEG) 8000 and 3% NaCl (w/v), incubating on ice for 1 hr, and centrifugation at 10000 rpm for 30 min. The phage pellet is resuspended in 1 ml PBS (50 mM phosphate, pH 7.2, 150 mM NaCl) and is microcentrifuged to pellet the debris. The supernatant containing phage is transferred to new tube.

Stocks of λ phages are prepared by infecting 0.1 ml fresh overnight culture of host bacteria cultured in LB with $10^6$ pfu of the phage in 50-100 μl volume. The infected culture is incubated for 20 min at 37° C. in 4 ml of LB with vigorous shaking until the cells are completely lysed, usually for 8-12 hrs. The lysate is supplemented with 100 μl of chloroform, incubating for 15 minutes at 37° C., and is centrifuged at 4000 g for 10 minutes at 4° C. The supernatant containing phage is separated and further purified by centrifugation through a glycerol step gradient (40% & 5%) at 35000 rpm for 60 minutes at 4° C.

The concentration of phage in final stocks is determined by extracting DNA and subjecting the samples to electrophoresis on 1% agarose gels, where known quantities of similar DNA is used as standards. Plaque-forming units per ml are calculated with soft agar overlay method.

Purification of DispersinB™ and DispersinB™-Phage Fusion Proteins

*E. coli* Tuner (DE3)pLacI are transformed with plasmids expressing DispersinB™. A single colony carrying transformed plasmid is cultured in 500 ml LB media containing 50 mg/L ampicillin and used for extraction of DispersinB™. Bacterial cells are harvested by centrifugation at 5000 rpm for 15 minutes, and the cell pellet is taken up in 20 ml of lysis buffer (20 mM Tris-HCl: (pH 8.0, 500 mM NaCl, 1 mM PMSF, 2 mg/ml lysozyme 0.1% Igepal®. Cells are disrupted by sonication three times, each 10 seconds at 30% capacity. The cell lysate is supplemented with RNaseA and DNaseI to a final concentration of 10 μg/ml and 5 μg/ml, respectively, and is incubated for 30 minutes at room temperature with gentle agitation. The cell debris is pelleted by centrifugation at 13000 rpm for 30 minutes, and the cleared lysate is used for isolation of DispersinB™ by Ni-affinity chromatography. The clear cell lysate is passed through a column packed with Ni-CAM™ HC Resin (10 cm pack volume) and is equilibrated with wash buffer (20 mM Tris-HCl (pH 8.0), 500 mM NaCl). The column is washed with 3 column volumes of wash buffer containing 5 mM immidazole followed by another 3 column volumes of wash buffer containing 20 mM immidazole. DispersinB™ is eluted in one ml fractions with 20 ml elution buffer (wash buffer containing 100 mM immidazole). DispersinB™ containing fractions are pooled and dialyzed against 4 L of 100 mM phosphate buffer (pH 5.9) containing 200 mM NaCl. Purified DispersinB™ is stored in storage buffer (50 mM Phosphate buffer (pH 5.9), 50 mM NaCl, 50% Glycerol) at −20° C.

DispersinB™ Enzyme Assay

The activity of DispersinB™ displayed on phage and purified DispersinB™ fusion peptides is measured by following the β-1,6-N-acetyl D-glucosaminidase (DispersinB™) assay as described by Kaplan et al. (2003, *J. Bacteriol.* 185: 4693-4698). The enzyme reaction is carried out in total 1 mL reaction volume that contains 500 μl of 10 mM substrate stock (5 mM 4-nitrophenyl N-acetyl-D-glucosaminide), 3.7 μg DispersinB™ solution or known volume of purified DispersinB™ display phage, 50 mM sodium phosphate buffer pH 5.9 containing 100 mM NaCl and dd$H_2O$ to bring the total reaction volume to 1 ml. The reaction mix is incubated at 30° C. for 30 min and supplemented with 5 μl of 10 N NaOH to stop enzyme reaction. The amount of p-nitrophenol produced in the reaction is determined spectrophotometrically at 405 nm using a standard curve constructed.

Cell Count Assay

A fresh overnight culture of bacteria grown in LB is diluted to 5% in LB, and 1.8 ml is added per well of 12-well tissue culture polystyrene plates (Corning Inc., New York, N.Y.). 200 μl of different dilutions of an aqueous test solution containing purified DispersinB™ or its fusion peptides or phages with or without displayed DispersinB™ are added per well individually. 200 μl water is added to negative control wells. After incubating for 24 hrs, the medium containing planktonic cells in each well is removed, and the biofilm is rinsed with PBS. After adding 2 ml of PBS to each well, the plate is sonicated for 1 minute, and the dislodged biofilm is mixed well with the pipette tip. The 1 ml suspension from each well is then serially diluted and 100 μl aliquots from each dilution are inoculated to LB plates. The plates are incubated at 37° C. for 24 hrs, and colonies are enumerated. Biofilm assay Fresh overnight grown cultures are diluted to 5% in LB medium, and 180 μl are added to each well of a 96-well microtitre plate (Corning Inc.). 20 μl of different dilutions of an aqueous test solution containing purified DispersinB™ or DispersinB™-phage fusion peptides or phages with or with out displayed DispersinB™ are added to microtiter plate wells individually. dd $H_2O$ serves as control. The plates are incubated at 37° C. for 16-18 h under stationary condition and the growth is measured at 600 μm. Biofilm formation is determined by measuring the absorbance at 630 nm. Biofilms are assayed by crystal violet staining, as described by Jackson et al. (2002, *J. Bacteriol.* 184: 290-301.).

Example 26

DispersinB™ in Combination with Detergents

A major component of the *A. actinomycetemcomitans* biofilm matrix is a hexosamine-rich polysaccharide that is functionally and genetically related to extracellular polysaccharide adhesins produced by *S. aureus*, *S. epidermidis*, *E. coli* and *A. pleuropneumoniae* (Kaplan et al., 2004). These polysaccharides, usually referred to as PNAG, PIA (polysaccharide intercellular adhesin), or PGA, consist of linear chains of N-acetyl-D-glucosamine (GlcNAc) residues in β(1, 6) linkage (hereafter referred to as PGA). PGA has been shown to play a role in abiotic surface attachment and intercellular adhesion (Wang et al., *J. Bacteriol.* 186: 2724-2734 (2004); Izano et al., *Microb. Pathogen.* 43: 1-9 (2007); Agladze et al., *J. Bacteriol.* 187: 8237-8246 (2005); Heilmann et al., *Mol. Microbiol.* 20: 1083-1091 (1996); McKenney et al., *Infect. Immun.* 66: 4711-4720 (1998)), protection from killing by antibiotics, antimicrobial peptides- and phagocytes (Izano et al., 2007; Vuong et al., *Cell. Microbiol.* 6: 269-275 (2004)) and virulence (Kropec et al., *Infect. Immun.* 73: 6868-6876 (2005)). In *A. actinomycetemcomitans*, PGA has been shown to mediate intercellular adhesion and resistance to killing by the anionic detergent sodium dodecyl sulfate (SDS) (Kaplan et al., 2004).

The effect of a detergent on the sensitivity of biofilm-embedded *A. actinomycetemcomitans* was investigated.

Methods

Reagents. Recombinant dispersinB protein was purified from an overexpressing strain of *E. coli* as previously described (Kaplan et al., *J. Bacteriol.* 2003, 185: 4693-4698). The enzyme had a specific activity of ~$10^3$ units per mg of protein. Sodium dodecyl sulfate (SDS) was purchased from Fluka (St. Gallen, Switzerland). Phosphate-buffered saline (PBS; 138 mM NaCl, 10 mM phosphate, 2.7 mM KCl, pH 7.4) was purchased from Sigma Chemical Company (St. Louis, Mo., USA).

Bacterial strains, media, and growth conditions. *A. actinomycetemcomitans* strain CU1000 (serotype f) was isolated from a 13-year-old African-American female with localized aggressive periodontitis (Fine et al., *Microbiol.* 1999, 145: 1335-1347). Strain CU1000 exhibits a rough-textured colony morphology on agar and a strong biofilm formation phenotype in broth, both of which are characteristic of fresh clinical isolates (Fine et al., 1999). An isogenic PGA mutant strain HW1018 (CU1000 pgaC::IS903φKan) was isolated by randomly mutagenizing CU1000 with transposon IS903φKan and selecting mutants that produced white colonies on Congo red agar, as previously described (Kaplan et al., 2003; Kaplan et al., *J. Bacteriol.* 2004, 186: 8213-8220). Like other pgaC mutant strains, HW1018 was completely deficient in PGA production, but still formed tenacious biofilms on plastic surfaces (Kaplan et al., 2004). Bacteria were grown in trypticase soy broth supplemented with 6 g yeast extract and 8 g/L glucose. Solid medium was supplemented with 15 g/L agar. All cultures were incubated statically at 37° C. in 10% $CO_2$.

Preparation of Inocula. Approximately 10 colonies from a 48-hour-old agar plate were transferred to a 15-mL polypropylene microcentrifuge tube containing 200 μL of fresh broth. The cells were homogenized with 10 strokes of a disposable pellet pestle (Kontes), transferred to a 15-mL conical centrifuge tube containing 2 mL of fresh broth, subjected to high-speed vortex agitation for 15 sec, and then passed through a 5-μm-pore-size PVDF syringe filter (Millipore). The resulting filtrate (~1 mL) contained >99% single cells at a concentration of $10^7$ to $10^8$ colony-forming units (CFU)/mL (Kaplan & Fine, *Appl. Environ. Microbiol* 2002, 68: 4943-4950).

Biofilm Cultures. Biofilms were grown in 17 mm×100 mm culture tubes (untreated polystyrene; Falcon #352051) or 96-well microtiter plates (tissueculture-treated polystyrene, flat bottoms; Falcon #353072). Culture vessels were inoculated with a 1:10 dilution of inoculum in fresh broth (1 mL for tubes or 200 μL for microplates) and incubated for 24 h.

Crystal Violet Assay. Biofilm biomass was visualized and quantitated by means of a crystal violet binding assay as previously described (Kaplan et al., *Antimicrob. Agents Chemother.* 2004, 48: 2633-2636). Briefly, biofilms were rinsed with water to remove loosely attached cells, stained for 1 min with Gram's crystal violet (200 μL for microplates and 1 mL for tubes), rinsed, dried, and photographed. For quantitation of biofilms grown in microplates, biofilms were destained with 200 μL of 33% acetic acid for 5 min, and the absorbance of the crystal violet solution was measured directly in the plate by means of a BioRad Benchmark microtiter plate-reader set at 590 nm. Crystal violet binds to bacterial biofilms, but not to polystyrene (O'Toole & Kolter, *Mol. Microbiol.* 1998, 28: 449-461).

Biofilm Detachment Assay. Biofilms were rinsed with water and treated with 200 µL (for microplates) or 1 mL (for tubes) of DispersinB™ (20 µg/mL in PBS) or SDS (0.001-1% in PBS). After a five- or 30-minute incubation at 37° C., biofilms were rinsed with water and stained with crystal violet as described above. In some assays, biofilms were first treated with DispersinB™ for 5 or 30 min, rinsed, and then treated with SDS. All detachment assays were performed in duplicate wells or tubes. All assays were performed on at least 3 separate occasions, with similar results.

Biofilm Killing Assay. Biofilms grown in polystyrene tubes as described above were washed 3 times with sterile PBS and then treated with 1 mL of SDS (0.01% in PBS) or cetylpyridinium chloride (CPC; 0.02% in PBS). After 5 ruin, the biofilms were rinsed 3 times with PBS to remove the SDS or CPC, and then treated with 1 mL of DispersinB™ (20 µg/mL in PBS) for 5 min to detach the cells. Tubes were vortexed for 10 s, and 20 µL aliquots of the detached biofilms were transferred to the wells of a flat-bottomed 96-well microtiter plate containing 180 µL of fresh broth. Five serial dilutions (20 µL into 180 µL) were performed directly into adjacent wells. Plates were incubated for 48 h and then rinsed and stained with crystal violet as described above. Wells containing 30-300 biofilm colonies were photographed under a dissecting microscope and counted. In some assays, biofilms were pre-treated with 1 mL of DispersinB™ (20 µg/mL in PBS) for 5 min prior to the SDS treatment. In these assays, a 100 µL quantity of SDS in PBS (at 10 times the test concentration) was added directly to the DispersinB™-treated cell suspension and mixed. After 5 min, tubes were vortexed briefly, and 20-µL aliquots of culture were enumerated as described above. Killing assays were performed in duplicate tubes on at least 5 separate occasions, with similar results.

Detachment of Biofilms by SDS and DispersinB™

Figure 28:
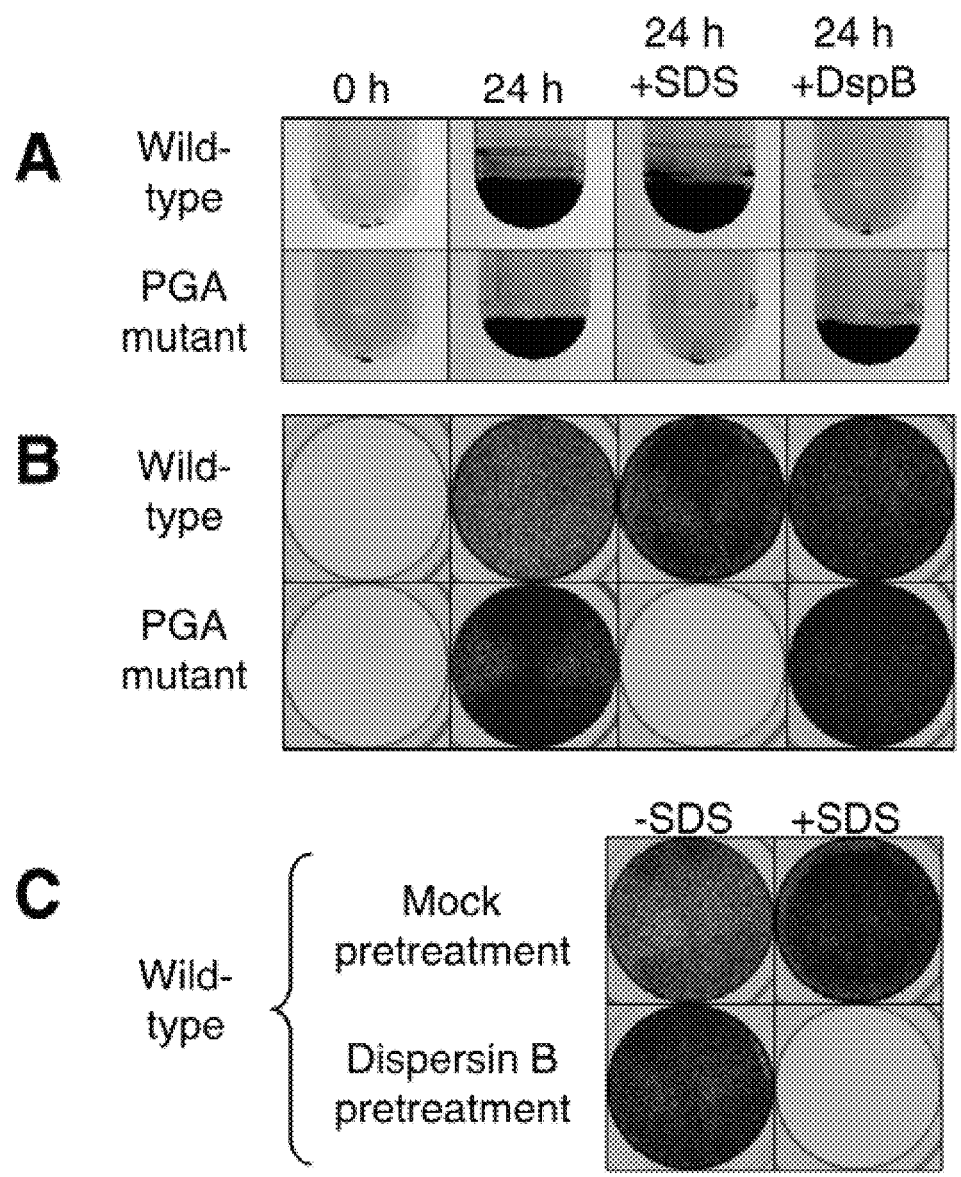
FIG. 28 shows the biofilm growth and detachment of *A. actinomycetemcomitans* strains CU1000 (wild-type) and HW1018 (PGA mutant) in polystyrene tubes and 96-well microtiter plates. All tubes and microplate wells were stained with crystal violet. Biofilm formation at 0 h and 24 h in tubes (panel A) and microplates (panel B). The biofilms on the right were rinsed with water and treated with SDS (0.1% in PBS) or DispersinB™ (20 µg/mL in PBS) for 5 min prior to crystal violet staining. (C) Detachment of CU1000 biofilms from microplates by SDS. Wells on the bottom were pre-treated with DispersinB™ for 30 min prior to the SDS treatment.

Crystal violet dye was used to visualize *A. actinomycetemcomitans* biofilm growth and detachment in polystyrene tubes and 96-well microtiter plates (FIG. 28). Both wild-type and PGA mutant strains formed uniform biofilms that covered the bottom surface of the tube or microplate well after 24 hrs (FIGS. 28A, 28B). In all cultures, the broth remained optically clear and contained <1% of the total CFUs after 24 hrs.

A solution of 0.1% SDS had no effect on the attachment of wild-type biofilms, but caused the rapid detachment of PGA mutant biofilms, in both tubes and microplate wells (FIGS. 30A, 30B). In contrast, a solution of 20 µg/mL of DispersinB™ caused the rapid detachment of wild-type biofilms from tubes, but not from microplate wells. DispersinB™ had no effect on the attachment of PGA mutant biofilms grown in either culture vessel. Microscopic analyses of biofilms grown in tubes indicated that DispersinB™ caused the biofilms to disaggregate into uniformly turbid suspensions containing >99% single cells, with very few small clusters of cells (data not shown). Detachment of biofilms from microplate wells could be achieved if higher DispersinB™ concentrations and longer incubation times were used (Kaplan et al., *J. Bacteriol.* 2003, 185: 4693-4698).

Figure 29:
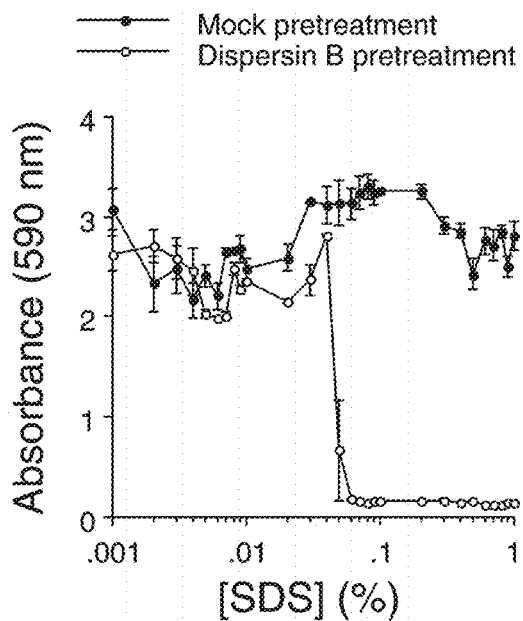
FIG. 29 is line graph showing the detachment of *A. actinomycetemcomitans* strain CU1000 (wild-type) biofilms from 96-well microtiter plates by SDS. Biofilms were pre-treated with PBS (mock pretreatment) or DispersinB™ (20/g/mL in PBS) for 30 min, and then treated with increasing concentrations of SDS for 5 min. Biofilms were then rinsed and stained with crystal violet. We quantitated the amount of hound crystal violet dye, which is proportional to biofilm biomass, by measuring its absorbance at 590 nm. Values are the mean absorbance for duplicate wells. Error bars indicate range of standard deviation.

Pre-treatment of wild-type biofilms with DispersinB™ rendered them sensitive to detachment by SDS in microplate wells (FIG. 28C). Biofilms were treated with 0.001-1% SDS for 5 min and then biofilm biomass was quantitated by measuring the amount of bound crystal violet dye to measure the concentration of SDS needed to detach *A. actinomycetemcomitans* biofilms from microplate wells (FIG. 29). Wild-type biofilms were resistant to detachment at all concentrations of SDS. A slight, but reproducible, increase in crystal violet staining was exhibited by biofilms treated with 0.04-0.11% SDS. In contrast, wild-type biofilms pre-treated with DispersinB™ were resistant to detachment only at SDS concentrations <0.04%. When the concentration of SDS was increased from 0.04 to 0.07%, biofilms underwent a transition from SDS-resistant to SDS-sensitive. This concentration of SDS (1.4-2.4 mM) is very close to the critical micelle concentration (CMC) of SDS in physiologic saline at 37° C. (Helenius et al., *Methods Enzymol.* 1979, 56: 734-749). PGA mutant biofilms exhibited a nearly identical transition from SDS resistant to SDS-sensitive between 0.04 and 0.07% SDS (data not shown).

DispersinB™ Increases the Sensitivity of Biofilms to Killing by SDS

Figure 30:
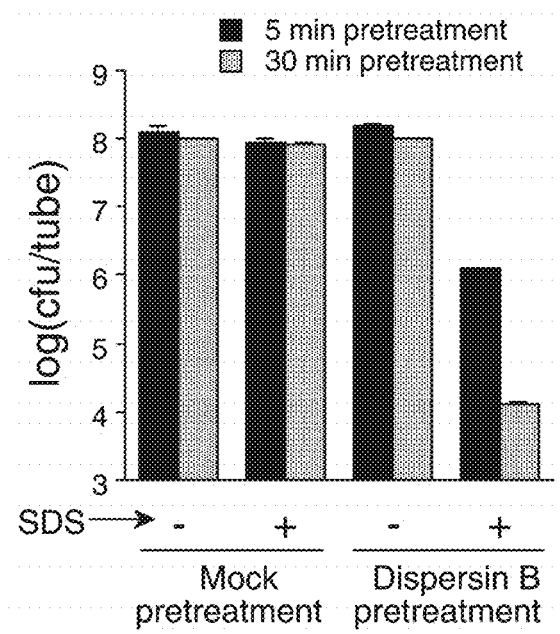
FIG. 30 is bar graph showing that pre-treatment of *A. actinomycetemcomitans* CU1000 (wild-type) biofilms with DispersinB™ increased sensitivity to killing by SDS. Biofilms grown in polystyrene tubes were rinsed with PBS and treated with 1 mL of PBS (mock pre-treatment) or DispersinB™ (20 µg/mL in PBS) for 5 min (black bars) or 30 min (gray bars), and then treated with PBS (−) or SDS (0.01% in PBS; +) for 5 min. Colony forming units (CFU) were enumerated by dilution plating. Values indicate the log 10 of the mean number of CFU per tube for duplicate tubes. Error bars indicate range of standard deviation.

The sensitivity of *A. actinomycetemcomitans* biofilms to killing by 0.01% SDS was tested. The 0.01% SDS corresponds to the MIC against *A. actinomycetemcomitans* planktonic cells (Drake et al., *J. Periodontol.* 1992, 63: 696-700; Wade & Addy, *J. Periodontol.* 1992, 63: 280-282), but which is below the concentration required for biofilm detachment (FIG. 29). Biofilms grown in tubes were pre-treated with PBS (mock pre-treatment) or DispersinB™ for 5 min or 30 min, and then treated with SDS for 5 min. PBS, DispersinB™, or SDS alone did not significantly kill *A. actinomycetemcomitans* biofilms (FIG. 30). However, SDS caused a 2-log-unit decrease in the number of CFU in tubes pre-treated with DispersinB™ for 5 min, and a 4-log-unit decrease in tubes pre-treated for 30 rain.

DispersinB™ Increases the Sensitivity of Biofilms to Killing by CPC

Figure 31:
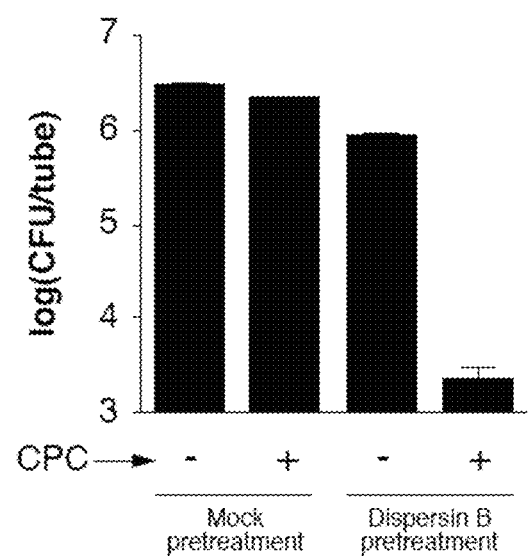
FIG. 31 is bar graph showing that pretreatment of *A. actinomycetemcomitans* CU1000 biofilms with DispersinB™ increases their sensitivity to killing by cetylpyridinium chloride (CPC). Biofilms grown in polystyrene tubes were rinsed with PBS and treated for 30 min with PBS (mock pretreatment) or PBS containing 20 µg/mL of DispersinB™ B, and then treated for 5 min with 0.02% CPC. CFU were enumerated by dilution plating. Values indicate the log 10 of the mean number of CFU/tube for duplicate tubes. Error bars indicate range of standard deviation.

The sensitivity of *A. actinomycetemcomitans* biofilms to killing by 0.02% cetylpyridinium chloride (CPC) was tested. The 0.02% CPC corresponds to 10 times the MIC against *A. actinomycetemcomitans* planktonic cells, but which is below the concentration required for biofilm detachment (data not shown). Biofilms grown in tubes were pretreated for 30 min with phosphate buffer saline (PBS; mock pretreatment) or PBS with 20 µg/mL of DispersinB™, and then treated with 0.02% CPC for 5 min. Biofilms treated with DispersinB™ or CPC alone exhibited little or no reduction in the number of CFU/tube compared to the mock-treated controls (FIG. 31). Biofilms treated with DispersinB™ and then CPC, however, exhibited an approximately 3 log unit decrease in the number of CFUs/tube compared to biofilms treated with DispersinB™ or CPC alone.

These findings suggest that DispersinB™ is a useful agent for sensitizing biofilms to detachment and killing by a detergent such as SDS or CPC, and/or other antimicrobial agents.

Example 27

Formulation of DispersinB™ Antimicrobial Wound Gel

As a general procedure, finely powdered sodium alginate (the use of other alkaline metal alginates may also be considered) was blended with DispersinB™ in distilled water at room temperature for 6-8 hours. As the alginate slowly dissolved and absorbed water, a gel began to form. Stirring continued during this process so that as any yet unblended alginate did not settle out. The final formulation of wound gel contained 0.01% DispersinB™, 1.5% sodium alginate, and 98.49% water.

Example 28

Formulation of Triclosan-DispersinB™ Antimicrobial Wound Gel

The solvent system for triclosan comprising polyethylene glycol, ethanol was prepared in distilled water. Triclosan was dissolved in solvent system at 65° C. with stirring for 8-10 hours. The solution was cooled to room temperature, and DispersinB™ along with sodium alginate was added. The gel was formed as explained in Example 27. The final gel formulation contained 1% triclosan, 10% polyethylene glycol 400, 10% ethanol, 0.01% DispersinB™, 1.5% sodium alginate and 77.49% water.

Example 29

Figure 32:
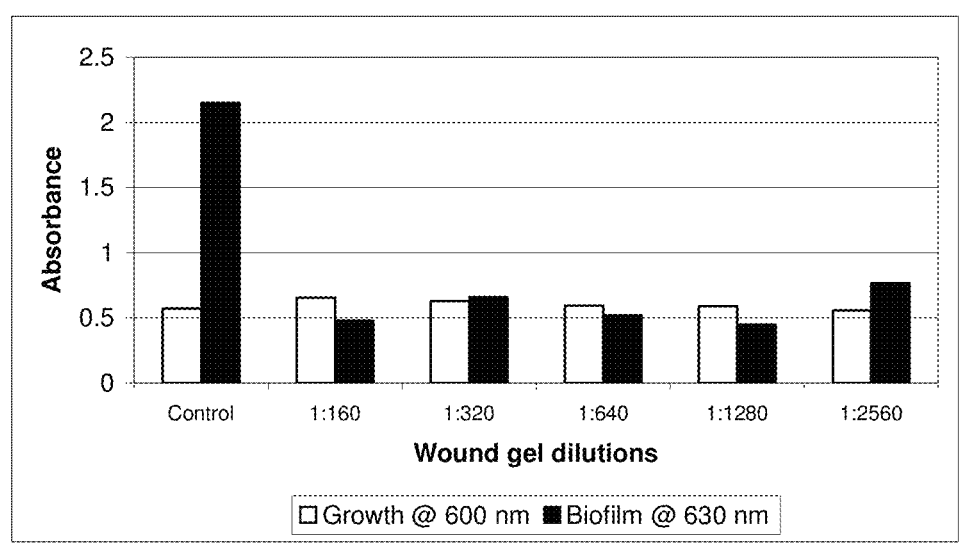
FIG. 32 is bar graph showing the effect of DispersinB™ antimicrobial wound gel on *Staphylococcus epidermidis* growth and biofilm formation.

Effect of DispersinB™ Antimicrobial Wound Gel on *Staphylococcus epidermidis* Biofilm Formation An in vitro microtiter assay was performed to determine the effect of DispersinB™ wound gel on the growth and biofilm formation of *Staphylococcus epidermidis*. *S. epidermidis* biofilm was grown in tryptic soy broth (TSB). *S. epidermidis* was grown in 96-well microtiter plate in the absence and presence of DispersinB™ wound gel at different concentrations. The plate was incubated at 37° C. for 24 hours. Growth of planktonic cells based on the absorbance at 600 nm was determined using Labsystems Multiskan Ascent microplate reader. Biofilm was measured by discarding the medium, rinsing the wells with water (three times), and staining bound cells with crystal violet. The dye was solubilized with 33% acetic acid, and absorbance at 630 nm was determined. For each experiment, background staining was corrected by subtracting the crystal violet bound to uninoculated control (FIG. 32). The test showed 65%-80% biofilm inhibition at all wound gel dilutions tested without affecting planktonic growth.

Example 30

Figure 33:
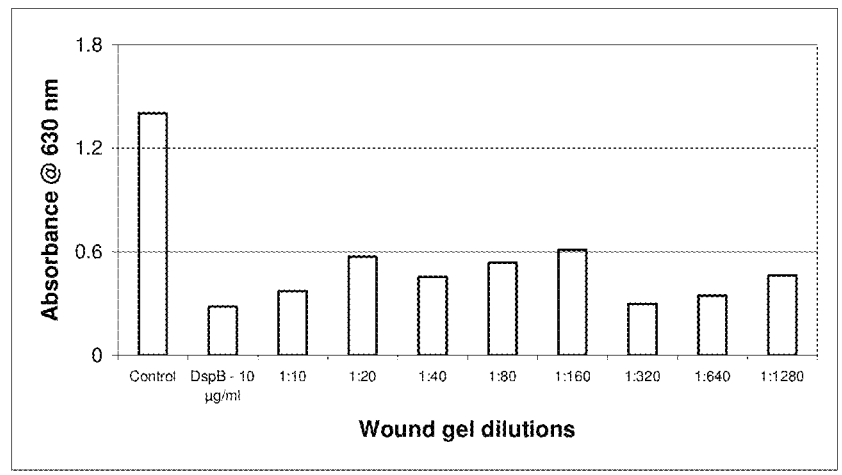
FIG. 33 is a bar graph showing the effect of DispersinB™ antimicrobial wound gel on *Staphylococcus epidermidis* biofilm dispersal.

Effect of DispersinB™ Antimicrobial Wound Gel on *Staphylococcus epidermidis* Biofilm Dispersal An in vitro microtiter assay was performed to determine the effect of DispersinB™ wound gel on the dispersal of *Staphylococcus epidermidis* biofilm. S, epidermidis biofilm was grown in tryptic soy broth (TSB). *S. epidermidis* was grown in 96-well microtiter plate at 37° C. for 24 hours. The planktonic growth was discarded and the biofilm was treated with serial two-fold dilutions of DispersinB™ wound gel at 37° C. for 3 hours. After wound gel treatment the microtiter plate was washed and stained as explained in example 2. The test showed 57%-75% *S. epidermidis* biofilm dispersal at all wound gel dilutions tested (FIG. 33).

Example 31

Antimicrobial Activity of Triclosan-DispersinB™ Antimicrobial Wound Gel Against Wound Associated Pathogens The antimicrobial activity of Triclosan-DispersinB™ was tested in vitro, against wound-associated bacteria such as *Staphylococcus aureus*, *S. epidermidis*, *Enterococcus faecalis*, *Escherichia coli*, *Enterobacter cloacae*, and yeast *Candida albicans* (Vandenbulcke, et al. 2006. *Lower Extremity Wounds*, 5: 109-114). The organisms were incubated on Trypticase Soy Agar and the plates were overlayed with 100 µl of wound gel. The plates were incubated at 37° C. for 24-48 hours. The number of colony forming units (CFU) per milliliter for each culture was calculated (Table 5). Unexpectedly, there was zero growth (no CFU) on any of the TSA plates treated with Triclosan-DispersinB™ wound gel.

TABLE 5

Effect of Triclosan-DispersinB ™ antimicrobial wound gel on growth of wound-associated pathogens

| Pathogen | CFU/ml | |
|---|---|---|
| | Untreated | Treated |
| Gram-positive bacteria | | |
| Staphylococcus aureus | $1.2 \times 10^8$ | 0 |
| S. epidermidis | $1 \times 10^8$ | 0 |
| Enterococcus faecalis | $2.3 \times 10^8$ | 0 |
| Gram-negative bacteria | | |
| Escherichia coli | $2.2 \times 10^8$ | 0 |
| Enterobacter cloacae | $1.5 \times 10^8$ | 0 |
| Yeast | | |
| Candida albicans | $4.5 \times 10^6$ | 0 |

Example 32

Figure 34:
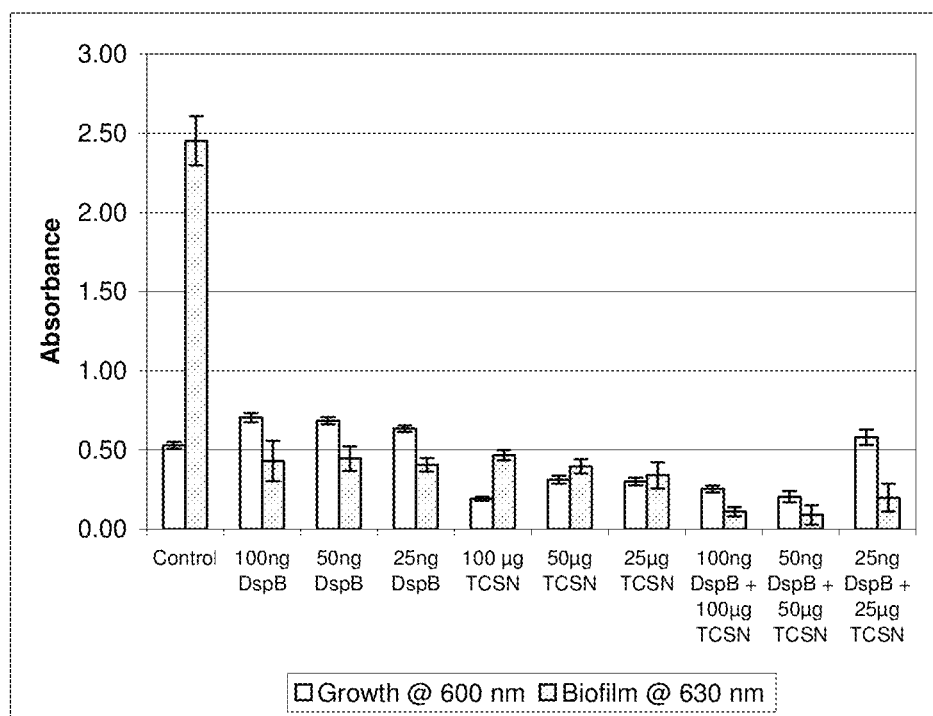
FIG. 34 is a bar graph showing the synergistic inhibitory effect of DispersinB™ and Triclosan (TCSN) combination on *Staphylococcus epidermidis* biofilm formation.

Inhibitory Effect of DispersinB™ and Triclosan (TCSN) Combination on *Staphylococcus epidermidis* Biofilm In vitro microplate assay was performed to determine the synergistic effect of DispersinB™ and triclosan (an antimicrobial agent) on the growth and biofilm formation of *S. epidermidis*. Overnight culture of *S. epidermidis* in Tryptic Soy Broth (TSB) was used as inoculum. Bacteria were grown in TSB on a 96-well microtiterplate in the absence and presence of each compound (DispersinB™ or TCSN) at different concentrations separately and together (DispersinB™+TCSN). The plate was incubated at 37° C. for 24 hours. Growth of planktonic cells based on the absorbance at 600 nm was determined using Labsystems Multiskan Ascent microplate reader. Biofilm was measured by discarding the medium; rinsing the wells with water (three times) and staining bound cells with crystal violet. The dye was solubilized with 33% acetic acid, and absorbance at 630 nm was determined using a microtiter plate reader. For each experiment, background staining was corrected by subtracting the crystal violet bound to uninoculated control. The combination of DispersinB™ and TCSN (50 ng/ml+50 µg/ml, respectively) showed inhibitory effect on *S. epidermidis* biofilm formation (FIG. 34).

Example 33

Figure 35:
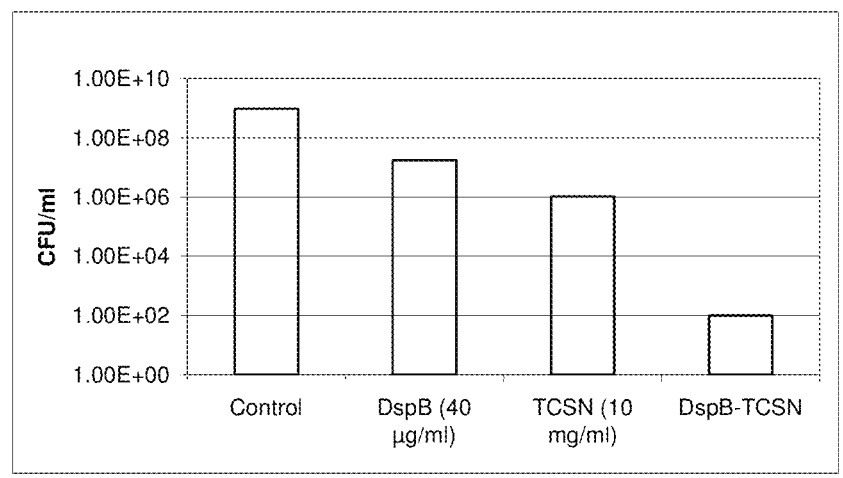
FIG. 35 is a bar graph showing the synergistic inhibitory effect of DispersinB™ and Triclosan (TCSN) combination coated silicone catheters on *Escherichia coli* colonization.
Figure 36:
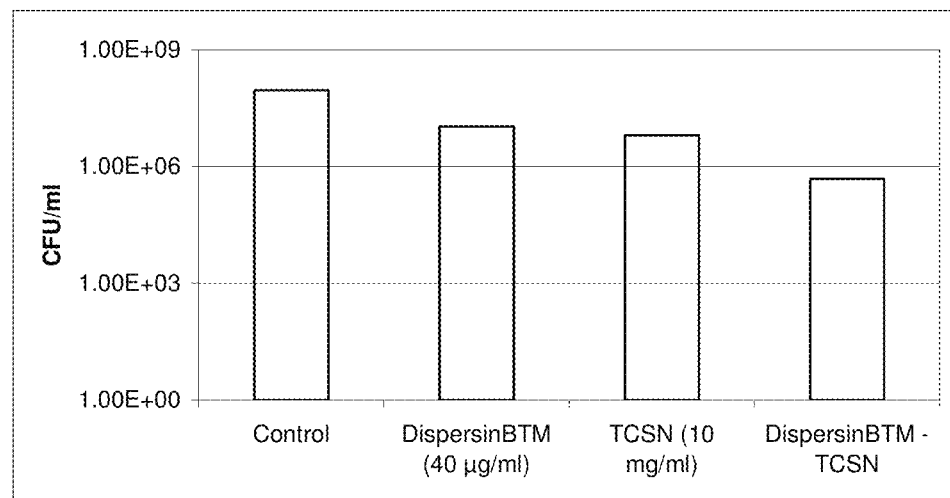
FIG. 36 is a bar graph showing the synergistic inhibitory effect of DispersinB™ and Triclosan (TCSN) combination coated silicone catheters on *Staphylococcus epidermidis* colonization

Inhibitory Effect of DispersinB™ and Triclosan (TCSN) Combination Coated Silicone Catheters on *Staphylococcus epidermidis* and *Escherichia coil* Colonization The adhesion assay was performed to determine the synergistic effect of DispersinB™ and TCSN combination coated silicone catheters on *S. epidermidis* and *E. coli* colonization. The silicone catheter segments (1 cm each) were coated by dipping in DispersinB™ (40 µg/ml) and TCSN (10 mg/ml in 10% Polyethylene glycol) alone and in combination for overnight at 4° C. followed by drying at room temperature. The coated and uncoated segments were incubated in *S. epidermidis* and *E. coli* culture in TSB medium at 37° C. for 24 hours at 100 rpm. After 24 hours of incubation, the sections were washed three times gently. Each washed section was transferred into a sterile tube containing 1 ml sterile saline and subjected to sonication for 30 seconds and followed by 1 minute vortexing. Further, it was serially diluted using sterile saline and plated using Tryptic Soy Agar (TSA) plates. The plates were incubated at 37° C. for 24 hours and the colonies (CFU) were counted. Although triclosan was more effective than DispersinB™ in inhibiting the growth of biofilm-embedded *S. epidermidis* and *E. coli*, the combination-coated catheters showed an enhanced anti-adherence effect on *S. epidermidis* and *E. coli* (FIGS. 35 and 36).

Example 34

Figure 37:
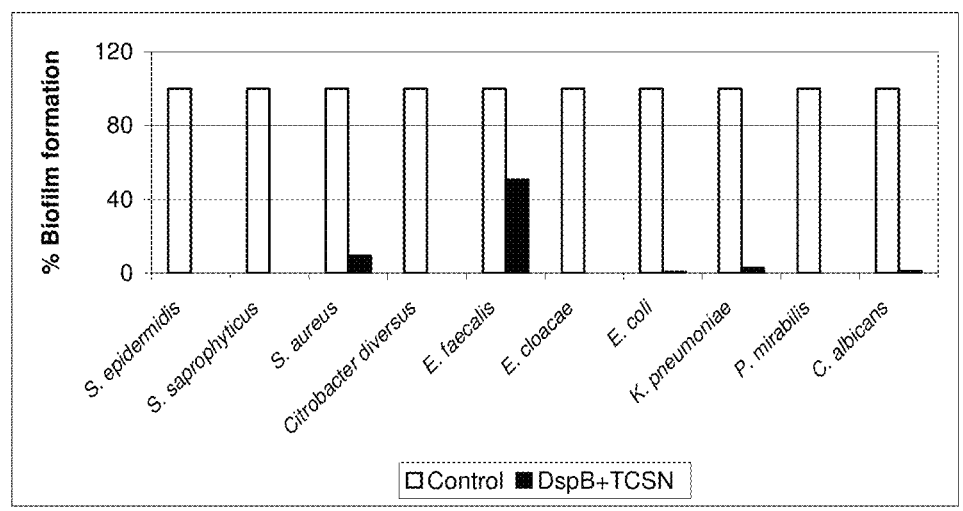
FIG. 37 is a bar graph showing the antibiofilm activity of DispersinB™ and Triclosan (TCSN) combination-coated catheters against catheter-associated microorganisms

Antibiofilm Activity of DispersinB™ and Triclosan (TCSN) Combination-Coated Catheters Against Catheter-Associated Microorganisms The broad-spectrum antibiofilm activity of DispersinB™ and TCSN combination coated catheters against catheter-associated bacteria and yeast was determined. Catheter-associated microorganisms such as *E. coli, Proteus mirabilis, Pseudomonas aeruginosa, Klbesiella pneumoniae, Enterococcus faecalis, Enterococcus cloacae, Citrobacter diversus, S. epidermidis, Staphylococcus aureus, Staphylococcus saprophyticus*, and *Candida albicans* were grown in TSB for 18 hours. The catheter coating and adherence assay for 24 hours were done as described in Example 33. The TCSN-DispersinB™ combination coated catheters were broad-spectrum in terms of inhibiting Gram +ve, Gram –ve bacteria and yeast colonization on catheters (FIG. 37). The combination-coated catheters inhibited >90% colonization of catheters by test organisms, except *Enterococcus faecalis*.

Example 35

Figure 38:
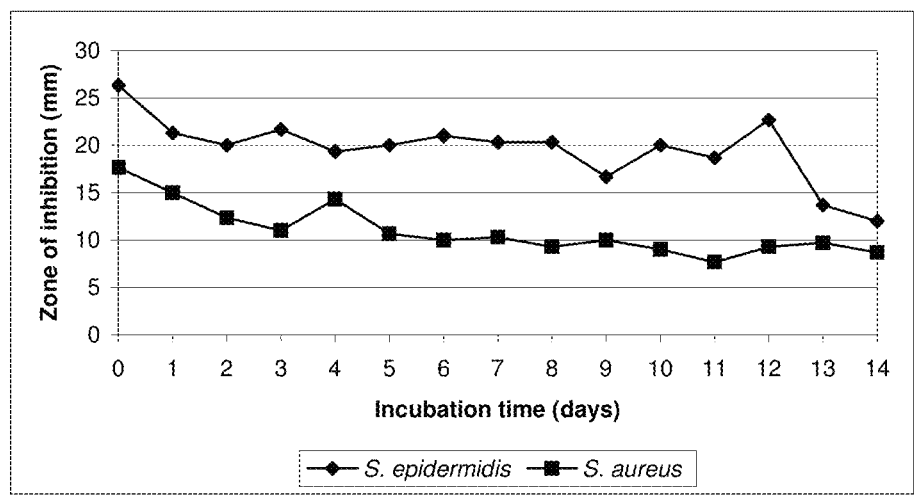
FIG. 38 is a line graph showing the durability of inhibitory activity of DispersinB™ and Triclosan (TCSN) combination-coated polyurethane catheters.

Durability of Inhibitory Activity of DispersinB™ and Triclosan (TCSN) Combination-Coated Polyurethane Catheters The durability of inhibitory activity of DispersinB™+TCSN coated 1 cm polyurethane catheter segments was assessed using Kirby-Bauer technique as previously described by Sheretz et al. (Antimicrob. Agents Chemother., 33: 1174-1178, 1989). The catheters were coated as described in Example 2. The test organisms such as *Staphylococcus aureus* and *Staphylococcus epidermidis* were grown in TSB for 18 hours at 37° C. An appropriate inoculum of each bacterial strain was used to prepare spread plates. The coated catheter segments were carefully plated. Following incubation for 24 hours at 37° C., the zones of inhibition surrounding each segment were measured at the aspects of perpendicular to the long axes. After measuring the zone of inhibition, the segments were transferred onto fresh spread plates inoculated with respective test organism and incubated for 24 hours at 37° C. again. The zones of inhibitions were measured again. This procedure was repeated for determining the durability of inhibitory activity of coated catheter sections against *S. aureus* and *S. epidermidis* (FIG. 38). The coated segments showed significant inhibitory activity against *S. aureus* and *S. epidermidis* even after 14 days of passage.

Example 36

Durability of Inhibitory Activity of DispersinB™ and Triclosan (TCSN) Combination-Coated Polyurethane Catheters in Plasma (Tested Against *Staphylococcus epidermidis*)

Figure 39:
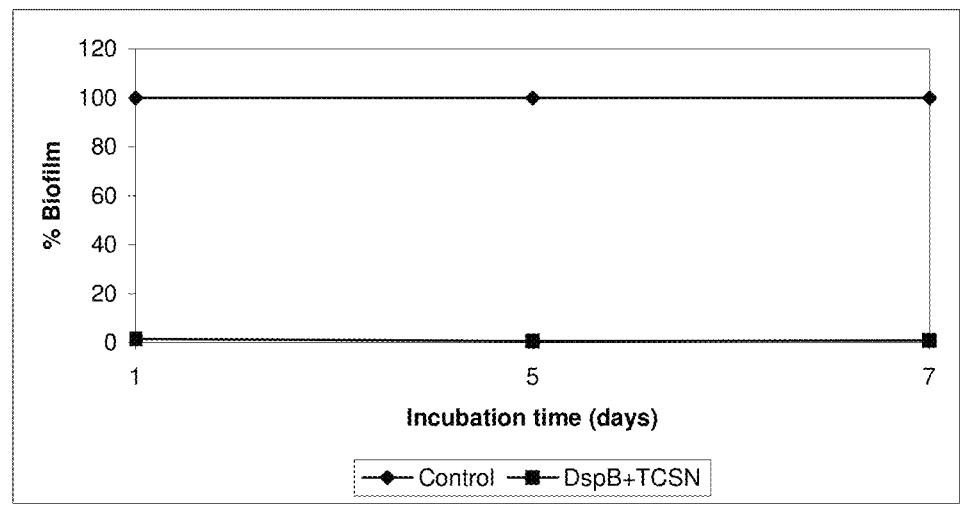
FIG. 39 is a line graph showing the durability of inhibitory activity of DispersinB™ and Triclosan (TCSN) combination-coated polyurethane catheters in plasma (tested against *Staphylococcus epidermidis*).

The ability of DispersinB™-TCSN coated polyurethane catheters to resist bacterial colonization for a period of 7 days was tested by exposing uncoated and coated segments to *S. epidermidis*. The coated and uncoated catheter segments were incubated in rabbit plasma at 37° C. separately for 7 days at 100 rpm prior to challenging with *S. epidermidis*. Both coated and uncoated catheter segments (in triplicate) were removed at time intervals of 1, 5 and 7 days. Further, they were challenged with *S. epidermidis* one at a time. Following the incubation, the catheter segments were rinsed 3 times gently with sterile water. Each washed segment was transferred into sterile tube containing 1 ml sterile saline and subjected to sonication for 30 seconds followed by 1 minute vortexing. Further, it was serially diluted and plated on TSA. The plates were incubated at 37° C. for 24 hours and colony-forming units (CFU) were counted. This procedure was repeated for each time interval. The DispersinB™-TCSN coated catheter segments were effective in preventing *S. epidermidis* biofilm formation over a period of 7 days (FIG. 39).

Example 37

Durability of Inhibitory Activity of DispersinB™ and Triclosan (TCSN) Combination-Coated Polyurethane Catheters in TSB Containing 20% Bovine Serum (Tested Against *Staphylococcus aureus*)

Figure 40:
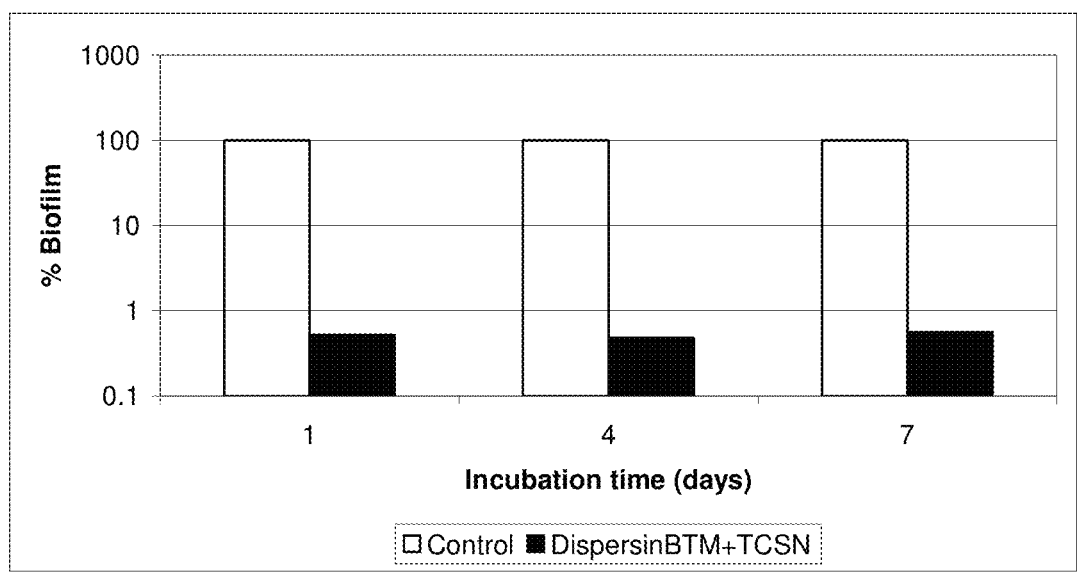
FIG. 40 a bar graph showing the durability of inhibitory activity of DispersinB™ and Triclosan (TCSN) combination-coated polyurethane catheters in TSB containing 20% Bovine Serum (tested against *Staphylococcus aureus*).
Figure 41:
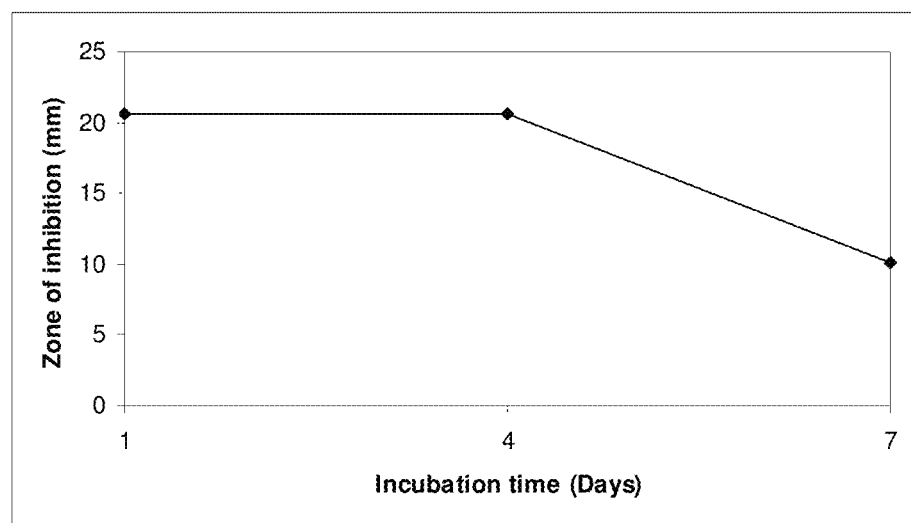
FIG. 41 is a line graph showing the durability of inhibitory activity of DispersinB™ and Triclosan (TCSN) combination-coated polyurethane catheters in TSB containing 20% Bovine Serum (tested against *Staphylococcus aureus*).

The ability of DispersinB™-TCSN coated polyurethane catheters to resist bacterial colonization and retain antimicrobial activity for a period of 7 days was tested by exposing uncoated and coated segments to *S. aureus*. The coated and uncoated segments were incubated in TSB containing 20% bovine serum for 7 days at 100 rpm. The TSB containing 20% bovine serum was replaced every 24 hour. The anti-adherence activity was performed as explained in Example 36. After 7 days of incubation, the coating prevented >99% *S. aureus* biofilm formation (FIG. 40). The antimicrobial activity and durability was assessed using Kirby-Bauer technique as previously described by Sheretz et al. (Antimicrob. Agents Chemother., 33: 1174-1178, 1989). Both coated and uncoated catheter segments (in triplicate) were removed at time intervals of 1, 5 and 7 days. *S. aureus* was grown in TSB for 18 hours at 37° C. An appropriate inoculum of bacterial strain was used to prepare spread plates. The coated catheters were carefully plated. Following incubation for 24 hours at 37° C., the zones of inhibition surrounding each segment were measured at the aspects of perpendicular to the long axes. This procedure was repeated for each time interval (FIG. 41). The coated catheter segments retained antimicrobial activity even after 7 days of incubation in TSB containing 20% bovine serum.

Example 38

Durability of Inhibitory Activity of DispersinB™ and Triclosan (TCSN) Combination-Coated Silicone Catheters in Synthetic Urine (Tested Against *Staphylococcus epidermidis*)

Figure 42:
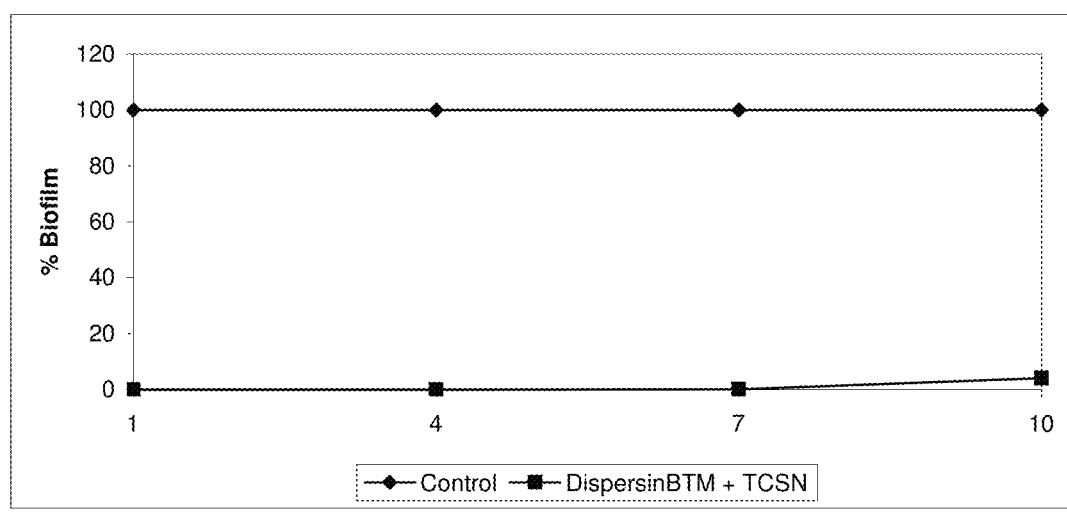
FIG. 42 is a line graph showing the inhibitory activity of DispersinB™ and Triclosan (TCSN) combination coated silicone catheters in synthetic urine (tested against *Staphylococcus aureus*).
Figure 43:
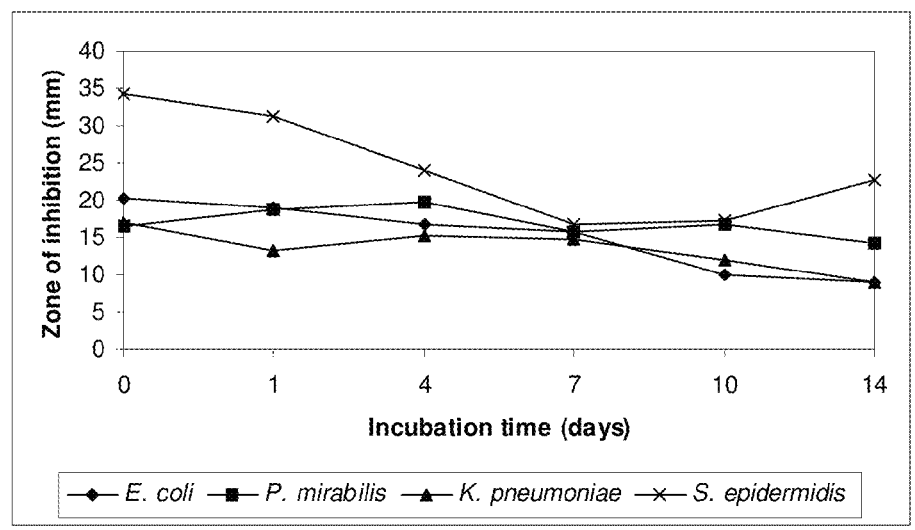
FIG. 43 is a line graph showing the durability of DispersinB™ and Triclosan (TCSN) combination coated silicone catheters in synthetic urine.

The ability of DispersinB™-TCSN coating on silicone catheters to resist bacterial colonization and retain antimicrobial activity for 10 days was tested by exposing the uncoated and coated segments to test organisms. The coated and uncoated catheter segments were incubated in sterile artificial urine medium at 37° C. for 10-14 days at 100 rpm. The artificial urine in the flask was replaced with fresh artificial urine every 24 hours. Both coated and uncoated catheter segments (in triplicate) were removed at time intervals of 1, 4, 7, 10 and 14 days. Further, they were challenged with *S. epidermidis* one at a time. Following the incubation, the catheter sections were rinsed 3 times gently with sterile water. Each washed segment was transferred into sterile tube containing 1 ml sterile saline and subjected to sonication for 30 seconds followed by 1 minute vortexing. Further, each section was serially diluted and plated on TSA. The plates were incubated at 37° C. for 24 hours and colony-forming units (CFU) were counted. This procedure was repeated for each time interval. The DispersinB™-TCSN coated catheter segments were effective in preventing *S. epidermidis* biofilm formation for more than 10 days (FIG. 42). The antimicrobial activity retained by the catheters was studied by Kirby-Bauer technique as previously described by Sheretz et al. (Antimicrob. Agents Chemother., 33: 1174-1178, 1989) against *E. coli, P. mirabilis, K. pneumoniae* and *S. epidermidis*. The coated catheter segments showed a significant inhibitory activity against *E. coli, P. mirabilis, K pneumoniae* and *S. epidermidis* even after 14 days (FIG. 43).

Example 39

In Vivo Efficacy of DispersinB™+Triclosan (DispersinB™+TCSN) Coated Central Venous Catheters (CVC)

Figure 44:
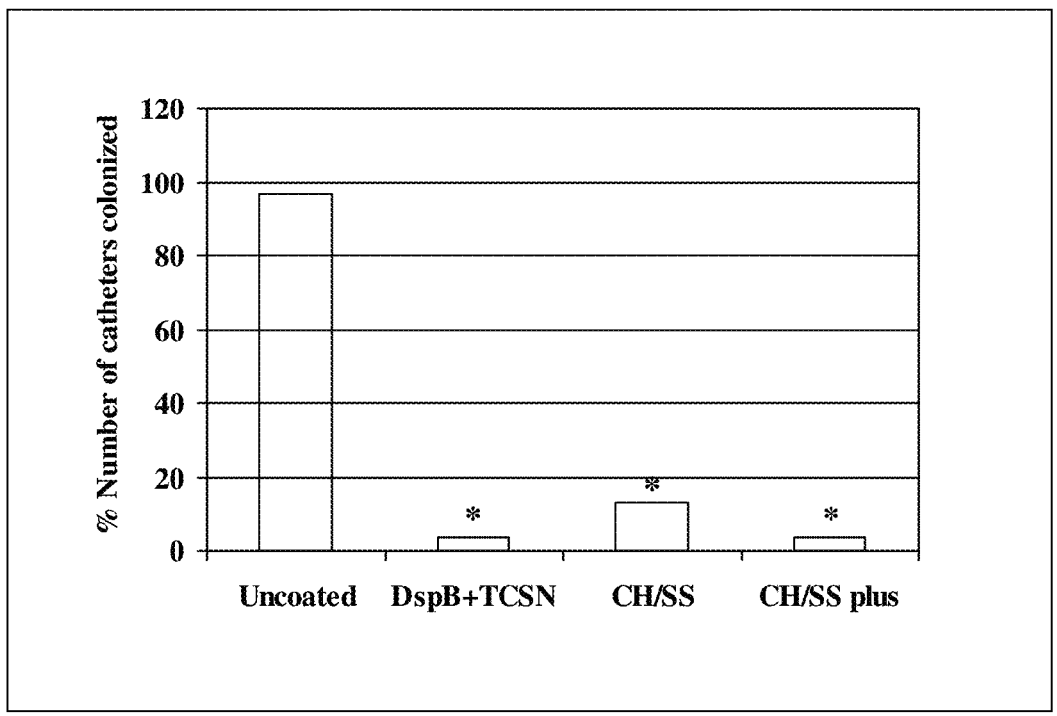
FIG. 44 is a bar graph showing the in vivo efficacy of DispersinB™ and Triclosan (TCSN) combination coated central venous catheters.

In vivo efficacy study was conducted using rabbits to determine the rates of catheter colonization and catheter related infections by *Staphylococcus aureus* with the following four groups of CVCs: (i) catheters coated with DispersinB™+TCSN, (ii) catheters coated with chlorhexidine+silver sulfadiazine (CH/SS), (iii) chlorhexidine+silver sulfadiazine plus (CH/SS plus), and (iv) uncoated catheters. Thirty 1-cm segments of CVCs from each group were implanted subcutaneously in the back of a total of 20 female New-Zealand white, specific pathogen-free rabbits. Each catheter insertion site was inoculated with $10^4$ colony forming units (CFU) of clinical isolate of S aureus. After 7 days, the rabbits were sacrificed; the catheters were explanted, and cultured by plating on agar plates. Out of 30, 29 (96.7%) uncoated, 1 (3.3%) DispersinB™+TCSN coated, 4 (13.3%) CH/SS coated and 1 (3.3%) CH/SS plus coated catheters were colonized by *S. aureus* (FIG. 44). The DispersinB™+TCSN, CH/SS and CH/SS plus catheter coatings significantly reduced catheter colonization by *S. aureus* ($p<0.001$) compared to uncoated catheter.

Example 40

Figure 45:
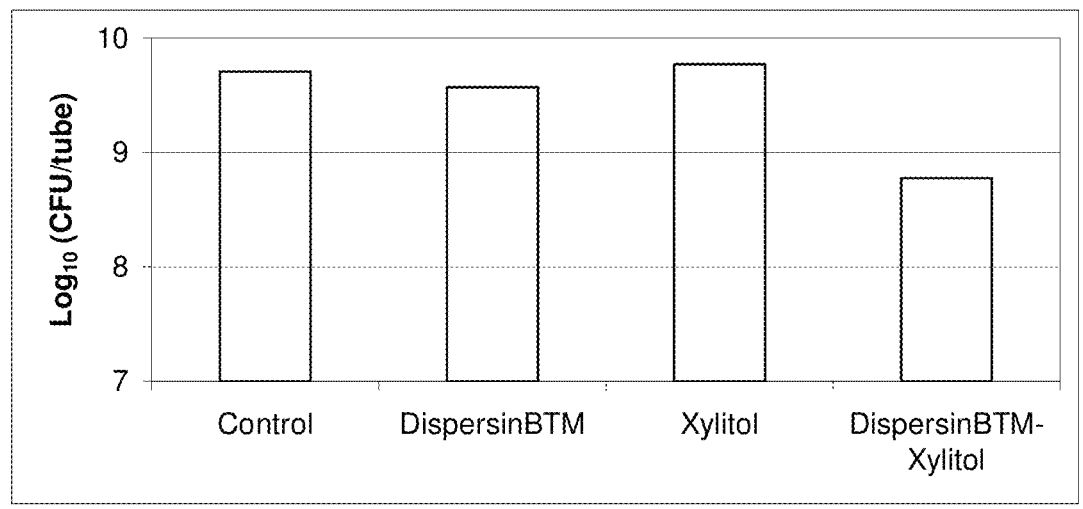
FIG. 45 is a bar graph showing the effect of DispersinB™ and xylitol alone and in combination on *Staphylococcus epidermidis* biofilm formation.

Enhancing Effect of DispersinB on the Sensitivity of Biofilm-Embedded *Staphylococcus epidermidis* to Xylitol An in vitro biofilm-dispersal assay was performed to determine the enhancing effect of DispersinB™ on the sensitivity of biofilm-embedded *S. epidermidis* to xylitol. *S. epidermidis* biofilm was grown in 1.5 ml polypropylene microcentrifuge tubes (2001 culture volume) for 24 h and medium containing planktonic cells was discarded. Further, each tube was rinsed with 200 μl of fresh medium and then treated with 200 μl medium containing 5% xylitol alone or in combination with DispersinB (20 μg/m)). After 3 b incubation at 37° C., 10 μl of 200 μg/ml DispersinB was added to each tube, and tubes were incubated for additional min to detach biofilm. Serial dilutions of the cells were plated on tryptic soy agar. The DispersinB slightly enhanced the inhibitory effect of xylitol on biofilm-embedded *S. epidermidis* (FIG. 45).

Example 41

Figure 46:
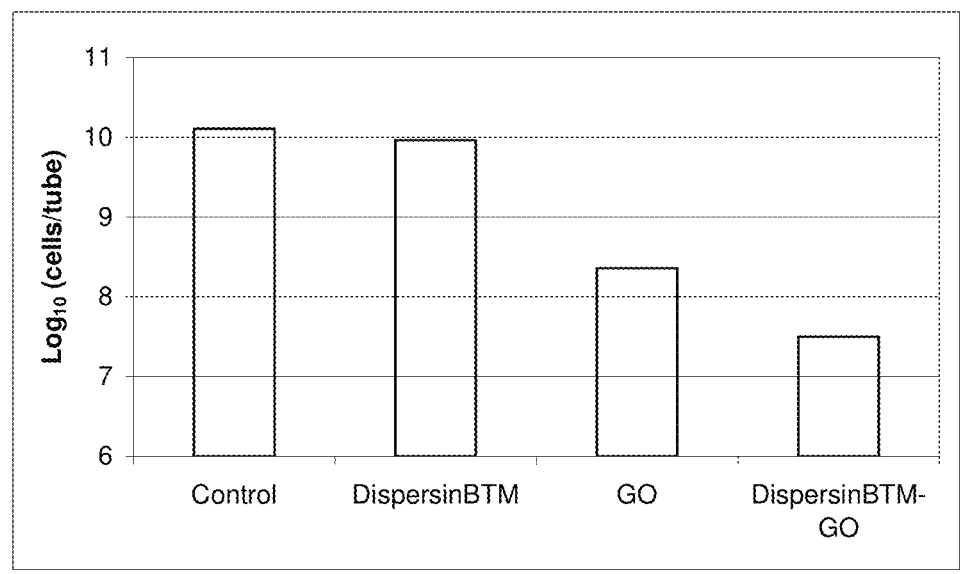
FIG. 46 is a bar graph showing the effect of DispersinB™ and glucose oxidase alone and in combination on *Staphylococcus epidermidis* biofilm formation.

Enhancing Effect of DispersinB™ on the Sensitivity of Biofilm-Embedded *Staphylococcus epidermidis* to Antimicrobial Enzyme Glucose Oxidase An in vitro biofilm-dispersal assay was performed to determine the enhancing effect of DispersinB™ on the sensitivity of biofilm-embedded *S. epidermidis* to glucose oxidase. *S. epidermidis* biofilm was grown in 1.5 ml polypropylene microcentrifuge tubes (200 μl culture volume), medium containing planktonic cells was discarded. Further, each tube was rinsed with 200 μl of fresh medium and then treated with 200 μl medium containing 10 U/m of glucose oxidase alone or in combination with 20 μg/ml of DispersinB. After 3 h incubation at 37° C., 10 μl of 200 μg/ml DispersinB™ was added to each tube, and tubes were incubated for additional 5 min to detach biofilm. Serial dilutions of the cells were plated on tryptic soy agar. DispersinB enhanced the inhibitory effect of glucose oxidase on biofilm-embedded *S. epidermidis* (FIG. 46).

Example 42

Figure 47:
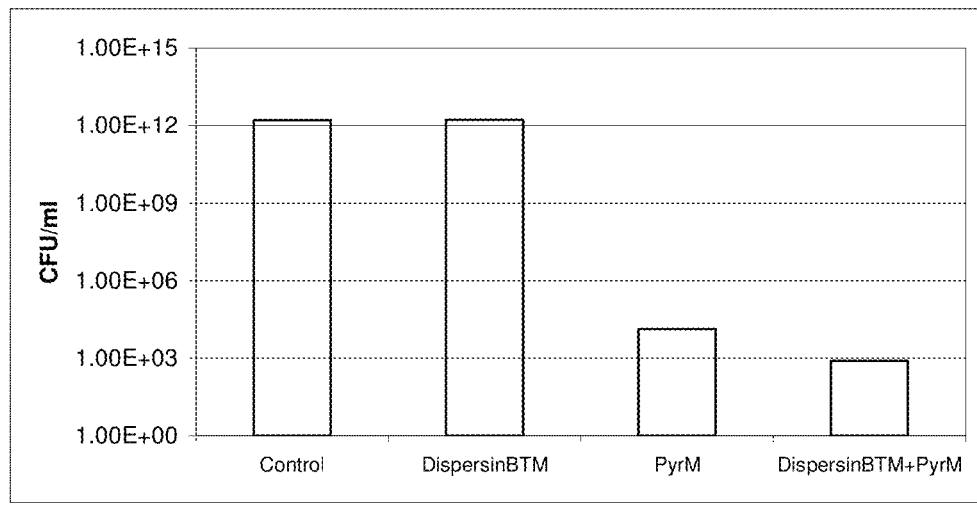
FIG. 47 is a bar graph showing the effect of DispersinB™ and N-(1-pyrenyl)maleimide (PyrM) alone and in combination on *Staphylococcus epidermidis* biofilm formation.

Effect of DispersinB™ and N-(1-pyrenyl)maleimide (PyrM) Alone and in Combination on *Staphylococcus epidermidis* Biofilm Formation In vitro microplate assays were performed to determine the effect of DispersinB and PyrM combination on the growth of biofilm-embedded *S. epidermidis*. Overnight growth of *S. epidermidis* in tryptic soy broth (TSB) was used as inoculum. Biofilm was developed in 12-well microplate in the absence and presence of each test compound (1 μg/ml DispersinB or 8 μg/ml PyrM) separately and together (DispersinB+PyrM). The plates were incubated at 37° C. for 24 h. Medium containing planktonic cells in each well was removed gently and rinsed with sterile water. A known volume of water was added to each well and sonicated for seconds. The contents of each well was transferred into a sterile tube, vortexed for a minute, followed by 10-fold serial dilution, and plated on agar plates using a spreader. After incubating the plates at 37° C. for 24 h, colony-forming units (CFU) were counted. Although PyrM was more effective than DispersinB in inhibiting the growth of biofilm-embedded S epidermidis, the combination of DispersinB and PyrM had an enhancing inhibitory effect on biofilm-embedded *S. epidermidis* (FIG. 47).

Example 43

Effect of DispersinB™ and N,N-(1,2 phenylene)dimaleimide (oPDM) on Biofilm Formation of *Staphylococcus epidermidis*

Figure 48:
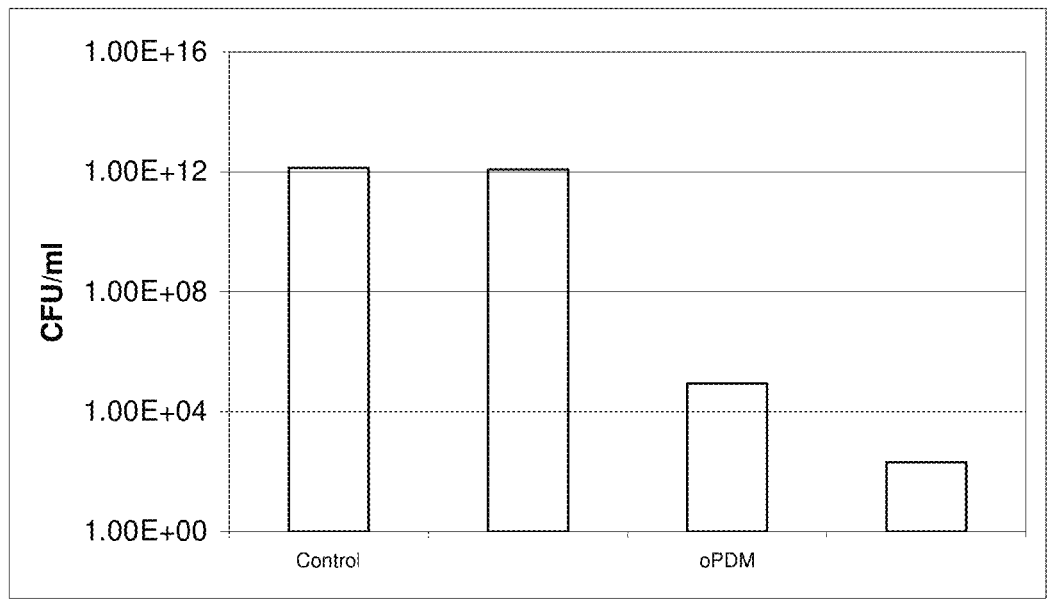
FIG. 48 is a bar graph showing the effect of DispersinB™ and N,N-(1,2 phenylene)dimaleimide (oPDM), alone and in combination on *Staphylococcus epidermidis* biofilm formation.

In vitro microplate assays were performed to determine the effect of DispersinB™ and oPDM combination on the growth of biofilm embedded *S. epidermidis*. Overnight growth of *S. epidermidis* in tryptic soy broth (TSB) was used as inoculum. Biofilm was developed in 12-well microplate in the absence and presence of each test compound (1 μg/ml DispersinB or 625 μg/ml oPDM) separately and together (DispersinB+oPDM). The plates were incubated at 37° C. for 24 hours. Medium containing planktonic cells in each well was removed gently and rinsed with sterile water. A known volume of water was added to each well and sonicated for 30 seconds. The contents of each well was transferred into a sterile tube, vortexed for a minute, followed by 10-fold serial dilution, and plated on agar plates using a spreader. After incubating the plates at 37° C. for 24 h, colony-forming units (CFU) were counted. Although oPDM was more effective than DispersinB in inhibiting the growth of biofilm-embedded *S. epidermidis*, DispersinB and oPDM together had an enhancing inhibitory effect on biofilm-embedded *S. epidermidis* (FIG. 48).

Example 44

Antimicrobial Activity of Catheter Coated with DispersinB™ and an Antimicrobial

Catheter segments (1 cm) were coated with the solution containing DispersinB™ and antimicrobial by dipping and drying three times. Catheter segments could also be coated sequentially with an antimicrobial agent and DispersinB™. Antimicrobial agents such as benzalkonium chloride, sodium usnate, 5-fluorouracil, cefamandole nafate and chitosan were used separately in combination with DispersinB™ for coating. The solution containing DispersinB and each antimicrobial was prepared in 10% glycerol as a binding agent. Glycerol could be substituted with polyethylene glycol.

The antimicrobial activity of coated catheter was determined using Kirby-Bauer technique as previously described by Sheretz, et al. (Antimicrob. Agents Chemother., 33:1174-1178, 1989). Catheter-associated microorganisms such as *Escherichia coli, Pseudomonas aeruginosa, Staphylococcus epidermidis, S. aureus* and *Candida albicans* were grown in tryptic soy broth for 18 h at 37° C. An appropriate inoculum of each strain was used to prepare spread plates. The coated and uncoated sections were then carefully pressed onto the center of each spread plate. Following the incubation for 24 h at 37° C., the zone of inhibition surrounding each section was measured at the aspects of perpendicular to the long axes. The catheters coated with DispersinB™-cefamandole nafate and DispersinB™-benzalkonium chloride showed antimicrobial activity against *E. coli, S. epidermidis* and *S. aureus* (Table 6). The catheters coated with DispersinB™-5-fluorouracil showed antimicrobial activity against all the test organisms except *C. albicans*. However, the catheters coated with DispersinB-sodium usnate were selectively active against gram-positive organisms.

Example 45

Figure 49:
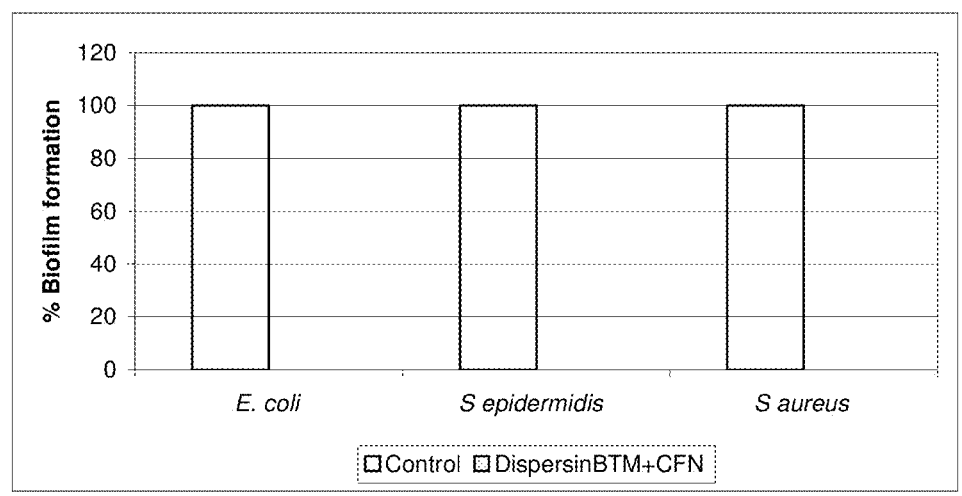
FIG. 49 is a bar graph showing the antibiofilm activity of DispersinB™ and cefamandole nafate (CFN) combination-coated catheters.

Antibiofilm Activity of DispersinB™ and Cefamandole Nafate (CFN) Combination-Coated Catheters Against Catheter-Associated Microorganisms The antibiofilm activity of DispersinB™ and cefamandole nafate (CFN) combination coated catheters against catheter-associated bacteria and yeast was determined. Catheters were coated with DispersinB™ (100 μg/ml)-cefamandole nafate (50 mg/ml). Catheter-associated microorganisms such as *Escherichia coli, Staphylococcus epidermidis* and *S. aureus* were grown in TSB for 18 h. The coated and uncoated catheter segments were placed in 15 ml tubes separately containing 10 ml TSB inoculated with test organism. The tubes were incubated in a water bath at 37° C. with gentle shaking. After 24 h incubation, catheter segments were washed, sonicated, vortexed and the serial dilutions were plated on tryptic soy agar. The DispersinB™-CFN combination coated catheters inhibited >99% *E. coli, S. epidermidis* and *S. aureus* biofilm formation (FIG. 49).

Example 46

Figure 50:
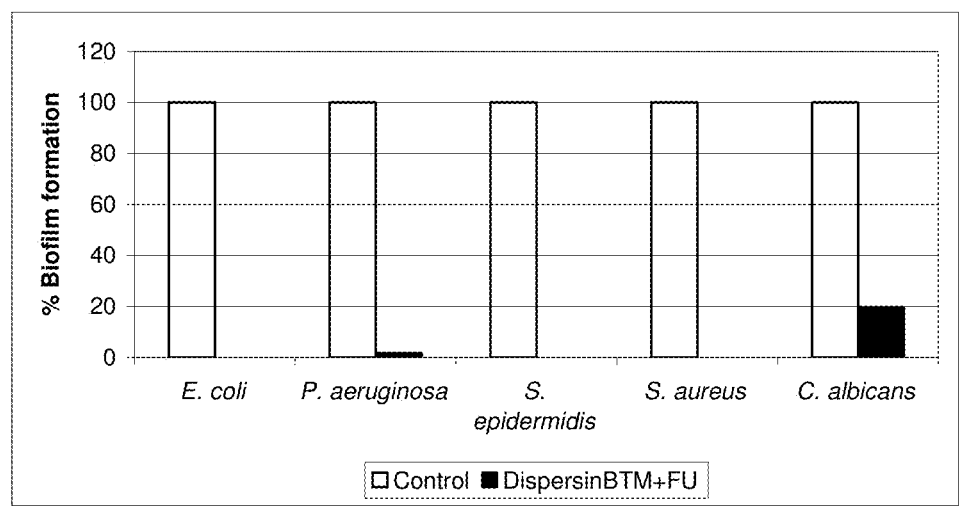
FIG. 50 is a bar graph showing the antibiofilm activity of DispersinB™ and 5-fluorouracil (FU) combination-coated catheters.

Antibiofilm Activity of DispersinB™ and 5-fluorouracil (FU) Combination-Coated Catheters Against Catheter-Associated Microorganisms The antibiofilm activity of DispersinB™ and 5-fluorouracil (FU) combination coated catheters against catheter-associated bacteria and yeast was determined. Catheters were coated with DispersinB™ (100 μg/ml)-FU (10 mg/ml). Catheter-associated microorganisms such as *Escherichia coli, Pseudomonas aeruginosa, Staphylococcus epidermidis, S. aureus* and *Candida albicans* were grown in TSB for 18 h. The coated and uncoated catheter segments were placed in 15 ml tubes separately containing 10 ml TSB inoculated with test organism. The tubes were incubated in a water bath at 37° C. with gentle shaking. After 24 h incubation, catheter segments were washed, sonicated, vortexed and the serial dilutions were plated on tryptic soy agar. The DispersinB™-FU combination coated catheters inhibited >99% gram negative and gram-positive bacterial biofilm formation (FIG. 50), and it inhibited 80% *C. albicans* biofilm.

TABLE 6

Antimicrobial activity of catheters coated with DispersinB ™ (100 μg/ml) and antimicrobial agents

| Coating | Con. of antimicrobial agent in the coating solution | Zone of inhibition (mm) against test organisms | | | | |
|---|---|---|---|---|---|---|
| | | E. coli | P. aeruginosa | S. epidermidis | S. aureus | C. albicans |
| DispersinB ™-Cefamandole nafate | 50 mg/ml | 27.5 | 0 | 44 | 24 | 0 |
| DispersinB ™-5-fluorouracil | 10 mg/ml | 30.5 | 15.5 | 42 | 27.5 | 0 |
| DispersinB ™-sodium usnate | 10 mg/ml | 0 | 0 | 23 | 13.5 | 0 |
| DispersinB ™-benzalkonium chloride | 100 mg/ml | 3.5 | 0 | 23.5 | 19 | 10.0 |

Example 47

Figure 51:
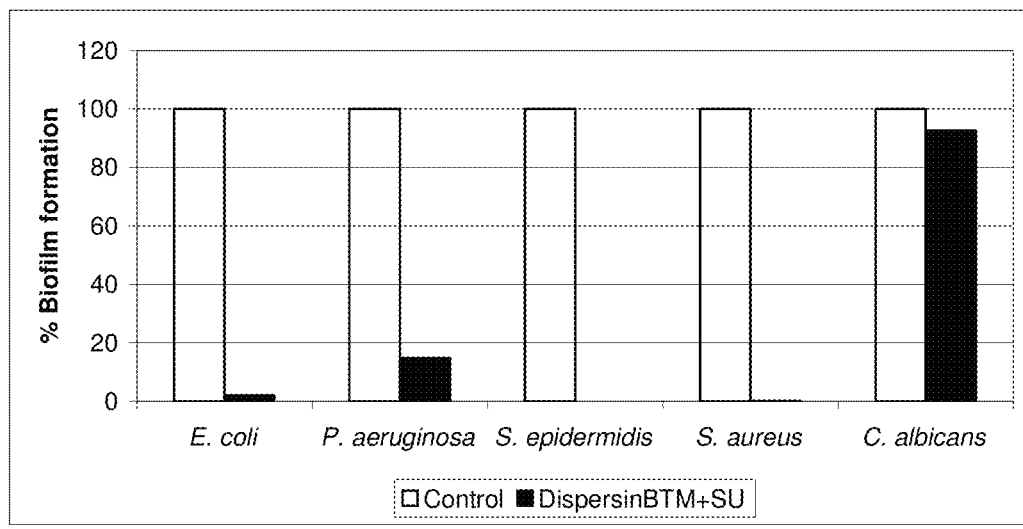
FIG. 51 is a bar graph showing the antibiofilm activity of DispersinB™ and sodium usnate (SU) combination-coated catheters.

Antibiofilm Activity of DispersinB™ and Sodium Usnate (SU) Combination-Coated Catheters Against Catheter-Associated Microorganisms The antibiofilm activity of DispersinB™ and sodium usnate (SU) combination coated catheters against catheter-associated bacteria and yeast was determined. Catheters were coated with DispersinB™ (100 µg/ml)-SU (10 mg/ml). Catheter associated microorganisms such as *Escherichia coli, Pseudomonas aeruginosa, Staphylococcus epidermidis, S. aureus* and *Candida albicans* were grown in TSB for 18 h. The coated and uncoated catheter segments were placed in 15 ml tubes separately containing 10 ml TSB inoculated with test organism. The tubes were incubated in a water bath at 37° C. with gentle shaking. After 24 h incubation, catheter segments were washed, sonicated, vortexed and the serial dilutions were plated on tryptic soy agar. The DispersinB™-SU combination coated catheters were more effective in inhibiting biofilm formation in gram-positive bacteria compared to that in gram-negative bacteria (FIG. 51).

Example 48

Figure 52:
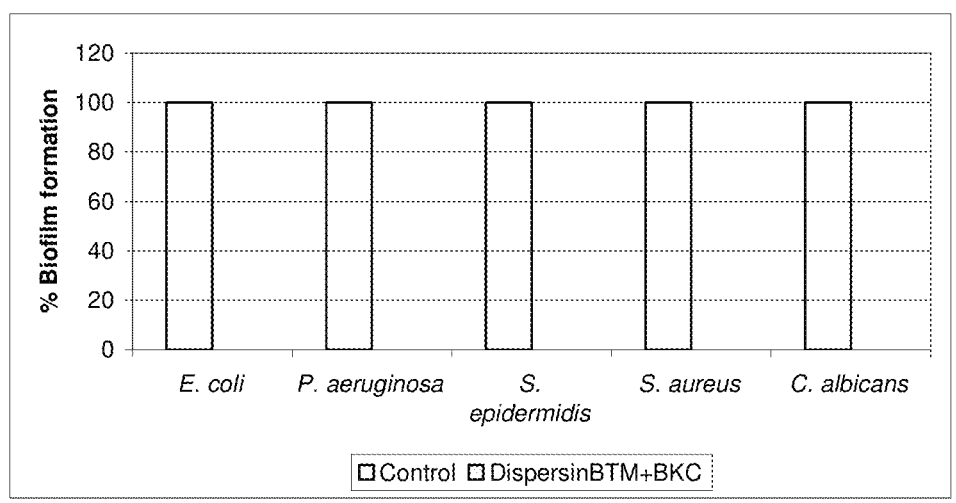
FIG. 52 is a bar graph showing the antibiofilm activity of DispersinB™ and benzalkonium chloride (BKC) combination-coated catheters.

Antibiofilm Activity of DispersinB™ and Benzalkonium Chloride (BKC) Combination-Coated Catheters Against Catheter-Associated Microorganisms The antibiofilm activity of DispersinB™ and benzalkonium chloride (BKC) combination coated catheters against catheter-associated bacteria and yeast was determined. Catheters were coated with DispersinB™ (100 µg/ml)-BKC (100 mg/ml). Catheter-associated microorganisms such as *Escherichia coli, Pseudomonas aeruginosa, Staphylococcus epidermidis, S. aureus* and *Candida albicans* were grown in TSB for 18 h. The coated and uncoated catheter segments were placed in 15 ml tubes separately containing 10 ml TSB inoculated with test organism. The tubes were incubated in a water bath at 37° C. with gentle shaking. After 24 h incubation catheter segments were washed, sonicated, vortexed and the serial dilutions were plated on tryptic soy agar. The DispersinB™-BKC combination coated catheters completely inhibited biofilm formation in gram-negative as well as gram-positive bacteria and also in yeast (FIG. 52).

Example 49

Figure 53:
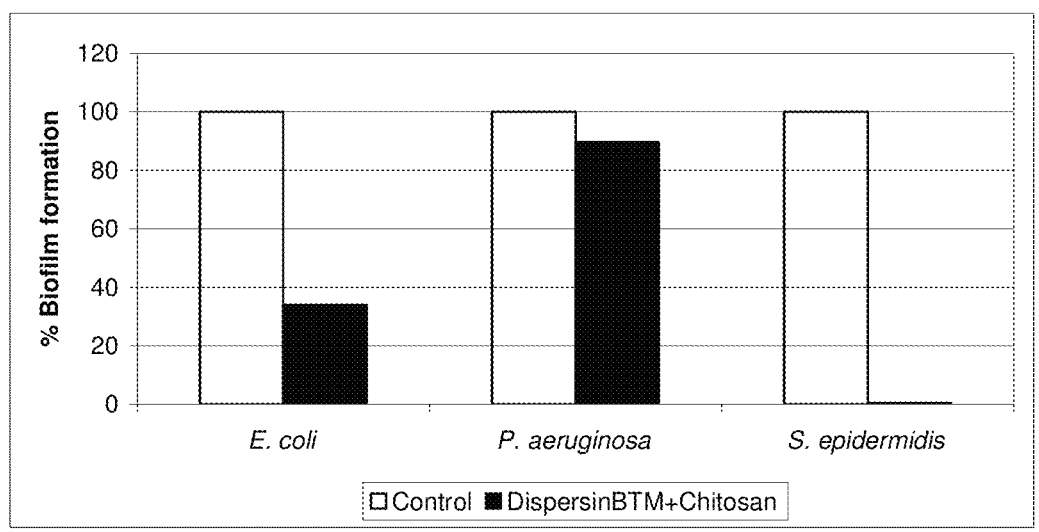
FIG. 53 is a bar graph showing the antibiofilm activity of DispersinB™ and chitosan combination-coated catheters.

Antibiofilm Activity of DispersinB™ and Chitosan Combination-Coated Catheters Against Catheter-Associated Microorganisms The antibiofilm activity of DispersinB™ and chitosan combination coated catheters against catheter-associated bacteria was determined. Catheters were coated with DispersinB™ (100 µg/ml)-chitosan (5 mg/ml). Catheter-associated microorganisms such as *Escherichia coli, Pseudomonas aeruginosa,* and *Staphylococcus epidermidis* were grown in TSB for 18 h. The coated and uncoated catheter segments were placed in 15 ml tubes separately containing 10 ml TSB inoculated with test organism. The tubes were incubated in a water bath at 37° C. with gentle shaking. After 24 h incubation, catheter segments were washed, sonicated, vortexed and the serial dilutions were plated on tryptic soy agar. The DispersinB™-chitosan combination coated catheters inhibited 67% *E. coli*, and >99% *S. epidermidis* biofilms (FIG. 53).

The invention claimed is:

1. A composition for inhibiting biofilm-embedded microorganisms comprising: (a) amino acids 21-381 of SEQ ID NO:2, an active fragment or variant having at least 95% sequence identity thereof that disperses a biofilm; and (b) an antimicrobial agent.

2. The composition of claim 1, wherein is in a concentration of about 1 μg/ml to about 500 μg/ml of the composition.

3. The composition of claim 1, wherein the antimicrobial agent comprises triclosan, rifampicin, cefamandole nafate, nitrofurazone, bismuth thiol, bismuth ethanedithiol (BisEDT), ciprofloxacin, ovotransferrin, lactoferrin, sodium usnate, 5-fluorouracil, sodium dodecyl sulfate (SDS), chlorhexidine, benzalkonium chloride, EDTA, silver nanopowder, silver compounds, glucose oxidase, lactose peroxidase, cadexomer iodine, methylene blue, gentian violet, medium-chain dextrans, sugar alcohol, or mixtures thereof.

4. The composition of claim 3, wherein the antimicrobial agent is triclosan.

5. The composition of claim 4, wherein the triclosan is in a concentration of about 0.1 to about 100 mg/ml.

6. The composition of claim 3, wherein the antimicrobial agent is nitrofurazone.

7. The composition of claim 3, wherein the antimicrobial agent is 5-fluorouracil.

8. The composition of claim 3, wherein the antimicrobial agent is EDTA.

9. The composition of claim 3, wherein the antimicrobial agent is silver nanopowder.

10. The composition of claim 1 further comprising (c) a viscosity increasing agent.

11. The composition of claim 10, wherein said amino acids 21-381 of SEQ ID NO:2, active fragment or variant having at least 95% sequence identity thereof, is about 0.001% to 0.1% by weight.

12. The composition of claim 10, wherein the antimicrobial agent is selected from the group consisting of triclosan, rifampicin, cefamandole nafate, nitrofurazone, bismuth thiol, bismuth ethanedithiol (BisEDT), ciprofloxacin, ovotransferrin, lactoferrin, sodium usnate, 5-fluorouracil, sodium dodecyl sulfate (SDS), chlorhexidine, ber.kappa.alkonium chloride, HDTA, silver nanopowder, silver compounds, glucose oxidase, lactose peroxidase, cadexomer iodine, methylene blue, gentian violet, medium-chain dextrans, sugar alcohol, and mixtures thereof.

13. The composition of claim 12, wherein the antimicrobial agent is triclosan.

14. The composition of claim 13, wherein the triclosan is about 0.1% to about 10% by weight.

15. The composition of claim 10, further comprising polyethylene glycol (PEG).

16. The composition of claim 1, wherein the composition is in the form of a formable or pliable putty or flexible sheets that can be readily molded and cut into shape.

17. A wound dressing or covering comprising the composition of claim 1.

18. A method of inhibiting biofilm-embedded microorganisms comprising administering an effective amount of the composition of claim 1.

19. The method of claim 18, wherein the antimicrobial agent comprises triclosan, rifampicin, cefamandole nafate, nitrofurazone, bismuth thiol, bismuth ethanedithiol (BisEDT), ciprofloxacin, ovotransferrin, lactoferrin, sodium usnate, 5-fluorouracil, sodium dodecyl sulfate (SDS), chlorhexidine, benzalkonium chloride, EDTA, silver nanopowder, silver compounds, glucose oxidase, lactose peroxidase, cadexomer iodine, methylene blue, gentian violet, medium-chain dextrans, sugar alcohol, or mixtures thereof.

20. The method of claim 18, wherein said amino acids 21-381 of SEQ ID NO:2, active fragment or variant having at least 95% sequence identity thereof is administered prior to administration of the antimicrobial agent and wherein the antimicrobial agent comprises sodium dodecyl sulfate, chlorhexidine, or benzalkonium chloride.

* * * * *

```
SEQUENCE LISTING

<160> NUMBER OF SEQ ID NOS: 15

<210> SEQ ID NO 1
<211> LENGTH: 1146
<212> TYPE: DNA
<213> ORGANISM: Actinobacillus actinomycetemcomitans strain CU100N

<400> SEQUENCE: 1
atgaattata ttaagaaaat tattttatct cttttcctac tgggactatt tagcgtgttg      60
aattgttgcg taaaaggcaa ttccatatat ccgcaaaaaa caagtaccaa gcagaccgga     120
ttaatgctgg acatcgcccg acattttat tcacccgagg tgattaaatc ctttattgat      180
accatcagcc tttccggcgg taattttctg cacctgcatt tttccgacca tgaaaactat     240
gcgatagaaa gccatttact taatcaacgt gcggaaaatg ccgtgcaggg caaagacggt     300
atttatatta atccttatac cggaaagcca ttcttgagtt atcggcaact tgacgatatc     360
aaagcctatg ctaaggcaaa aggcattgag ttgattcccg aacttgacag cccgaatcac     420
atgacggcga tctttaaact ggtgcaaaaa gacagagggg tcaagtacct tcaaggatta     480
aaatcacgcc aggtagatga tgaaattgat attactaatg ctgacagtat tacttttatg     540
caatctttaa tgagtgaggt tattgatatt tttggcgaca cgagtcagca ttttcatatt     600
ggtggcgatg aatttggtta ttctgtggaa agtaatcatg agtttattac gtatgccaat     660
aaactatcct acttttttaga gaaaaaggg ttgaaaccc gaatgtggaa tgacggatta     720
attaaaaata cttttgagca aatcaacccg aatattgaaa ttacttattg gagctatgat     780
```

```
ggcgatacgc aggacaaaaa tgaagctgcc gagcgccgtg atatgcgggt cagtttgccg      840
gagttgctgg cgaaaggctt tactgtcctg aactataatt cctattatct ttacattgtt      900
ccgaaagctt caccaacctt ctcgcaagat gccgcctttg ccgccaaaga tgttataaaa      960
aattgggatc ttggtgtttg ggatggacga acaccaaaa accgcgtaca aaatactcat     1020
gaaatagccg gcgcagcatt atcgatctgg ggagaagatg caaaagcgct gaaagacgaa     1080
acaattcaga aaaacacgaa aagtttattg gaagcggtga ttcataagac gaatggggat     1140
gagtga                                                                1146

<210> SEQ ID NO 2
<211> LENGTH: 381
<212> TYPE: PRT
<213> ORGANISM: Actinobacillus actinomycetemcomitans strain CU100N

<400> SEQUENCE: 2

Met Asn Tyr Ile Lys Lys Ile Ile Leu Ser Leu Phe Leu Leu Gly Leu
1               5                   10                  15

Phe Ser Val Leu Asn Cys Cys Val Lys Gly Asn Ser Ile Tyr Pro Gln
            20                  25                  30

Lys Thr Ser Thr Lys Gln Thr Gly Leu Met Leu Asp Ile Ala Arg His
        35                  40                  45

Phe Tyr Ser Pro Glu Val Ile Lys Ser Phe Ile Asp Thr Ile Ser Leu
    50                  55                  60

Ser Gly Gly Asn Phe Leu His Leu His Phe Ser Asp His Glu Asn Tyr
65                  70                  75                  80

Ala Ile Glu Ser His Leu Leu Asn Gln Arg Ala Glu Asn Ala Val Gln
                85                  90                  95

Gly Lys Asp Gly Ile Tyr Ile Asn Pro Tyr Thr Gly Lys Pro Phe Leu
            100                 105                 110

Ser Tyr Arg Gln Leu Asp Asp Ile Lys Ala Tyr Ala Lys Ala Lys Gly
        115                 120                 125

Ile Glu Leu Ile Pro Glu Leu Asp Ser Pro Asn His Met Thr Ala Ile
    130                 135                 140

Phe Lys Leu Val Gln Lys Asp Arg Gly Val Lys Tyr Leu Gln Gly Leu
145                 150                 155                 160

Lys Ser Arg Gln Val Asp Asp Glu Ile Asp Ile Thr Asn Ala Asp Ser
                165                 170                 175

Ile Thr Phe Met Gln Ser Leu Met Ser Glu Val Ile Asp Ile Phe Gly
            180                 185                 190

Asp Thr Ser Gln His Phe His Ile Gly Gly Asp Glu Phe Gly Tyr Ser
        195                 200                 205

Val Glu Ser Asn His Glu Phe Ile Thr Tyr Ala Asn Lys Leu Ser Tyr
    210                 215                 220

Phe Leu Glu Lys Lys Gly Leu Lys Thr Arg Met Trp Asn Asp Gly Leu
225                 230                 235                 240

Ile Lys Asn Thr Phe Glu Gln Ile Asn Pro Asn Ile Glu Ile Thr Tyr
                245                 250                 255

Trp Ser Tyr Asp Gly Asp Thr Gln Asp Lys Asn Glu Ala Ala Glu Arg
            260                 265                 270

Arg Asp Met Arg Val Ser Leu Pro Glu Leu Leu Ala Lys Gly Phe Thr
        275                 280                 285

Val Leu Asn Tyr Asn Ser Tyr Tyr Leu Tyr Ile Val Pro Lys Ala Ser
    290                 295                 300
```

```
Pro Thr Phe Ser Gln Asp Ala Ala Phe Ala Ala Lys Asp Val Ile Lys
305                 310                 315                 320

Asn Trp Asp Leu Gly Val Trp Asp Gly Arg Asn Thr Lys Asn Arg Val
            325                 330                 335

Gln Asn Thr His Glu Ile Ala Gly Ala Ala Leu Ser Ile Trp Gly Glu
            340                 345                 350

Asp Ala Lys Ala Leu Lys Asp Glu Thr Ile Gln Lys Asn Thr Lys Ser
            355                 360                 365

Leu Leu Glu Ala Val Ile His Lys Thr Asn Gly Asp Glu
370                 375                 380
```

<210> SEQ ID NO 3
<211> LENGTH: 555
<212> TYPE: DNA
<213> ORGANISM: Actinobacillus ligniersii strain 19393

<400> SEQUENCE: 3

```
gatcacgaga attatgcatt ggaaagttct tatttggaac aacgagaaga aaatgccgtt      60
gagaaaaacg gaacctattt caatccgaaa acaaataagc cgtttctcac ttataaacag     120
ctcaatgaaa ttatctatta tgccaaagaa cgaaatattg aaattgtgcc tgaagtcgat     180
agcccgaatc atatgacggc gattttgat cttttaaccc ttaagcacgg taaggagtat      240
gtgaagggc tgaaatcgcc ttatcttgcc gaggaaatcg atattaataa ccctgaagcg      300
gttgaaatta tcaaaacctt aatcggtgaa gtgatttata ttttgggca ttccagccga      360
cactttcata tcggcggaga cgaatttagt tatgcggtcg aaaacaatca cgaatttatt     420
cgttatgtaa atacgctaaa tgactttatt aataacaaag gactaattac ccgtatttgg     480
aacgacggtt tgattaaaaa caatttaaat gagcttaatc ggaatatcga aattacttat     540
tggagctacg acggt                                                      555
```

<210> SEQ ID NO 4
<211> LENGTH: 185
<212> TYPE: PRT
<213> ORGANISM: Actinobacillus ligniersii strain 19393

<400> SEQUENCE: 4

```
Asp His Glu Asn Tyr Ala Leu Glu Ser Ser Tyr Leu Glu Gln Arg Glu
1               5                   10                  15

Glu Asn Ala Val Glu Lys Asn Gly Thr Tyr Phe Asn Pro Lys Thr Asn
            20                  25                  30

Lys Pro Phe Leu Thr Tyr Lys Gln Leu Asn Glu Ile Ile Tyr Tyr Ala
        35                  40                  45

Lys Glu Arg Asn Ile Glu Ile Val Pro Glu Val Asp Ser Pro Asn His
50                  55                  60

Met Thr Ala Ile Phe Asp Leu Leu Thr Leu Lys His Gly Lys Glu Tyr
65                  70                  75                  80

Val Lys Gly Leu Lys Ser Pro Tyr Leu Ala Glu Glu Ile Asp Ile Asn
                85                  90                  95

Asn Pro Glu Ala Val Glu Ile Ile Lys Thr Leu Ile Gly Glu Val Ile
            100                 105                 110

Tyr Ile Phe Gly His Ser Ser Arg His Phe His Ile Gly Gly Asp Glu
        115                 120                 125

Phe Ser Tyr Ala Val Glu Asn Asn His Glu Phe Ile Arg Tyr Val Asn
130                 135                 140

Thr Leu Asn Asp Phe Ile Asn Asn Lys Gly Leu Ile Thr Arg Ile Trp
```

```
                145                 150                 155                 160
Asn Asp Gly Leu Ile Lys Asn Asn Leu Asn Glu Leu Asn Arg Asn Ile
                    165                 170                 175

Glu Ile Thr Tyr Trp Ser Tyr Asp Gly
                    180                 185

<210> SEQ ID NO 5
<211> LENGTH: 558
<212> TYPE: DNA
<213> ORGANISM: Actinobacillus actinomycetemcomitans strain IDH781

<400> SEQUENCE: 5
gatcatgaaa actatgcgat agaaagccat ttacttaatc aacgtgcgga aaatgccgta      60
cagggcaaag acgtattta tattaatcct tataccggaa agccattctt gagttatcga     120
caacttgacg atatcaaagc ctatgctaag gcaaaaggca ttgagttgat tcccgaactt     180
gatagtccga atcacatgac ggcgatcttt aaactggtgc aaaaagacag agggatcaag     240
tatcttcaag gattaaaatc acgccaggta gatgatgaaa ttgatattac taatgctgac     300
agtattgctt ttatgcaatc tttaatgagt gaggttattg atattttggg cgacacgagt     360
cagcattttc atattggtgg cgatgaattt ggttattctg tggaaagtaa tcatgagttt     420
attacgtatg ccaataaact atcctacttt ttagagaaaa aggggttgaa acccgaatg     480 tggaatgacg gattaattaa aagtactttt gagcaaatca acccgaatat tgaaattact     540
tattggagct atgatggc                                                  558

<210> SEQ ID NO 6
<211> LENGTH: 186
<212> TYPE: PRT
<213> ORGANISM: Actinobacillus actinomycetemcomitans strain IDH781

<400> SEQUENCE: 6

Asp His Glu Asn Tyr Ala Ile Glu Ser His Leu Leu Asn Gln Arg Ala
1               5                   10                  15

Glu Asn Ala Val Gln Gly Lys Asp Gly Ile Tyr Ile Asn Pro Tyr Thr
                20                  25                  30

Gly Lys Pro Phe Leu Ser Tyr Arg Gln Leu Asp Asp Ile Lys Ala Tyr
            35                  40                  45

Ala Lys Ala Lys Gly Ile Glu Leu Ile Pro Glu Leu Asp Ser Pro Asn
        50                  55                  60

His Met Thr Ala Ile Phe Lys Leu Val Gln Lys Asp Arg Gly Ile Lys
65                  70                  75                  80

Tyr Leu Gln Gly Leu Lys Ser Arg Gln Val Asp Asp Glu Ile Asp Ile
                85                  90                  95

Thr Asn Ala Asp Ser Ile Ala Phe Met Gln Ser Leu Met Ser Glu Val
                100                 105                 110

Ile Asp Ile Phe Gly Asp Thr Ser Gln His Phe His Ile Gly Gly Asp
            115                 120                 125

Glu Phe Gly Tyr Ser Val Glu Ser Asn His Glu Phe Ile Thr Tyr Ala
        130                 135                 140

Asn Lys Leu Ser Tyr Phe Leu Glu Lys Lys Gly Leu Lys Thr Arg Met
145                 150                 155                 160

Trp Asn Asp Gly Leu Ile Lys Ser Thr Phe Glu Gln Ile Asn Pro Asn
                165                 170                 175

Ile Glu Ile Thr Tyr Trp Ser Tyr Asp Gly
                180                 185
```

<210> SEQ ID NO 7
<211> LENGTH: 558
<212> TYPE: DNA
<213> ORGANISM: Haemophilus aphorophilus strain NJ8700

<400> SEQUENCE: 7

```
gaccacgaaa attatgcttt agaaagcagg ttgttgaatc agcgggcaga aaacgcaatt      60
ttaaataaaa acggaattta tattaatcct tacaccaata agcctttctt gagttatcaa     120
cagttggatg acattaaagc atatgcaaaa ttaaaggta ttgagcttat tcccgaatta      180
gatagcccga tcacatgac agcgattttt accttattaa aaaagaaaa aggaaaaat       240 tatcttcaat cgttaaaatc accacaaaat gatgaggaaa ttagcattac caatccggac    300
agcattgcat ttatgcaatc cttattaaca gaggtaattc atacctttgg cgatagcacc    360
aagcattttc atattggcgg agatgagttt ggttatgatg aaaatagtaa tcatgaattt    420
attacctatg ccaataaatt ggctgatttt taagagaaa aaggattaaa aactcgaatt     480
tggaatgatg gtttaattaa aaataccata gatcaattaa atcctaatat tgaaattacc    540
tactggagtt acgacggc                                                   558
```

<210> SEQ ID NO 8
<211> LENGTH: 186
<212> TYPE: PRT
<213> ORGANISM: Haemophilus aphrophilus strain NJ8700

<400> SEQUENCE: 8

```
Asp His Glu Asn Tyr Ala Leu Glu Ser Arg Leu Leu Asn Gln Arg Ala
1               5                   10                  15

Glu Asn Ala Ile Leu Asn Lys Asn Gly Ile Tyr Ile Asn Pro Tyr Thr
            20                  25                  30

Asn Lys Pro Phe Leu Ser Tyr Gln Gln Leu Asp Asp Ile Lys Ala Tyr
        35                  40                  45

Ala Lys Leu Lys Gly Ile Glu Leu Ile Pro Glu Leu Asp Ser Pro Asn
    50                  55                  60

His Met Thr Ala Ile Phe Thr Leu Leu Lys Lys Glu Lys Gly Lys Asn
65                  70                  75                  80

Tyr Leu Gln Ser Leu Lys Ser Pro Gln Asn Asp Glu Glu Ile Ser Ile
                85                  90                  95

Thr Asn Pro Asp Ser Ile Ala Phe Met Gln Ser Leu Leu Thr Glu Val
            100                 105                 110

Ile His Thr Phe Gly Asp Ser Thr Lys His Phe His Ile Gly Gly Asp
        115                 120                 125

Glu Phe Gly Tyr Asp Glu Asn Ser Asn His Glu Phe Ile Thr Tyr Ala
    130                 135                 140

Asn Lys Leu Ala Asp Phe Leu Arg Glu Lys Gly Leu Lys Thr Arg Ile
145                 150                 155                 160

Trp Asn Asp Gly Leu Ile Lys Asn Thr Ile Asp Gln Leu Asn Pro Asn
                165                 170                 175

Ile Glu Ile Thr Tyr Trp Ser Tyr Asp Gly
            180                 185
```

<210> SEQ ID NO 9
<211> LENGTH: 555
<212> TYPE: DNA
<213> ORGANISM: Actinobacillus pleuropneumoniae strain IA5

<400> SEQUENCE: 9

```
gatcacgaga attatgcatt ggaaagttct tatttggaac aacgagaaga aaatgcgacc    60
gagaaaaacg gaacctattt caatccgaaa acaaataagc cgtttctcac ttataaacag   120
ctcaatgaaa ttatctatta tgccaaagaa cgaaatattg aaattgtgcc tgaagtcgat   180
agcccgaatc atatgacggc gatttttgat cttttaaccc ttaagcacgg aaaggaatac   240
gtaaaagggc taaatcgcc ttatatcgcc gaggaaatcg atattaataa ccccgaagcg    300
gttgaagtta ttaaaacctt aatcggtgaa gtgatctata ttttcggaca ttcaagccgg   360
catttccata tcggcggaga tgaatttagc tatgcggtcg aaaataatca tgaatttatt   420
cggtatgtga ataccttaaa tgattttatc aattccaaag ggctaattac ccgtgtttgg   480
aatgacggtt tgatcaaaaa caacttaagc gaactcaata aaacattga atcacttac    540
tggagctacg acggt                                                    555
```

<210> SEQ ID NO 10
<211> LENGTH: 185
<212> TYPE: PRT
<213> ORGANISM: Actinobacillus pleuropneumoniae strain IA5

<400> SEQUENCE: 10

```
Asp His Glu Asn Tyr Ala Leu Glu Ser Ser Tyr Leu Glu Gln Arg Glu
1               5                   10                  15

Glu Asn Ala Thr Glu Lys Asn Gly Thr Tyr Phe Asn Pro Lys Thr Asn
                20                  25                  30

Lys Pro Phe Leu Thr Tyr Lys Gln Leu Asn Glu Ile Ile Tyr Tyr Ala
            35                  40                  45

Lys Glu Arg Asn Ile Glu Ile Val Pro Glu Val Asp Ser Pro Asn His
        50                  55                  60

Met Thr Ala Ile Phe Asp Leu Leu Thr Leu Lys His Gly Lys Glu Tyr
65                  70                  75                  80

Val Lys Gly Leu Lys Ser Pro Tyr Ile Ala Glu Ile Asp Ile Asn
                85                  90                  95

Asn Pro Glu Ala Val Glu Val Ile Lys Thr Leu Ile Gly Glu Val Ile
                100                 105                 110

Tyr Ile Phe Gly His Ser Ser Arg His Phe His Ile Gly Gly Asp Glu
            115                 120                 125

Phe Ser Tyr Ala Val Glu Asn Asn His Glu Phe Ile Arg Tyr Val Asn
        130                 135                 140

Thr Leu Asn Asp Phe Ile Asn Ser Lys Gly Leu Ile Thr Arg Val Trp
145                 150                 155                 160

Asn Asp Gly Leu Ile Lys Asn Asn Leu Ser Glu Leu Asn Lys Asn Ile
                165                 170                 175

Glu Ile Thr Tyr Trp Ser Tyr Asp Gly
            180                 185
```

<210> SEQ ID NO 11
<211> LENGTH: 361
<212> TYPE: PRT
<213> ORGANISM: Actinobacillus actinomycetemcomitans

<400> SEQUENCE: 11

```
Asn Cys Cys Val Lys Gly Asn Ser Ile Tyr Pro Gln Lys Thr Ser Thr
1               5                   10                  15

Lys Gln Thr Gly Leu Met Leu Asp Ile Ala Arg His Phe Tyr Ser Pro
                20                  25                  30
```

Glu Val Ile Lys Ser Phe Ile Asp Thr Ile Ser Leu Ser Gly Gly Asn
         35                  40                  45

Phe Leu His Leu His Phe Ser Asp His Glu Asn Tyr Ala Ile Glu Ser
 50                  55                  60

His Leu Asn Gln Arg Ala Glu Asn Ala Val Gln Gly Lys Asp Gly
 65                  70                  75                  80

Ile Tyr Ile Asn Pro Tyr Thr Gly Lys Pro Phe Leu Ser Tyr Arg Gln
                 85                  90                  95

Leu Asp Asp Ile Lys Ala Tyr Ala Lys Ala Lys Gly Ile Glu Leu Ile
                100                 105                 110

Pro Glu Leu Asp Ser Pro Asn His Met Thr Ala Ile Phe Lys Leu Val
                115                 120                 125

Gln Lys Asp Arg Gly Val Lys Tyr Leu Gln Gly Leu Lys Ser Arg Gln
130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
                165                 170                 175

His Phe His Ile Gly Gly Asp Glu Phe Gly Tyr Ser Val Glu Ser Asn
                180                 185                 190

His Glu Phe Ile Thr Tyr Ala Asn Lys Leu Ser Tyr Phe Leu Glu Lys
                195                 200                 205

Lys Gly Leu Lys Thr Arg Met Trp Asn Asp Gly Leu Ile Lys Asn Thr
210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
                245                 250                 255

Val Ser Leu Pro Glu Leu Leu Ala Lys Gly Phe Thr Val Leu Asn Tyr
                260                 265                 270

Asn Ser Tyr Tyr Leu Tyr Ile Val Pro Lys Ala Ser Pro Thr Phe Ser
                275                 280                 285

Gln Asp Ala Ala Phe Ala Ala Lys Asp Val Ile Lys Asn Trp Asp Leu
290                 295                 300

Gly Val Trp Asp Gly Arg Asn Thr Lys Asn Arg Val Gln Asn Thr His
305                 310                 315                 320

Glu Ile Ala Gly Ala Ala Leu Ser Ile Trp Gly Glu Asp Ala Lys Ala
                325                 330                 335

Leu Lys Asp Glu Thr Ile Gln Lys Asn Thr Lys Ser Leu Leu Glu Ala
                340                 345                 350

Val Ile His Lys Thr Asn Gly Asp Glu
                355                 360

<210> SEQ ID NO 12
<211> LENGTH: 377
<212> TYPE: PRT
<213> ORGANISM: Actinobacillus pleuropneumoniae

<400> SEQUENCE: 12

Met Lys Lys Ala Ile Thr Leu Phe Thr Leu Leu Cys Ala Val Leu Leu
 1               5                  10                  15

Ser Phe Ser Thr Ala Thr Tyr Ala Asn Ala Met Asp Leu Pro Lys Lys
                20                  25                  30

Glu Ser Gly Leu Thr Leu Asp Ile Ala Arg Arg Phe Tyr Thr Val Asp

```
            35                  40                  45
Thr Ile Lys Gln Phe Ile Asp Thr Ile His Gln Ala Gly Gly Thr Phe
 50                  55                  60
Leu His Leu His Phe Ser Asp His Glu Asn Tyr Ala Leu Glu Ser Ser
 65                  70                  75                  80
Tyr Leu Glu Gln Arg Glu Glu Asn Ala Thr Glu Lys Asn Gly Thr Tyr
                 85                  90                  95
Phe Asn Pro Lys Thr Asn Lys Pro Phe Leu Thr Tyr Lys Gln Leu Asn
                100                 105                 110
Glu Ile Ile Tyr Tyr Ala Lys Glu Arg Asn Ile Glu Ile Val Pro Glu
            115                 120                 125
Val Asp Ser Pro Asn His Met Thr Ala Ile Phe Asp Leu Leu Thr Leu
130                 135                 140
Lys His Gly Lys Glu Tyr Val Lys Gly Leu Lys Ser Pro Tyr Ile Ala
145                 150                 155                 160
Glu Glu Ile Asp Ile Asn Asn Pro Glu Ala Val Glu Val Ile Lys Thr
                165                 170                 175
Leu Ile Gly Glu Val Ile Tyr Ile Phe Gly His Ser Ser Arg His Phe
            180                 185                 190
His Ile Gly Gly Asp Glu Phe Ser Tyr Ala Val Glu Asn Asn His Glu
        195                 200                 205
Phe Ile Arg Tyr Val Asn Thr Leu Asn Asp Phe Ile Asn Ser Lys Gly
210                 215                 220
Leu Ile Thr Arg Val Trp Asn Asp Gly Leu Ile Lys Asn Asn Leu Ser
225                 230                 235                 240
Glu Leu Asn Lys Asn Ile Glu Ile Thr Tyr Trp Ser Tyr Asp Gly Asp
                245                 250                 255
Ala Gln Ala Lys Glu Asp Ile Gln Tyr Arg Arg Glu Ile Arg Ala Asp
            260                 265                 270
Leu Pro Glu Leu Leu Ala Asn Gly Phe Lys Val Leu Asn Tyr Asn Ser
        275                 280                 285
Tyr Tyr Leu Tyr Phe Val Pro Lys Ser Gly Ser Asn Ile His Asn Asp
290                 295                 300
Gly Lys Tyr Ala Ala Glu Asp Val Leu Asn Asn Trp Thr Leu Gly Lys
305                 310                 315                 320
Trp Asp Gly Lys Asn Ser Ser Asn His Val Gln Asn Thr Gln Asn Ile
                325                 330                 335
Ile Gly Ser Ser Leu Ser Ile Trp Gly Glu Arg Ser Ser Ala Leu Asn
            340                 345                 350
Glu Gln Thr Ile Gln Gln Ala Ser Lys Asn Leu Leu Lys Ala Val Ile
        355                 360                 365
Gln Lys Thr Asn Asp Pro Lys Ser His
370                 375

<210> SEQ ID NO 13
<211> LENGTH: 22
<212> TYPE: DNA
<213> ORGANISM: Artificial
<220> FEATURE:
<223> OTHER INFORMATION: DNA Primer UTCF1

<400> SEQUENCE: 13
gtgcaatcca ttaattttgg tg                                           22

<210> SEQ ID NO 14
```

```
<211> LENGTH: 19
<212> TYPE: DNA
<213> ORGANISM: Artificial
<220> FEATURE:
<223> OTHER INFORMATION: DNA Primer UTCR

<400> SEQUENCE: 14
catacgtatc ctccaagcc                                              19

<210> SEQ ID NO 15
<211> LENGTH: 8
<212> TYPE: PRT
<213> ORGANISM: Artificial
<220> FEATURE:
<223> OTHER INFORMATION: Linker sequence

<400> SEQUENCE: 15

Gly Gly Gly Ser Gly Gly Gly Ser
1               5
```